United States Patent
Gray et al.

(10) Patent No.: US 11,273,075 B2
(45) Date of Patent: *Mar. 15, 2022

(54) SYSTEM AND APPARATUS FOR TREATING THE LENS OF AN EYE

(71) Applicant: Lensar, Inc., Orlando, FL (US)

(72) Inventors: Gary P. Gray, Orlando, FL (US); Rudolph W. Frey, Maitland, FL (US); Dennis R. Pape, Orlando, FL (US); George R. Downes, Orlando, FL (US); Jorge A. De Castro, Orlando, FL (US); Jerome R. Kuszak, Oak Park, IL (US)

(73) Assignee: Lensar, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/109,620

(22) Filed: Aug. 22, 2018

(65) Prior Publication Data

US 2019/0060123 A1 Feb. 28, 2019

Related U.S. Application Data

(60) Division of application No. 14/874,325, filed on Oct. 2, 2015, now Pat. No. 10,085,888, which is a division (Continued)

(51) Int. Cl.
*A61F 9/008* (2006.01)
*A61B 90/30* (2016.01)
(Continued)

(52) U.S. Cl.
CPC .......... *A61F 9/00834* (2013.01); *A61B 90/30* (2016.02); *A61F 9/008* (2013.01);
(Continued)

(58) Field of Classification Search
CPC .. A61F 9/008; A61F 9/00804; A61F 9/00825; A61F 9/00834; A61F 9/00838; A61F 9/00851; A61F 2009/00861; A61F 2009/0087; A61F 2009/00885; A61F 2009/00887; A61F 2009/00897; A61F 9/00802; A61F 9/00808; A61F 2009/00844; A61F 2009/00895; A61F 2009/009; A61F 2009/00851; A61B 18/20;
(Continued)

(56) References Cited

U.S. PATENT DOCUMENTS

| 4,538,608 A | 9/1985 | L'Esperance |
| 4,764,930 A | 8/1988 | Bille |

(Continued)

*Primary Examiner* — Ahmed M Farah
(74) *Attorney, Agent, or Firm* — Glen P. Belvis; Belvis Law, LLC.

(57) ABSTRACT

A system and apparatus for increasing the amplitude of accommodation and/or changing the refractive power and/or enabling the removal of the clear or cataractous lens material of a natural crystalline lens is provided. Generally, the system comprises a laser, optics for delivering the laser beam and a control system for delivering the laser beam to the lens in a particular pattern. There is further provided apparatus for determining the shape and position of the lens with respect to the laser. There is yet further provided a method and system for delivering a laser beam in the lens of the eye in a predetermined shot pattern.

6 Claims, 37 Drawing Sheets

Related U.S. Application Data of application No. 11/414,819, filed on May 1, 2006, now Pat. No. 9,180,051, which is a continuation-in-part of application No. 11/337,127, filed on Jan. 20, 2006, now Pat. No. 10,842,675.

(51) Int. Cl.
*A61B 18/20* (2006.01)
*A61B 90/00* (2016.01)
*A61F 9/007* (2006.01)

(52) U.S. Cl.
CPC ... *A61B 90/361* (2016.02); *A61B 2018/20351* (2017.05); *A61B 2018/20355* (2017.05); *A61B 2018/20361* (2017.05); *A61F 9/00736* (2013.01); *A61F 2009/0087* (2013.01); *A61F 2009/00887* (2013.01); *A61F 2009/00897* (2013.01)

(58) Field of Classification Search
CPC .. A61B 2018/2035; A61B 2018/20351; A61B 2018/20353; A61B 90/30; A61B 90/36; A61B 90/361; A61B 90/3612; A61B 2018/205547
USPC .............................................. 606/4–6, 10–12
See application file for complete search history.

(56) References Cited

U.S. PATENT DOCUMENTS

| | | | |
|---|---|---|---|
| 4,901,718 A | 2/1990 | Bille | |
| 4,907,586 A | 3/1990 | Bille | |
| 5,054,907 A * | 10/1991 | Sklar | G01B 11/2513 351/212 |
| 5,098,426 A | 3/1992 | Sklar | |
| 5,246,435 A | 9/1993 | Bille | |
| 5,355,181 A | 10/1994 | Ashizaki | |
| 5,439,462 A | 8/1995 | Bille | |
| 5,480,396 A | 1/1996 | Simon | |
| 6,004,314 A | 12/1999 | Wei | |
| 6,099,522 A | 8/2000 | Knopp | |
| 6,197,018 B1 | 3/2001 | O'Donnell | |
| 6,312,422 B1 | 6/2001 | Dubnack | |
| 6,322,556 B1 | 11/2001 | Gwon | |
| 6,325,792 B1 | 12/2001 | Swinger | |
| 7,655,002 B2 | 2/2010 | Myers | |
| 8,262,646 B2 | 9/2012 | Frey | |
| 8,382,745 B2 | 2/2013 | Naranjo-Tackman | |
| 8,394,084 B2 * | 3/2013 | Palankar | A61F 9/00825 606/6 |
| 8,403,921 B2 | 3/2013 | Palankar et al. | |
| 8,425,497 B2 | 4/2013 | Blumenkranz et al. | |
| 8,465,478 B2 | 6/2013 | Frey | |
| 8,480,659 B2 | 7/2013 | Frey | |
| 8,500,723 B2 | 8/2013 | Frey | |
| 8,617,146 B2 | 12/2013 | Frey | |
| 8,758,332 B2 | 6/2014 | Frey | |
| 8,801,186 B2 | 8/2014 | Frey | |
| 9,180,051 B2 * | 11/2015 | Frey | A61F 9/008 |
| 9,375,349 B2 | 6/2016 | Frey | |
| 9,545,338 B2 | 1/2017 | Frey | |
| 9,889,043 B2 * | 2/2018 | Frey | A61F 9/00827 |
| 10,085,888 B2 * | 10/2018 | Frey | A61F 9/008 |
| 10,684,449 B2 * | 6/2020 | Curatu | G02B 13/0005 |
| 10,842,675 B2 * | 11/2020 | Frey | A61F 9/00834 |
| 2003/0139737 A1 * | 7/2003 | Lin | A61B 18/14 606/5 |
| 2006/0195076 A1 * | 8/2006 | Blumenkranz | A61F 9/00736 606/4 |
| 2007/0173794 A1 | 7/2007 | Frey | |
| 2008/0287928 A1 | 11/2008 | Arnoldussen | |
| 2010/0004641 A1 | 1/2010 | Frey | |
| 2016/0302971 A1 | 10/2016 | Morely | |

\* cited by examiner

SYSTEM AND APPARATUS FOR TREATING THE LENS OF AN EYE

This application is a divisional of U.S. patent application Ser. No. 14/874,325 filed Oct. 2, 2015, which is a divisional of U.S. patent application Ser. No. 11/414,819, filed on May 1, 2006, which is a continuation-in-part of pending application Frey et al. Ser. No. 11/337,127 filed Jan. 20, 2006, the entire disclosure of each of which are incorporated herein by reference. This application incorporates by reference U.S. Pat. No. 8,262,646, filed on the same date as U.S. patent application Ser. No. 11/414,819. The present invention relates to systems and apparatus for treating the structure of the natural human crystalline lens with a laser to address a variety of medical conditions such as presbyopia, refractive error and cataracts and combinations of these.

BACKGROUND OF THE INVENTION

The anatomical structures of the eye are shown in general in FIG. 1, which is a cross sectional view of the eye. The sclera 131 is the white tissue that surrounds the lens 103 except at the cornea 101. The cornea 101 is the transparent tissue that comprises the exterior surface of the eye through which light first enters the eye. The iris 102 is a colored, contractible membrane that controls the amount of light entering the eye by changing the size of the circular aperture at its center (the pupil). The ocular or natural crystalline lens 103, a more detailed picture of which is shown in FIGS. 1A-F, (utilizing similar reference numbers for similar structures) is located just posterior to the iris 102. The terms ocular lens, natural crystalline lens, natural lens, natural human crystalline lens, and lens (when referring to the prior terms) are used interchangeably herein and refer to the same anatomical structure of the human eye.

Generally, the ocular lens changes shape through the action of the ciliary muscle 108 to allow for focusing of a visual image. A neural feedback mechanism from the brain allows the ciliary muscle 108, acting through the attachment of the zonules 111, to change the shape of the ocular lens. Generally, sight occurs when light enters the eye through the cornea 101 and pupil, then proceeds through the ocular lens 103 through the vitreous 110 along the visual axis 104, strikes the retina 105 at the back of the eye, forming an image at the macula 106 that is transferred by the optic nerve 107 to the brain. The space between the cornea 101 and the retina 105 is filled with a liquid called the aqueous 117 in the anterior chamber 109 and the vitreous 110, a gel-like clear substance, in the chamber posterior to the lens 103.

FIG. 1A illustrates, in general, components of and related to the lens 103 for a typical 50-year old individual. The lens 103 is a multi-structural system. The lens 103 structure includes a cortex 113, and a nucleus 129, and a lens capsule 114. The capsule 114 is an outer membrane that envelopes the other interior structures of the lens. The lens epithelium 123 forms at the lens equatorial 121 generating ribbon-like cells or fibrils that grow anteriorly and posteriorly around the ocular lens. The nucleus 129 is formed from successive additions of the cortex 113 to the nuclear regions. The continuum of layers in the lens, including the nucleus 129, can be characterized into several layers, nuclei or nuclear regions. These layers include an embryonic nucleus 122, a fetal nucleus 130, both of which develop in the womb, an infantile nucleus 124, which develops from birth through four years for an average of about three years, an adolescent nucleus 126, which develops from about four years until puberty which averages about 12 years, and the adult nucleus 128, which develops at about 18 years and beyond.

The embryonic nucleus 122 is about 0.5 mm in equatorial diameter (width) and 0.425 mm in Anterior-Posterior axis 104 (AP axis) diameter (thickness). The fetal nucleus 130 is about 6.0 mm in equatorial diameter and 3.0 mm in AP axis 104 diameter. The infantile nucleus 124 is about 7.2 mm in equatorial diameter and 3.6 mm in AP axis 104 diameter. The adolescent nucleus 126 is about 9.0 mm in equatorial diameter and 4.5 mm in AP axis 104 diameter. The adult nucleus 128 at about age 36 is about 9.6 mm in equatorial diameter and 4.8 mm in AP axis 104 diameter. These are all average values for a typical adult human lens approximately age 50 in the accommodated state, ex vivo. Thus this lens (nucleus and cortex) is about 9.8 mm in equatorial diameter and 4.9 mm in AP axis 104 diameter. Thus, the structure of the lens is layered or nested, with the oldest layers and oldest cells towards the center.

The lens is a biconvex shape as shown in FIGS. 1 and 1A. The anterior and posterior sides of the lens have different curvatures and the cortex and the different nuclei in general follow those curvatures. Thus, the lens can be viewed as essentially a stratified structure that is asymmetrical along the equatorial axis and consisting of long crescent fiber cells arranged end to end to form essentially concentric or nested shells. The ends of these cells align to form suture lines in the central and paracentral areas both anteriorly and posteriorly. The older tissue in both the cortex and nucleus has reduced cellular function, having lost their cell nuclei and other organelles several months after cell formation.

Compaction of the lens occurs with aging. The number of lens fibers that grow each year is relatively constant throughout life. However, the size of the lens does not become as large as expected from new fiber growth. The lens grows from birth through age 3, from 6 mm to 7.2 mm or 20% growth in only 3 years. Then the next approximate decade, growth is from 7.2 mm to 9 mm or 25%; however, this is over a 3 times longer period of 9 years. Over the next approximate 2 decades, from age 12 to age 36 the lens grows from 9 mm to 9.6 mm or 6.7% growth in 24 years, showing a dramatically slowing observed growth rate, while we believe there is a relatively constant rate of fiber growth during this period. Finally, in the last approximately 2 decades described, from age 36 to age 54, the lens grows by a tiny fraction of its youthful growth, from 9.6 to 9.8 mm or 2.1% in 18 years. Although there is a geometry effect of needing more lens fibers to fill larger outer shells, the size of the older lens is considerably smaller than predicted by fiber growth rate models, which consider geometry effects. Fiber compaction including nuclear fiber compaction is thought to explain these observations.

In general, presbyopia is the loss of accommodative amplitude. In general refractive error is typically due to variations in the axial length of the eye. Myopia is when the eye is too long resulting in the focus falling in front of the retina. Hyperopia is when the eye is too short resulting in the focus falling behind the retina. In generally, cataracts are areas of opacification of the ocular lens which are sufficient to interfere with vision. Other conditions, for which the present invention is directed, include but are not limited to the opacification of the ocular lens.

Presbyopia most often presents as a near vision deficiency, the inability to read small print, especially in dim lighting after about 40-45 years of age. Presbyopia, or the loss of accommodative amplitude with age, relates to the eyes inability to change the shape of the natural crystalline lens, which allows a person to change focus between far and near, and occurs in essentially 100% of the population. Accommodative amplitude has been shown to decline with age steadily through the fifth decade of life.

Historically, studies have generally attributed loss of accommodation to the hardening of the crystalline lens with age and more specifically, to an increase in the Young's Modulus of Elasticity of the lens material. More recent studies have examined the effect of aging on the relative change in material properties between the nucleus and cortex. These studies have provided varying theories and data with respect to the hardening of the lens. In general, such studies have essentially proposed the theory that the loss of flexibility is the result of an increase in the Young's Modulus of Elasticity of the nucleus and/or cortex material. Such studies have viewed this hardening as the primary factor in the loss of accommodative amplitude with age and hence the cause of presbyopia.

Although the invention is not bound by it, the present specification postulates a different theory of how this loss of lens flexibility occurs to cause presbyopia. In general, it is postulated the structure of the lens rather than the material properties of the lens plays a greater role in loss of flexibility and resultant presbyopia than was previously understood. Thus, contrary to the teachings of the prior studies in this field as set forth above, material elasticity is not the dominate cause of presbyopla. Rather, it is postulated that it is the structure of the lens and changes in that structure with age that is the dominant cause of presbyopia. Thus, without being limited to or bound by this theory, the present invention discloses a variety of methods and systems to provide laser treatments to increase the flexibility of the lens, based at least in part on the structure of the lens and structural changes that occur to the lens with aging. The present invention further discloses providing laser treatments to increase the flexibility of the lens that are based primarily on the structure of the lens and structural changes that occur to the lens with aging.

Accordingly, the postulated theory of this specification can be illustrated for exemplary purposes by looking to and examining a simple hypothetical model. It further being understood this hypothetical model is merely to illustrate the present theory and not to predict how a lens will react to laser pulses, and/or structural changes. To understand how important structure alone can be, consider a very thin plank of wood, say 4 ft by 4 ft square but 0.1 inch thick. This thin plank is not very strong and if held firmly on one end, it does not take much force to bend this thin plank considerably. Now consider five of these same 0.1 inch thickness planks stacked on top of each other, but otherwise not bound or tied together. The strength would increase and for the same force a somewhat smaller deflection will occur. Now, consider taking those same five planks and fastening them together with many screws or by using very strong glue, or by using many C-Clamps to bind them together. The strength of the bound planks is much higher and the deflection seen from the same force would be much smaller.

Without saying this simple model reflects the complex behavior of the lens, we generally hypothesize that when considering a volume of lens material, especially near the poles (AP axis), that is essentially bound by increased friction and compaction due to aging, that separating those bound layers into essentially unbound layers will increase the deflection of those layers for the same applied force and hence increase flexibility of the lens. Applicants, however, do not intend to be bound by the present theory, and it is provided solely to advance the art, and is not intended to and does not restrict or diminish the scope of the invention, Thus, further using this model for illustration purposes, under the prior theories and treatments for presbyopia, the direction was principally toward the material properties, i.e., Modulus of the material in the stack, rather than on the structure of the stack, i.e., whether the layers were bound together. On the other hand, the presently postulated theory is directed toward structural features and the effects that altering those features have on flexibility.

In general, current presbyopia treatments tend to be directed toward alternatives to increasing the amplitude of accommodation of the natural crystalline lens. These treatments include a new class of artificial accommodative Intraocular Lenses (IOL's), such as the Eyeonics CRYSTALENS, which are designed to change position within the eye; however, they offer only about 1 diopter of objectively measured accommodative amplitude, while many practitioners presently believe 3 or more diopters are required to restore normal visual function for near and far objects. Moreover, researchers are pursuing techniques and materials to refill the lens capsule with synthetic materials. Additionally, present surgical techniques to implant artificial accommodative IOL's are those developed for the more serious condition of cataracts. It is believed that practitioners are reluctant at the present time to replace a patient's clear albeit presbyopic natural crystalline lens, with an accommodative IOL due to the risks of this invasive surgical technique on a patient who may simply wear reading glasses to correct the near vision deficiency. However, developments may offer greater levels of accommodative amplitude in implantable devices and refilling materials. To better utilize such device improvements and to increase the accommodative amplitude of existing implantable devices, improved surgical techniques are provided herein as a part of the present invention.

Refractive error, typically due to the length of the eye being too long (myopia) or to short (hyperopia) is another very common problem effecting about one-half of the population. Laser surgery on the cornea, as proposed by Trokel and L'Esperance and improved by Frey and others, does offer effective treatment of refractive errors but factors such as higher degrees of refractive error, especially in hyperopia, thin corneas or a changing refractive error with time, such as that brought on by presbyopia, limit the clinical use of laser corneal surgery for many.

SUMMARY

Provided herein are embodiments of the present invention. Accordingly, there is provided a system and apparatus for delivering a laser beam to a lens of an eye that utilize a laser, an optical path for directing a laser beam from the laser to the lens of the eye, a means for determining the shape and position of the lens with respect to a fixed point, and means for focusing a laser beam to a location in the lens of the eye, wherein that location was determined based at least in part upon data and/or information from the determining step.

There is further provided a system and apparatus for delivering a laser beam in the lens of the eye in a predetermined shot pattern that utilize as series of shots that form a shell cut, a partial shell cut, a laser suture cut and/or a volumetric shaped removal, which essentially following the shape of a suture layer of the lens, i.e., a layer shape of the lens.

There is further provided a system and apparatus for treating conditions of the lens comprising a laser, laser focusing optics, a scanner and a control system that has a plurality of means for directing in cooperation with the laser, the scanner and the laser focusing optics, laser shot patterns.

There is further provided a system for delivering a laser to an eye and for obtaining stereo images of the eye comprising a laser, focusing optics, a scanner and a camera. Wherein the scanner is optically associated with the laser and the camera so that the scanner has the capability to provide stereo pairs of images of the eye and deliver a laser beam from the laser to the eye.

There is also provided a system and apparatus for treating conditions of the lens comprising: a laser, laser focusing optics, a scanner, a control system, a predetermined lens shot pattern, and a means for determining the position of the lens, wherein the means for determining may comprise a scanned laser illumination source, one or more cameras and/or a structured light source. Moreover, such a system for delivering lasers to an eye and/or for obtaining stereo images of the eye comprising, a first laser for therapeutic purposes, i.e. a therapeutic laser, focusing optics, a camera, a second laser, serving as a laser illumination source, i.e., an illumination laser, and, a scanner optically associated with the first and second lasers and the camera; wherein the scanner has the capability to provide stereo pairs of images of the eye and deliver a laser beam from the first laser to the eye and deliver a laser beam from the second laser to the eye, is further provided.

There is further provided a system for delivering a laser to an eye and for determining the position of the eye comprising a patient support, a laser, optics for delivering a laser beam, a control system for delivering the laser beam to the lens of the eye in a particular pattern, a lens position determination apparatus, and, a laser patient interface.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

BRIEF DESCRIPTION OF THE DRAWINGS

FIGS. 7A, 78 and 7C are diagrams representing posterior, side and anterior elevation views, respectively of the geometry used for the development of laser shot patterns based upon the structure of the an adult nucleus (12 suture branch).

DETAILED DESCRIPTION OF THE DRAWINGS AND THE PREFERRED EMBODIMENTS

Figure 2:
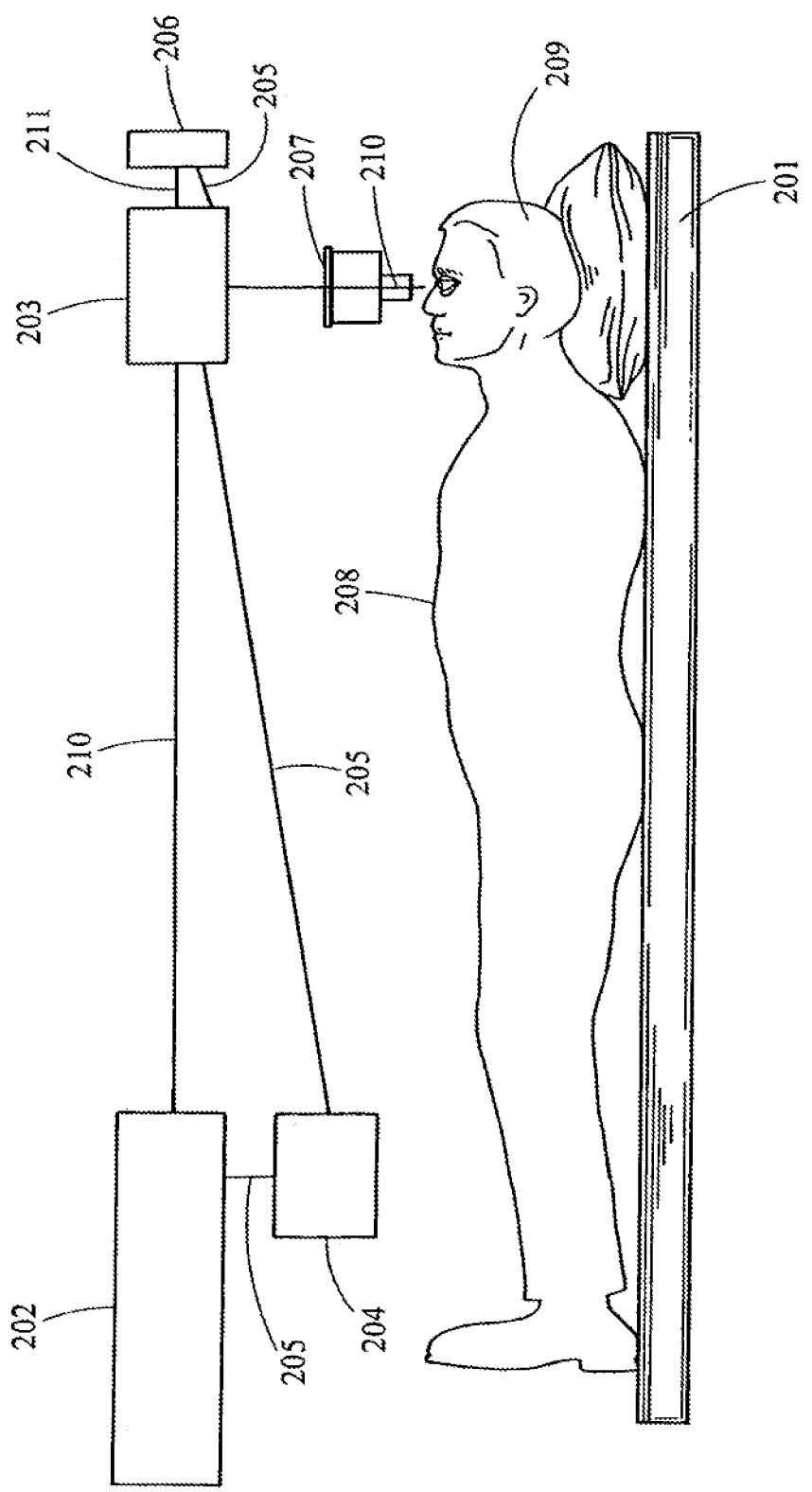
FIG. 2 is a block schematic diagram of a type of system for delivering a laser beam shot pattern to the lens of an eye according to the teachings of the present invention.

In general, the present invention provides a system and method for increasing the amplitude of accommodation and/or changing the refractive power and/or enabling the removal of the clear or cataractous lens material of a natural crystalline lens. Thus, as generally shown in FIG. 2 there is provided a system for delivering a laser beam shot pattern to the lens of an eye comprising: a patient support 201; a laser 202; optics for delivering the laser beam 203; a control system for delivering the laser beam to the lens in a particular pattern 204, which control system 204 is associated with and/or interfaces with the other components of the system as represented by lines 205; a means for determining the position of lens with respect to the laser 206, which means 206 receives an image 211 of the lens of the eye; and a laser patient interface 207.

The patient support 201 positions the patent's body 208 and head 209 to interface with the optics for delivering the laser beam 203.

In general, the laser 202 should provide a beam 210 that is of a wavelength that transmits through the cornea, aqueous and lens. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser. In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers would include: the Delmar Photonics Inc. Trestles-20, which is a Titanium Sapphire (Ti:Sapphire) oscillator having a wavelength range of 780 to 840 nm, less than a 20 femtosecond pulse width, about 100 MHz PRF, with 2.5 nanojoules; the Clark CPA-2161, which is an amplified Ti:Sapphire having a wavelength of 775 nm, less than a 150 femtosecond pulse width, about 3 KHz PRF, with 850 microjoules; the IMRA FCPA (fiber chirped pulse amplification) µJewel D series D-400-HR, which is a Yb:fiber oscillator/amplifier having a wavelength of 1045 nm, less than a 1 picosecond pulse width, about 5 MHz PRF, with 100 nanojoules; the Lumera Staccato, which is a Nd:YVO4 having a wavelength of 1064 nm, about 10 picosecond pulse width, about 100 KHz PRF, with 100 microjoules; and, the Lumera Rapid, which is a ND:YVO4 having a wavelength of 1064 nm, about 10 picosecond pulse width, and can include one or more amplifiers to achieve approximately 2.5 to 10 watts average power at a PRF of between 25 kHz to 650 kHz and also includes a multi-pulsing capability that can gate two separate 50 MHz pulse trains. and, the IMRA FCPA (fiber chirped pulse amplification) µJewel D series D-400-NC, which is a Yb:fiber oscillator/amplifier having a wavelength of 1045 nm, less than a 100 picosecond pulse width, about 200 KHz PRF, with 4 microjoules. Thus, these and other similar lasers may be used a therapeutic lasers.

In general, the optics for delivering the laser beam 203 to the natural lens of the eye should be capable of providing a series of shots to the natural lens in a precise and predetermined pattern in the x, y and z dimension. The optics should also provide a predetermined beam spot size to cause photodisruption with the laser energy reaching the natural lens. Thus, the optics may include, without limitation: an x y scanner; a z focusing device; and, focusing optics. The focusing optics may be conventional focusing optics, and/or flat field optics and/or telecentric optics, each having corresponding computer controlled focusing, such that calibration in x, y, z dimensions is achieved. For example, an x y scanner may be a pair of closed loop galvanometers with position detector feedback. Examples of such x y scanners would be the Cambridge Technology Inc. Model 6450, the SCANLAB hurrySCAN and the AGRES Rhino Scanner. Examples of such z focusing devices would be the Phsyik International Peizo focus unit Model ESee Z focus control and the SCANLAB varrioSCAN.

In general, the control system for delivering the laser beam 204 may be any computer, controller, and/or software hardware combination that is capable of selecting and controlling x y z scanning parameters and laser firing. These components may typically be associated at least in part with circuit boards that interface to the x y scanner, the z focusing device and/or the laser. The control system may also, but does not necessarily, have the further capabilities of controlling the other components of the system as well as maintaining data, obtaining data and performing calculations. Thus, the control system may contain the programs that direct the laser through one or more laser shot patterns.

In general, the means for determining the position of the lens with respect to the laser 206 should be capable of determining the relative distance with respect to the laser and portions of the lens, which distance is maintained constant by the patient interface 207. Thus, this component will provide the ability to determine the position of the lens with respect to the scanning coordinates in all three dimensions. This may be accomplished by several methods and apparatus. For example, x y centration of the lens may be accomplished by observing the lens through a co-boresighed camera system and display or by using direct view optics and then manually positioning the patients' eye to a known center. The z position may then be determined by a range measurement device utilizing optical triangulation or laser and ccd system, such as the Micro-Epsilon opto NCDT 1401 laser sensor and/or the Aculux Laser Ranger LR2-22. The use of a 3-dimensional viewing and measurement apparatus may also be used to determine the x, y and z positions of the lens. For example, the Hawk 3 axis non-contact measurement system from Vision Engineering could be used to make these determinations. Yet a further example of an apparatus that can be used to determine the position of the lens is a 3-dimension measurement apparatus. This apparatus would comprise a camera, which can view a reference and the natural lens, and would also include a light source to illuminate the natural lens. Such light source could be a structured light source, such as for example a slit illumination designed to generate 3-dimensional information based upon geometry.

A further component of the system is the laser patient interface 207. This interface should provide that the x, y, z position between the natural lens and the laser remains fixed during the procedure, which includes both the measurement steps of determining the x y z position and the delivery step of delivering the laser to the lens in a shot pattern. The interface device may contain an optically transparent applanator. One example of this interface is a suction ring applanator that is fixed against the outer surface of the eye and is then positioned against the laser optical housing, thus fixing the distance between the laser, the eye and the natural lens. Reference marks for the 3-dimensional viewing and measuring apparatus may also be placed on this applanator. Moreover, the interface between the lower surface of the applanator and the cornea may be observable and such observation may function as a reference. A further example of a laser patient interface is a device having a lower ring, which has suction capability for affixing the interface to the eye. The interface further has a flat bottom, which presses against the eye flattening the eye's shape. This flat bottom is constructed of material that transmits the laser beam and also preferably, although not necessarily, transmits optical images of the eye within the visible light spectrum. The upper ring has a structure for engaging with the housing for the laser optics and/or some structure that is of known distance from the laser along the path of the laser beam and fixed with respect to the laser. Further examples of such devices are generally disclosed in US D462442, US D462443, and US D459807S, the disclosures of which are hereby incorporated by reference. As an alternative to an applanator, the interface may be a corneal shaped transparent element whereby the cornea is put into direct contact with the interface or contains an interface fluid between.

Figure 2A:
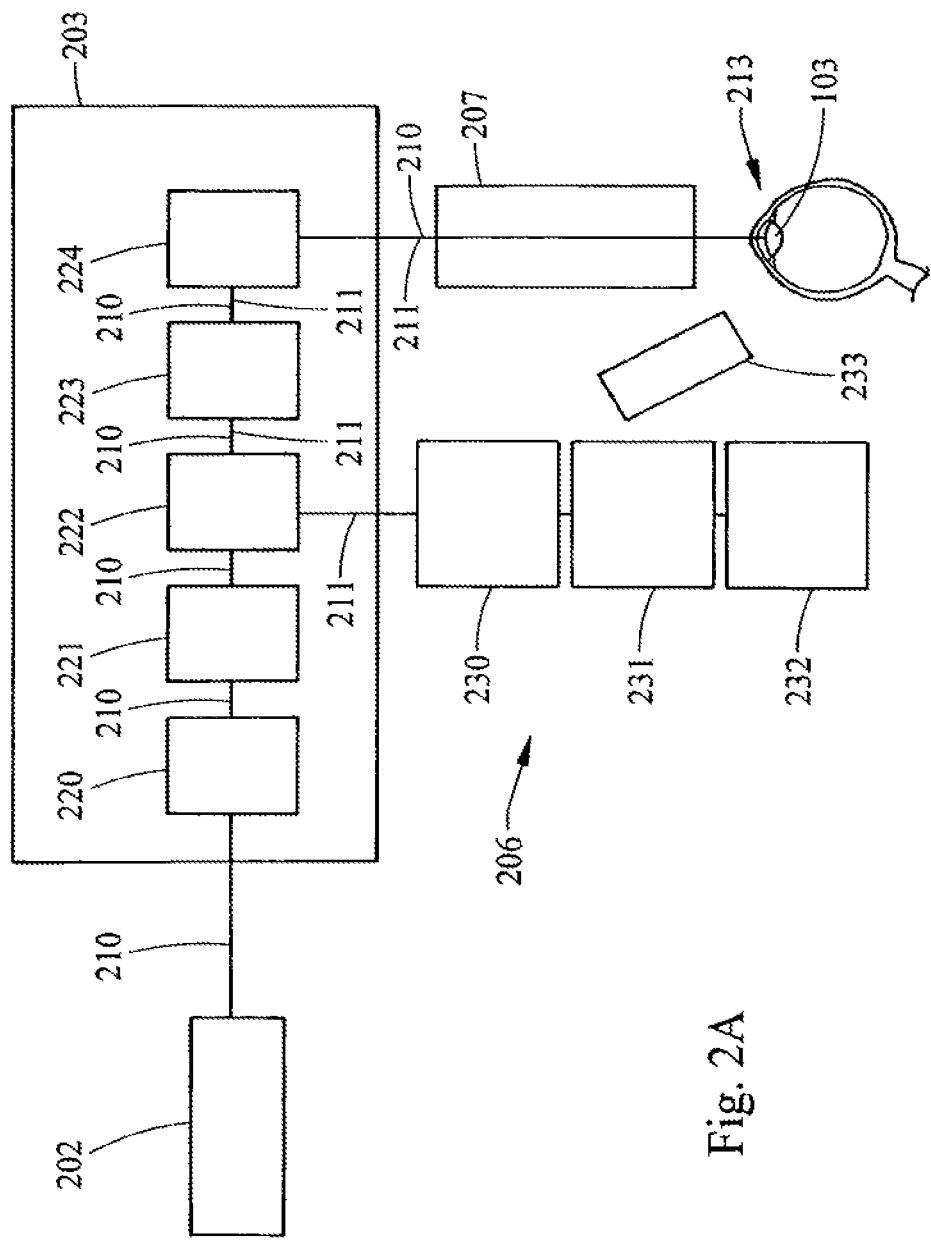
FIG. 2A is a block schematic diagram of illustrative components forming a portion of a system for delivering a laser beam shot pattern to the lens of an eye according to the teachings of the present invention.

An illustrative combination utilizing by way of example specific optics for delivering the laser beam 203 and means for determining the position of the lens 206, is shown in part, in FIG. 2A. FIG. 2A is a more detailed schematic diagram of a configuration of the system of FIG. 2. Thus, the example of FIG. 2A provides a laser 202, laser optics for delivering the laser beam 203, which optics comprise a beam expander telescope 220, a z focus mechanism 221, a beam combiner 222, an x y scanner 223, and focusing optics 224. There is further provided in FIG. 2A relay optics 230, camera optics 231, which may also include a zoom, and a ccd camera 232, which components form a part of a three-dimensional viewing and measuring apparatus. Moreover, these components 231 and 232 in combination with a light source 233, and the scanner 223 are the means for determining the position of the lens 206.

This combination of FIG. 2A utilizes the x y scanner 223 to create stereoscopic images of the lens with only a single ccd camera 232. Optical images 211 of the eye 213 and in particular optical images of the natural lens 103 of the eye 213 are conveyed along a path 211. This path 211 follows the same path as the laser beam 210 from the natural lens 103 through the laser patient interface 207, the focusing optics 224, the x y scanner 223 and the beam combiner 222. This combination of FIG. 2A further comprises: a laser patient interface 207, and a light source 233, which could be for example uniform illumination, or a slit illumination or other structured light source designed to enhance 3-dimensional accuracy. The light source, in part, provides illumination of the natural lens of the patient's eye for the purposes of determining the 3-dimensional position of the lens. Thus, either stereoscopic images and/or the information from the camera are sent to a controller and/or computer (not shown in FIG. 2A) for further processing and use in determining 3-dimensional positions of the lens. Stereo images may be generated by commanding the scanner to go to and pause at a nominal left position and then electronically trigger the camera and controller to capture and store the left image; then command the scanner/camera/controller similarly to capture and store a right image. This sequence may be repeated in a periodic manner. These left and right images can be processed by the controller to generate the position and shape of the lens. The left and right images can be displayed using a stereo video monitor. Camera images or stereo images may also be used to measure suture geometry and orientation in the patients lens, which can be used to determine the parameters of suture based shot patterns and to align suture based shot patterns to the patients lens suture geometry and orientation. The combination illustrated in FIG. 2A provides 3-dimensional information that can be used to determine the shape of the lens, including the anterior and posterior surfaces thereof. This information can also be used to visualize the structure of the lens, including sutures. Moreover, the information about the lens obtained from the combination of FIG. 2A can further be used in determining the laser shot pattern and laser shot placement with respect to lens shape and/or structure.

FIGS. 2 and 2A-2E are block schematic diagrams and thus the relative positions and spacing of the components illustrated therein are by way of example. Accordingly, the relative placements of these components with respect to one another may be varied and all or some of their functions and components may be combined.

FIGS. 2B-2E are further more detailed embodiments of a portion of the system of FIG. 2. To the extent that like numbers are used in these Figures and in FIGS. 2 and 2A they have the same meaning. Thus, FIGS. 2B-2E provide further examples and combinations of optics for delivering the laser beam 203 and means for determining the position of the lens 206.

Figure 2B:
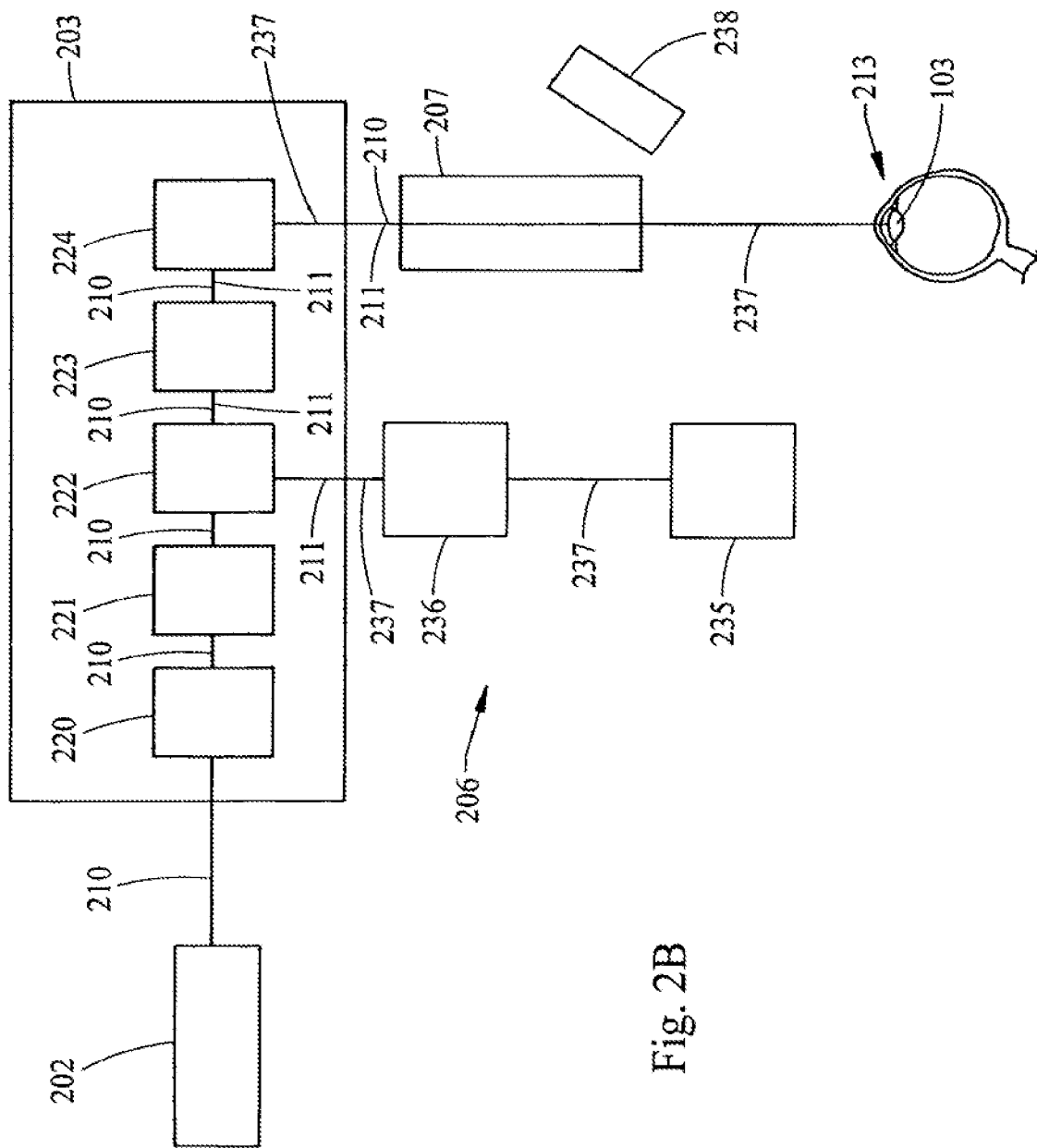
FIG. 2B is a block schematic diagram of illustrative components forming a portion of a system for delivering a laser beam shot pattern to the lens of an eye according to the teachings of the present invention.

FIG. 2B is a block schematic diagram of a portion of a system having a means for determining the position of the lens 206, which employs a scanned laser illumination source. Thus, there is provided a laser illumination source 235, a beam expander and focusing optics 236, an illumination laser path 237 and a camera 238 for viewing the lens 103 as illuminated by the laser illumination source. Component 235 in combination with the scanner 223 and camera 238 are the means for detecting the position of the lens 206.

The laser illumination source 235 can be any visible or near infrared laser diode, preferably with a short coherence length for reduced speckle. For example, the laser can be a Schafter+Kirchhoff Laser (90CM-M60-780-5-Y03-C-6) or can also be obtained from StockerYale and may also come with focusing optics. In operation, x y scanner 223 scans the beam from the illumination laser 235 into the focusing optics 224, through the patient interface 207 and onto the lens 103. Thus, the beam from the illumination laser 235 follows the illumination laser path 237. The beam expander focusing optics 236 combined with focusing optics 224 provide a high F number, slow focusing beam with long depth of field. The depth of field is approximately equal to the path length of the laser illumination beam through the lens 103. Thus, producing small and approximately equal sized spots at the anterior and posterior of lens 103. The illumination laser beam is scanned, predominately in one axis, in a line at a rate sufficiently fast compared to the camera 238 exposure time such that the scanned illumination laser beam acts like a slit illumination source during the exposure time. On subsequent exposures or frames of the camera 238, the illumination laser beam is scanned to different positions, thus, illuminating the entire lens over time. This can occur as a series of y scanned lines with different x positions exposures or the lines can be radially scanned with each exposure at a different angle. From the analysis of the data from all of these images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2C:
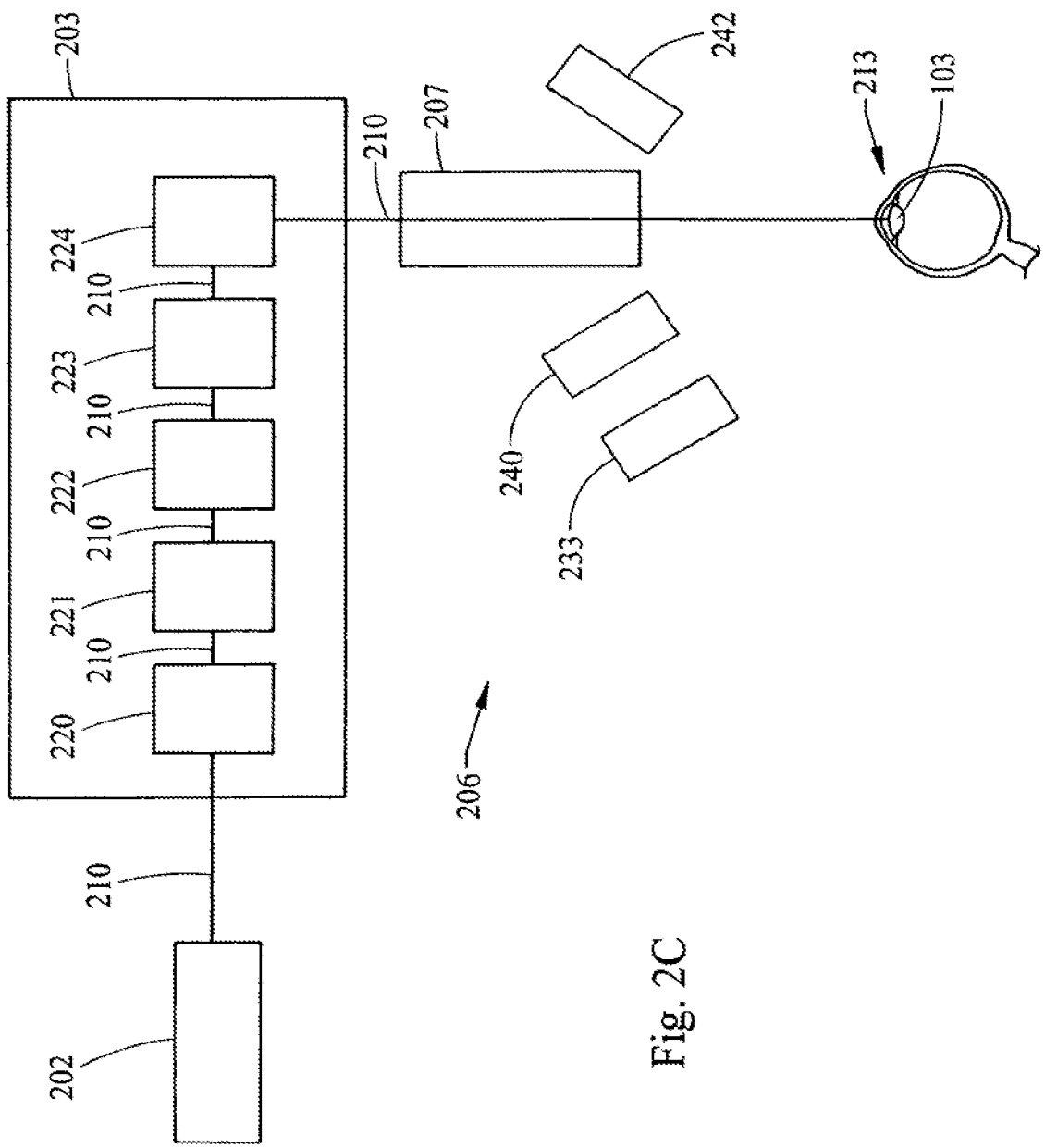
FIG. 2C is a block schematic diagram of illustrative components forming a portion of a system for delivering a laser beam shot pattern to the lens of an eye according to the teachings of the present invention.

FIG. 2C is a block schematic diagram of a portion of a system having a means for detecting the position of the lens 206, which employs dual cameras. Thus, there is provided a left camera 241 and a right camera 242. Components 241, 242 and 233 are the means for detecting the position of the lens 206.

The system of FIG. 2C utilizes two camera stereo viewing technology for providing patient care capability and for obtaining images and data for determining lens position and/or shape. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2D:
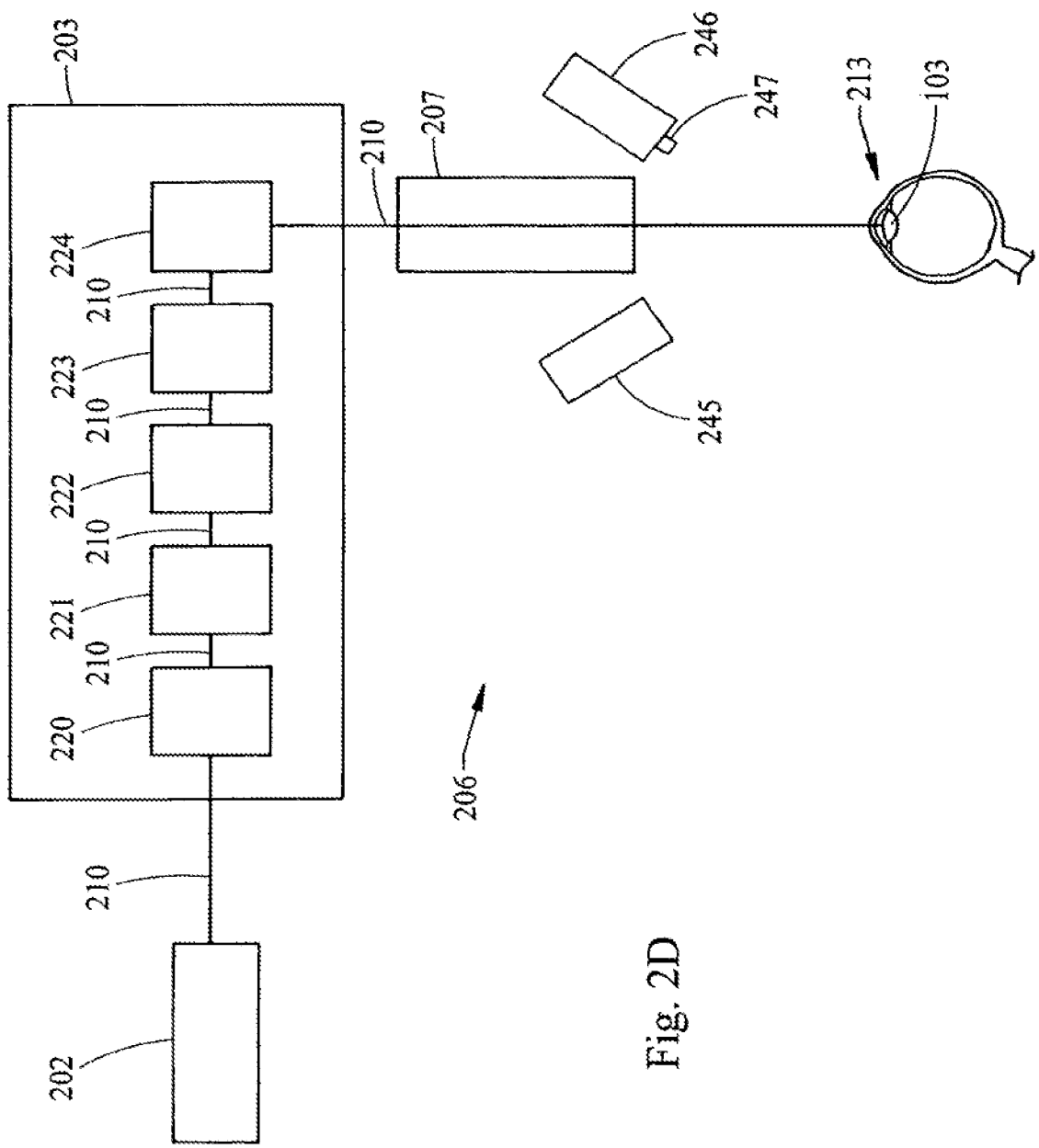
FIG. 2D is a block schematic diagram of illustrative components forming a portion of a system for delivering a laser beam shot pattern to the lens of an eye according to the teachings of the present invention.

FIG. 2D is a block schematic diagram of a portion of a system having a means for detecting the position of the lens 206, which employs structured illumination. Thus, there is provided a structured light source 245 and a camera 246, having a lens 247, for viewing the structured light source. Components 245 and 246 in combination are a means for detecting the position of the lens 206.

The system of FIG. 2D utilizes a structured tight source and a camera to provide patient care capability and for obtaining images and data for determining lens position and/or shape. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2E:
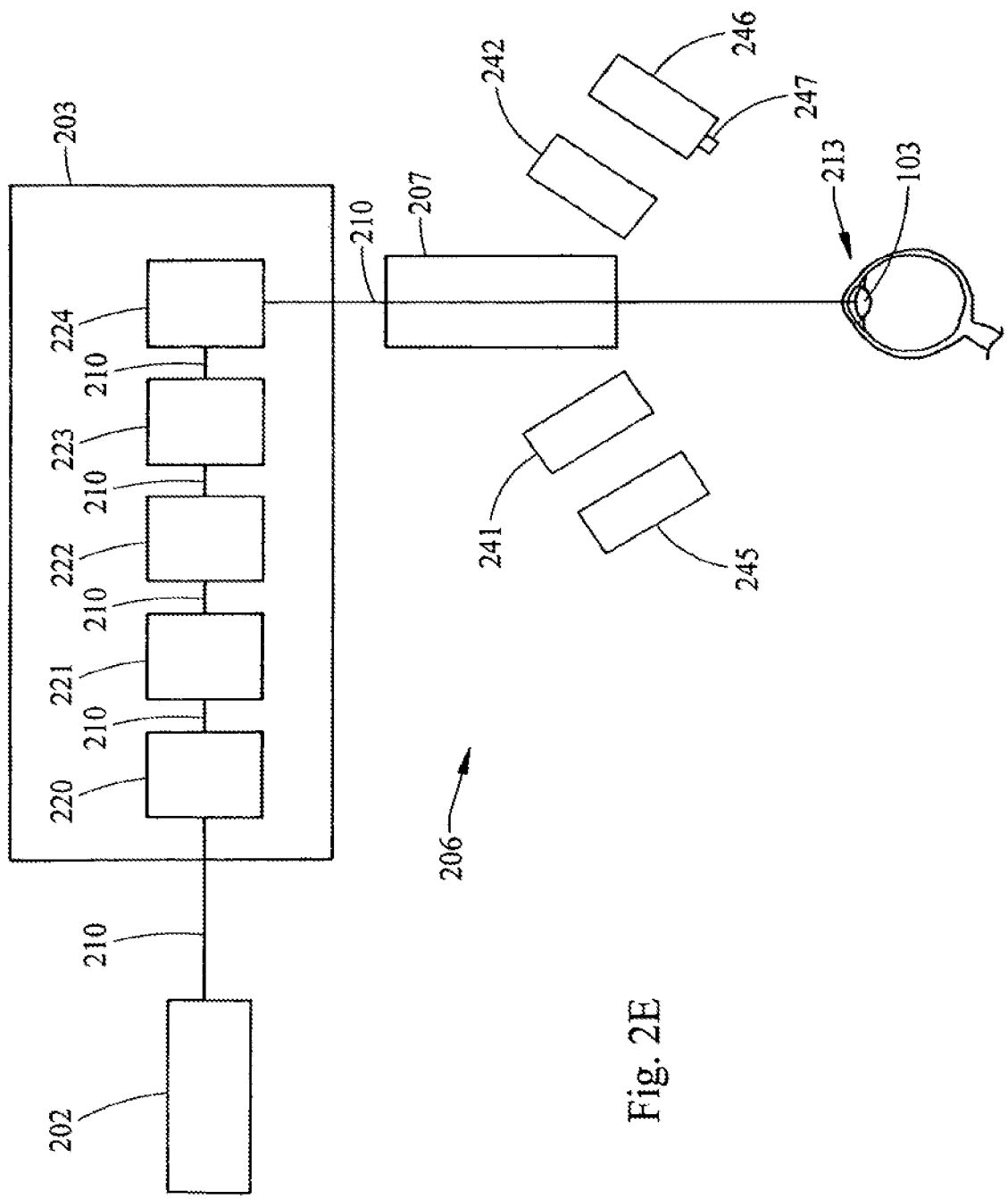
FIG. 2E is a block schematic diagram of illustrative components forming a portion of a system for delivering a laser beam shot pattern to the lens of an eye according to the teachings of the present invention.

FIG. 2E is a block schematic diagram of a portion of a system having a means for detecting the position of the lens 206, which employs structured illumination and dual cameras. Thus, there is provided a structured light source 245, a camera 246 for viewing the structured light source, a lens 247 for camera 246, a left camera 241 and a right camera 242. Components 245 and 246, in combination are the means for detecting the position of the lens 206. Components 241 and 242, in combination are a means for providing patient care, including monitoring capability. This combination 241, 242 may also provide information and/or data to determine the position of the lens.

The combination of components in the system illustrated in FIG. 2E provides the ability to optimize the accuracy of determining the position of the lens, while also providing the ability to separately and/or independently optimize patient care. Patient care includes, but is not limited to, visualization of the eye and its surrounding area, procedures such as attaching a suction ring, applying ophthalmic drops, utilizing instruments, and positioning the patient for surgery. In one embodiment the structured light source 245 may be a slit illumination having focusing and structured light projection optics, such as a Schafter+Kirchhoff Laser Macro Line Generator Model 13LTM+90CM, (Type 13LTM-250S-41+90CM-M60-780-5-Y03-C-6) or a StockerYale Model SNF-501L-660-20-5. In this embodiment the structured illumination source 245 also includes scanning means. Another embodiment of the structured light source 245, may be a stationary grid pattern projected on the lens. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

When using a scanned slit illumination the operation includes positioning the slit on one side of the lens, taking an image then moving the slit approximately one slit width, then taking another image, and then repeating this sequence until the entire lens is observed. For example, a 100 µm slit width can scan a nominal 9 mm dilated pupil diameter in 90 images, which takes approximately 3 seconds using a 30 Hz frame rate camera. To obtain images of the anterior and posterior surface in a single image without overlap, the slit should be at an angle to the AP axis, i.e., it should not be parallel to that axis. The nominal slit angle can be approximately 15 to 30 degrees from the AP axis. Any visible or near IR wavelength source within the sensitivity of the camera may be used. Low coherence length sources are preferable to reduce speckle noise.

Another embodiment for the structured light illumination sub-system shown in FIG. 2E is to arrange the structured light illumination source 245, the structured light camera 246 and the lens for the structured light camera 247 in the so-called Scheimpflug configuration which is well-known. In Summary, the Scheimpflug condition states that given an object, a lens and an image, that the object plane is imaged sharply in the image plane if the object plane, the lens plane and the image plane intersect in the same line. The structured light source 245 projects a line and or a plurality of lines onto the eye lens 103 at an angle or plurality of angles. The light scattered at the eye lens 103 forms the object to be imaged by the lens 247 and focused onto the camera system 246. Since the slit illuminated image in the eye lens 103 may be at a large angle with respect to the camera lens 247 and camera 246, this presents a large depth of field to the camera and the entire slit image may not be in sharp focus at the camera. By tilting the camera lens and the camera at an angle or plurality of angles such that Scheimpflug's condition is met, the image along the illuminated plane can be in sharp focus. Alternately, the camera and/or lens may be tilted such that the angle between the slit illuminated image plane and the camera focal plane is reduced, improving the dept-of-focus sharpness, however may not meet the Scheimpflug condition. Such configurations can improve sharpness further by reducing the aperture of the optical path, thereby increasing the F# of the system. These angles will depend on the angle the slit beam makes with the eye. This will increase the depth of field at the object, the scattered light from the slit illuminator, and allow it to imaged through the lens onto the camera image plane and remain in focus for the entire depth of the object.

There is further provided the use of a structured light illuminating and receiving system, such as for example slit illumination, which in addition to measuring the position and shape of anterior and posterior lens surfaces in three dimensions, can be used as a screening tool for determining a candidate patient's suitability for laser lens surgery. Thus, light from a structured light system is directed toward the subject lens. The amplitude of the received scattered light distributed throughout the lens is then evaluated to detect scattering regions that are above threshold, which is a level of scattering that would interfere with the laser surgery. Thus, the detection of lens scattering malformations that could interfere with, or reduce the efficacy of a procedure can be detected and evaluated. Such scattering malformations of the lens would include, without limitation, cataractous, pre-cataractous and non-cataractous tissue. Such scattering malformations, may be located throughout the lens, or may be restricted to specific regions of the lens. For example the systems of FIGS. 2A-2E in cooperation with a controller and/or processor may function as such a structured light illuminating and receiving system.

The structured light illuminating and receiving system may be contained within the surgical laser system or it may be a separate unit for evaluating the suitability of a candidate patient for laser lens surgery. Commercially available examples of such structured light illuminating and receiving systems are the Ziemer Ophthalmic Systems GALILEI Dual Scheimpflug Analyzer and the Oculus, Inc. PENTACAM. It is believed that these systems cannot be used to determine the position of the lens with respect to the treatment laser. However, lens shape data from these systems may be obtained and then used in conjunction with position data provided by systems such as the systems of FIGS. 2A-2E.

By suitability, it is meant that laser lens surgery may be indicated or contra-indicated for a particular patient's lens. In addition, it is also meant that certain shot patterns, and/or combinations and placement of shot patterns may be indicated or contra-indicated, depending upon the location of the malformations, the shot patterns, the placement of the shot patterns and the intended effect of the shot pattern. Malformations that would substantially interfere with the desired effect of a laser shot pattern would make that laser shot pattern contra-indicated. Thus, for example, for a patient with a posterior scattering malformation, laser surgery in the anterior of that particular lens would be indicated, for example a pattern such as that shown in FIG. 20, while laser surgery in the posterior would be contra-indicated, such as the patterns shown in FIG. 21.

Figure 1:
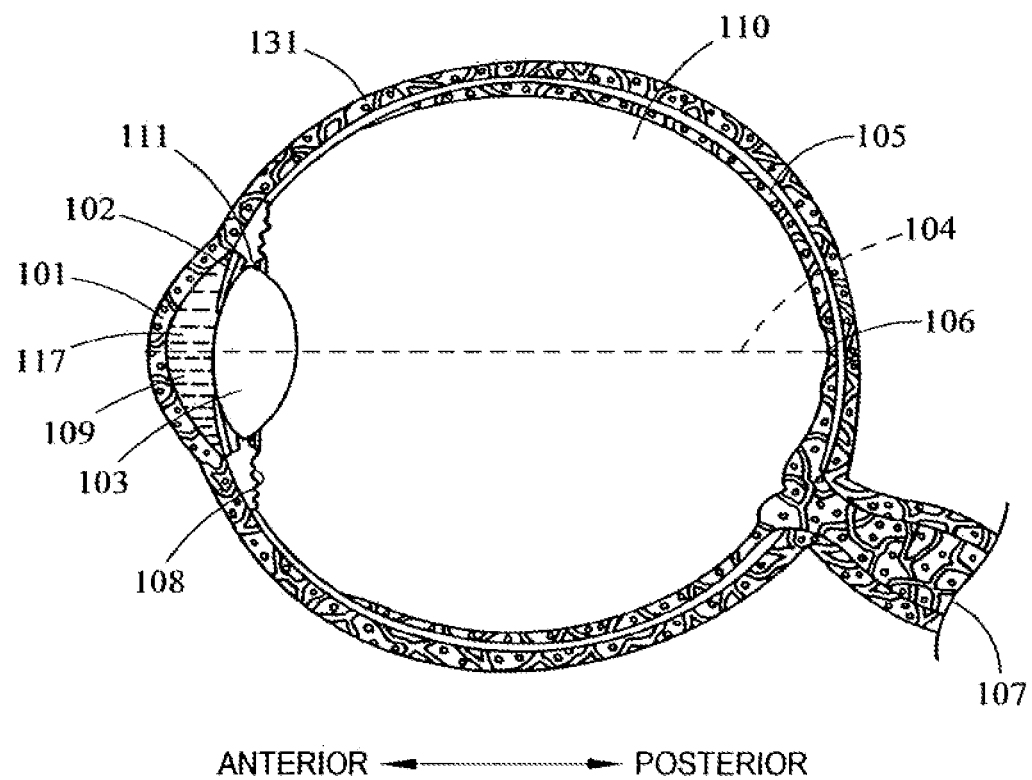
FIGS. 1 and 1A are cross sectional representations of the human eye.
Figure 1A:
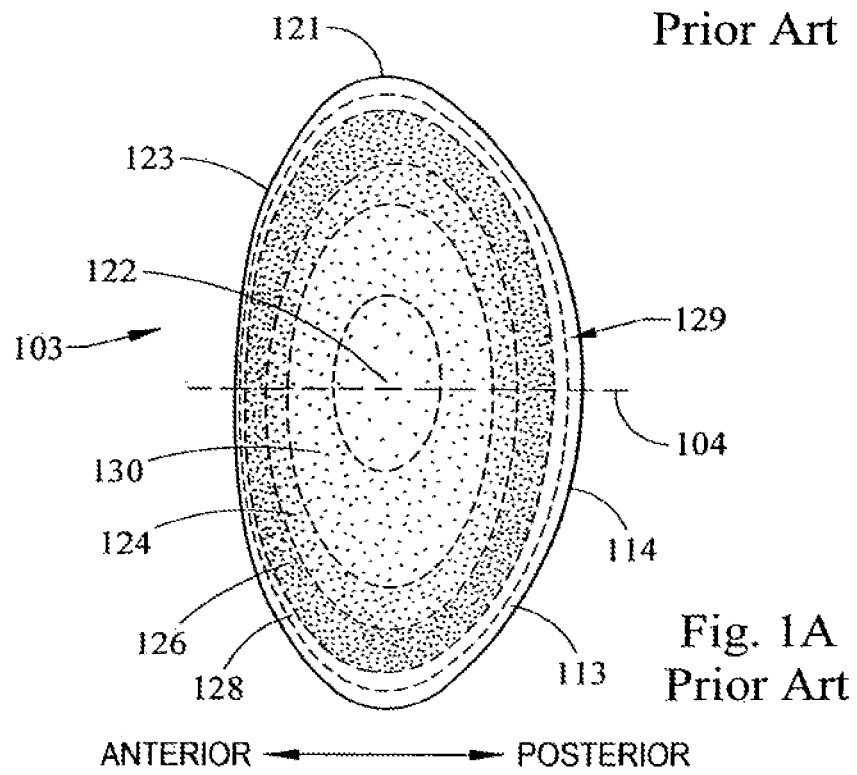

FIGS. 4A-E illustrate the three branched or Y suture geometry in the context of the structures found in the fetal nucleus 415 of the lens. Thus, these figures provide a more detailed view of the structures illustrated as layer 130, which encompasses layer 122 of FIG. 1A. In FIGS. 4A-E the view of the inner layer of the lens is rotated stepwise from the posterior side FIG. 4A to the anterior side FIG. 4E of the lens. Thus, this layer of the lens has three posterior suture lines 401, 402, and 403. This layer also has three anterior suture lines 412, 413 and 414. The anterior suture lines are longer than the posterior suture lines and these lines are staggered when viewed along the anterior to posterior (AP) axis 411. The lens fibers, which form the layers of the nucleus, are shown by lines 404, it being understood that these are only illustrative lines and that in the actual natural layer of the lens there would be many times more fibers present. To aid in illustrating the structure and geometry of this layer of the nucleus representative fibers 405, 406, 407, 408, 409 and 410 have been exaggerated and individually shaded in FIGS. 4A-E. Thus, as the view of the lens nucleus is rotated from posterior to anterior the positions of these representative fibers, there relationship to each other, and there relationship to the suture lines is illustrated.

The length of the suture lines for the anterior side are approximately 75% of the equatorial radius of the layer or shell in which they are found. The length of the suture lines for the posterior side are approximately 85% of the length of the corresponding anterior sutures, i.e, 64% of the equatorial radius of that shell.

The term—essentially follows—as used herein would describe the relationship of the shapes of the outer surface of the lens and the fetal nucleus 415. The fetal nucleus is a biconvex shape. The anterior and posterior sides of the lens have different curvatures, with the anterior being flatter. These curvatures generally follow the curvature of the cortex and the outer layer and general shape of the lens. Thus, the lens can be viewed as a stratified structure consisting of long crescent fiber cells arranged end to end to form essentially concentric or nested shells.

As provided in greater detail in the following paragraphs and by way of the following examples, the present invention utilizes this and the further addressed geometry, structure and positioning of the lens layers, fibers and suture lines to provide laser shot patterns for increasing the accommodative amplitude of the lens. Although not being bound by this theory, it is presently believed that it is the structure, positioning and geometry of the lens and lens fibers, in contrast to the material properties of the lens and lens fibers, that gives rise to loss of accommodative amplitude. Thus, these patterns are designed to alter and affect that structure, positioning and/or geometry to increase accommodative amplitude.

Figure 5A:
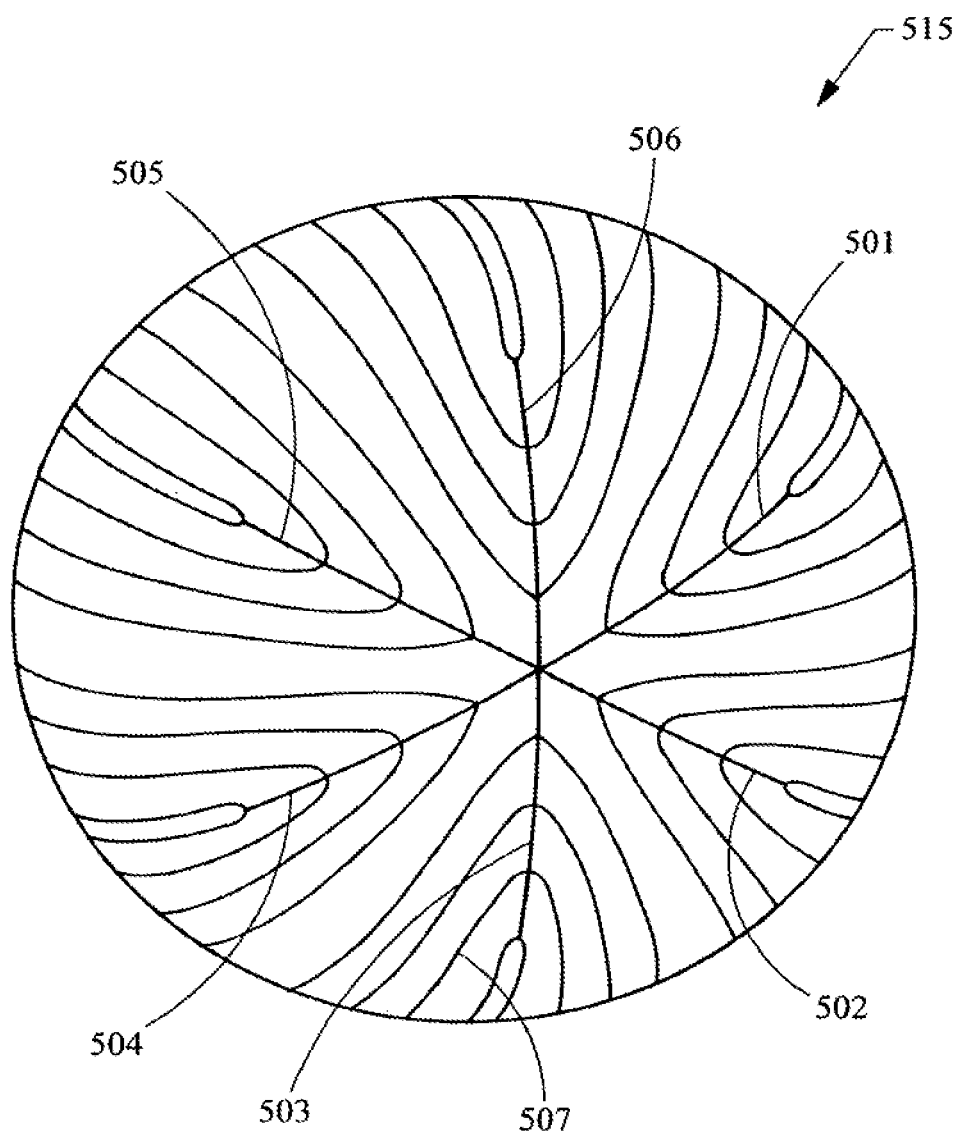
FIGS. 5A, 5B, and 5C are diagrams representing posterior, side and anterior elevation views, respectively, of the geometry used for the development of laser shot patterns based upon the structure of the infantile nucleus (six suture branch nucleus).
Figure 5B:
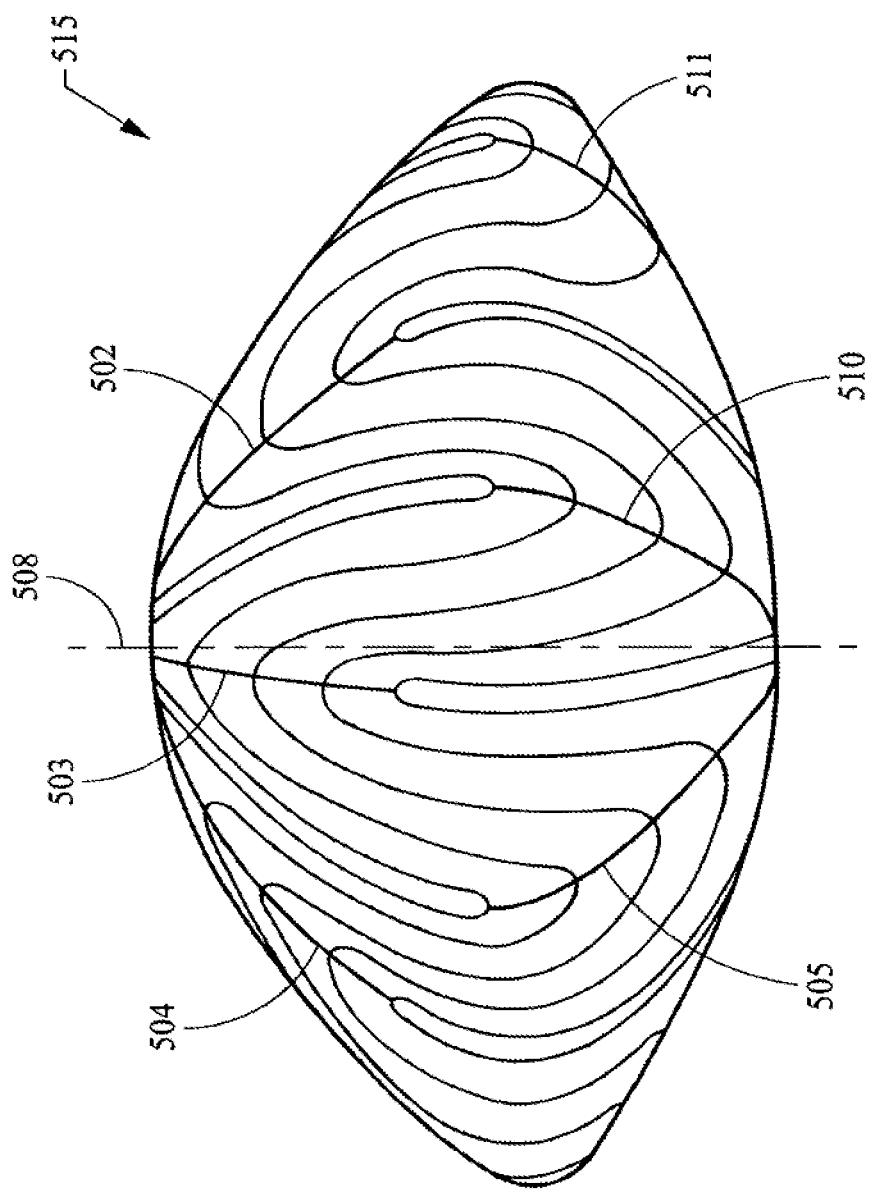
Figure 5C:
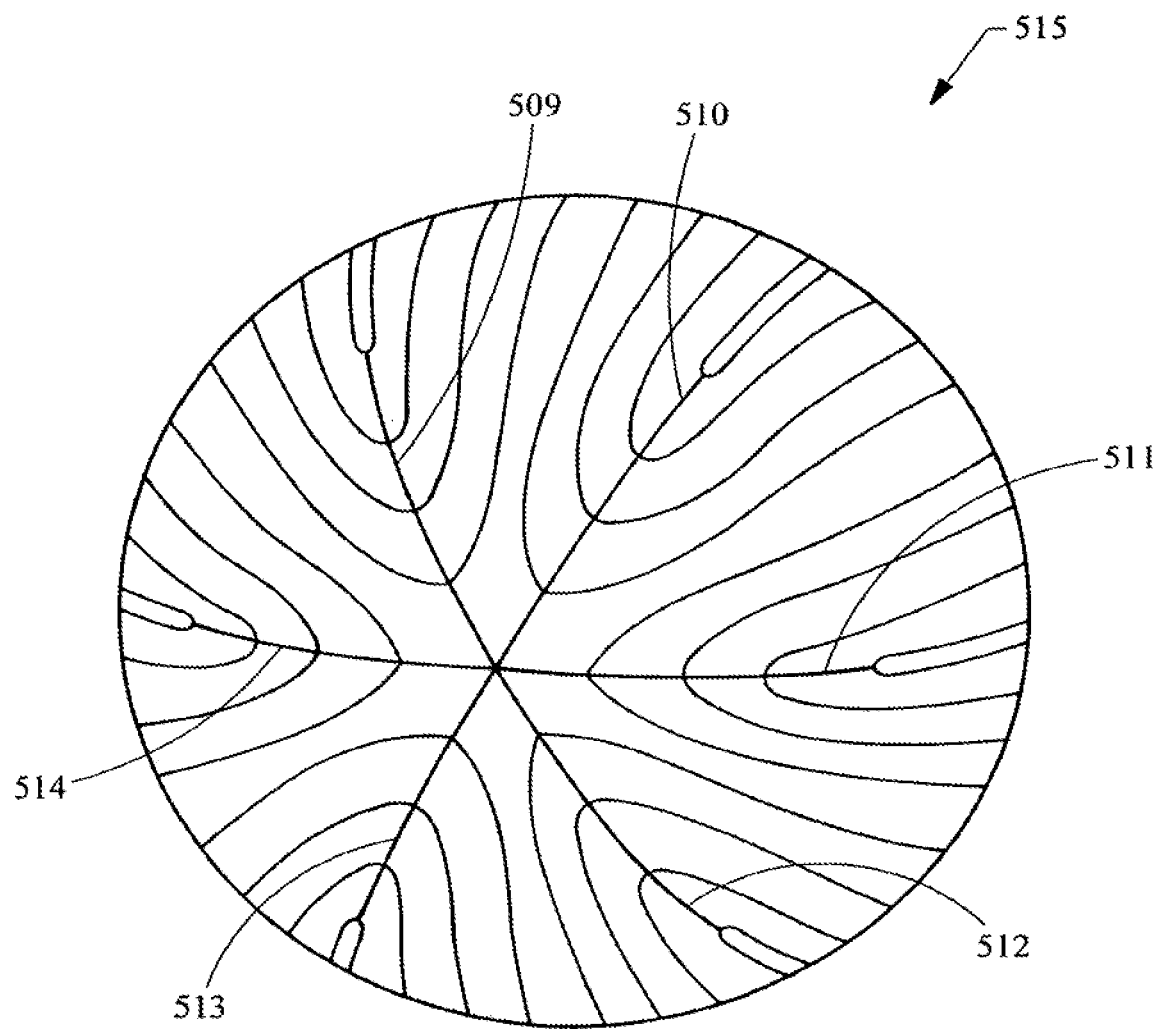

FIGS. 5A-C illustrate the six branched or star suture geometry in the context of the structure found in the infantile layer of the nucleus 515 of the lens. Thus, these figures provide a more detailed view of the structures illustrated as layer 124 of FIG. 1A. In FIGS. 5A-C the view of the layer of the lens is rotated from the posterior side FIG. 5A to a side view FIG. 5B to the anterior side FIG. 5C. Thus, this layer of the nucleus has six posterior suture lines 501, 502, 503, 504, 505, and 506. This layer of the nucleus also has six anterior suture lines 509, 510, 511, 512, 513, and 514. The anterior suture lines are longer than the posterior suture lines and these lines are staggered when viewed along the AP axis 508. The lens fibers, which form the layers of the nucleus, are shown by lines 507, it being understood that these are only illustrative lines and that in the actual natural layer of the lens there would be many times more fibers present.

The shape of the outer surface of the lens essentially follows the infantile nucleus 515, which is a biconvex shape. Thus, the anterior and posterior sides of this layer of the lens have different curvatures, with the anterior being flatter. These curvatures generally follow the curvature of the cortex and the outer layer and general shape of the lens. These curvatures also generally follow the curvature of the fetal nucleus 415. Thus, the lens can be viewed as a stratified structure consisting of long crescent fiber cells arranged end to end to form essentially concentric or nested shells, with the infantile nucleus 515 having the fetal nucleus 415 nested within it. As development continues through adolescence, additional fiber layers grow containing between 6 and 9 sutures.

Figure 6A:
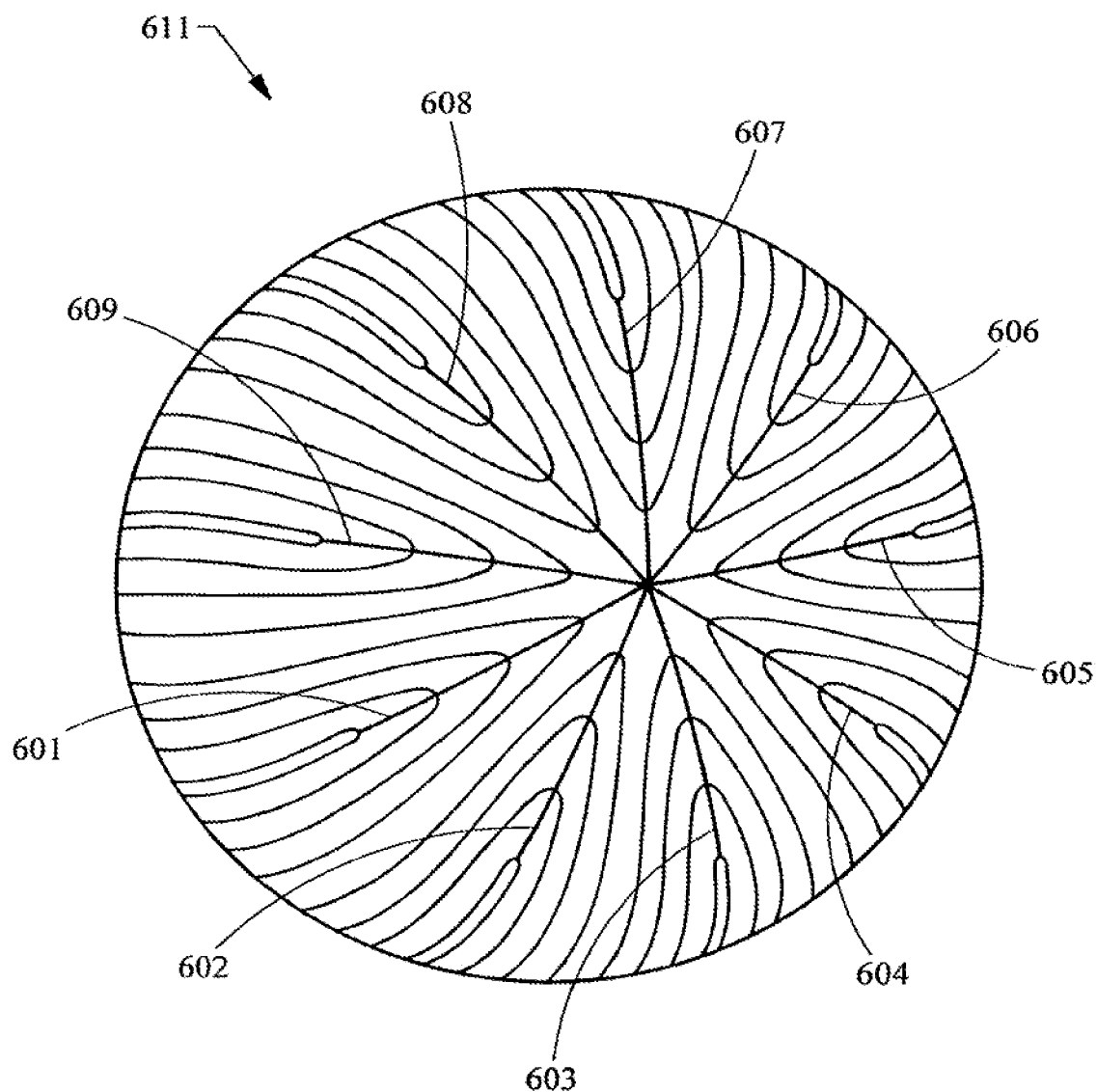
FIGS. 6A, 6B and 6C are diagrams representing posterior, side and anterior elevation views, respectively of the geometry used for the development of laser shot patterns based upon the structure of the adolescent nucleus (nine suture branch nucleus).
Figure 6B:
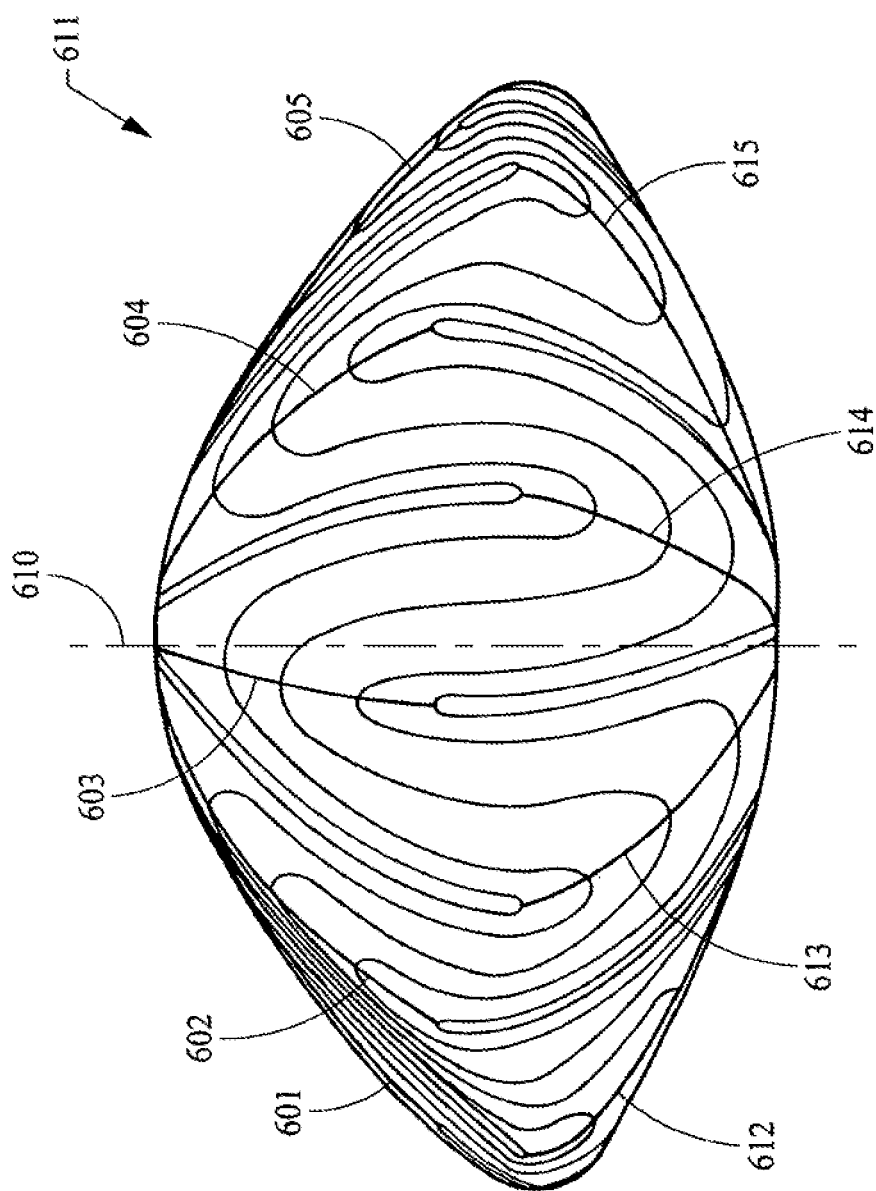
Figure 6C:
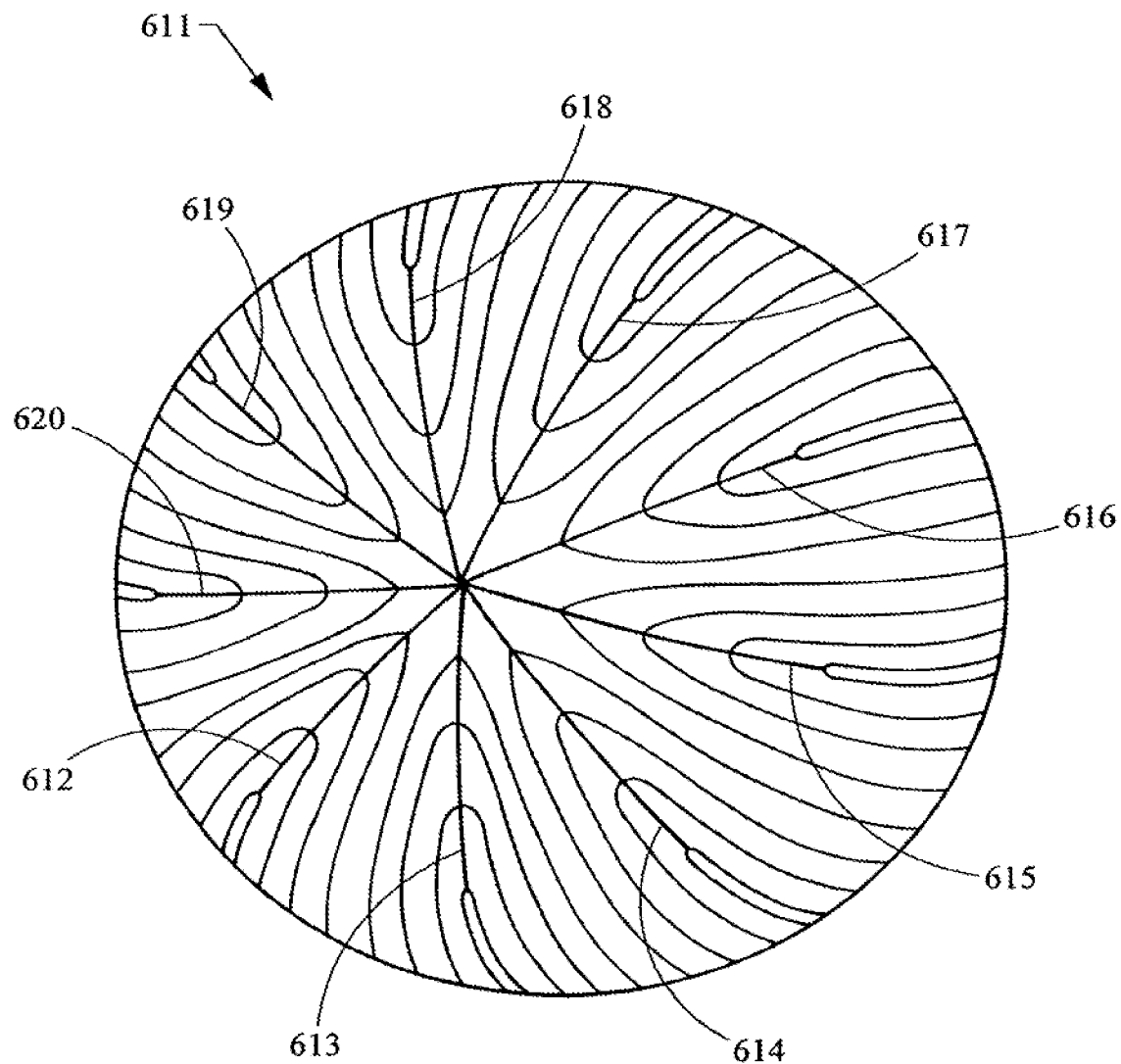

FIGS. 6A-C illustrate the nine branched or star suture geometry in the context of the structure found in the adolescent layer of the nucleus 611 of the lens. Thus, these figures provide a more detailed view of the structures illustrated as layer 126 of FIG. 1A. In FIGS. 6A-C the view of the layer of the lens is rotated from the posterior side FIG. 6A to a side view FIG. 6B to the anterior side FIG. 6C. Thus, this layer of the nucleus has nine posterior suture lines 601, 602, 603, 604, 605, 606, 607, 608 and 609. This layer of the nucleus also has nine anterior suture lines 612, 613, 614, 615, 616, 617, 618, 619 and 620. The anterior suture lines are longer than the posterior suture lines and these lines are staggered when viewed along the AP axis 610. The lens fibers, which form the layers of the nucleus, are shown by lines 621; it being understood that these are only illustrative lines, and that in the actual natural layer of the lens there would be many times more fibers present.

The outer surface of the cornea follows the adolescent nucleus 611, which is a biconvex shape. Thus, the anterior and posterior sides of this layer have different curvatures, with the anterior being flatter. These curvatures generally follow the curvature of the cortex and the outer layer and general shape of the lens. These curvatures also generally follow the curvature of the fetal nucleus 415 and the infantile nucleus 515, which are nested within the adolescent nucleus 611. Thus, the lens can be viewed as a stratified structure consisting of long crescent fiber cells arranged end to end to form essentially concentric or nested shells. As development continues through adulthood, additional fiber layers grow containing between 9 and 12 sutures.

Figure 7A:
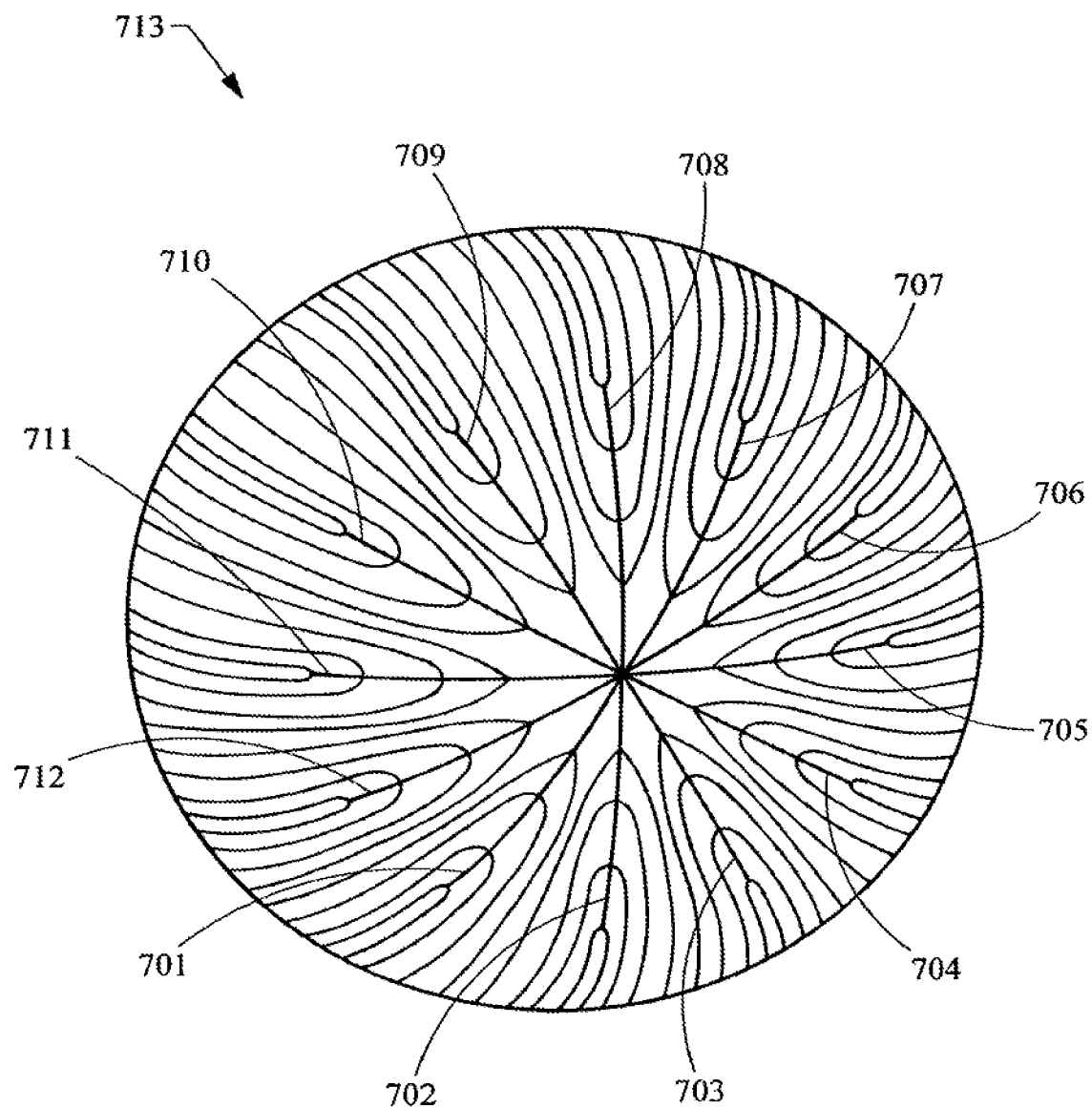
Figure 7B:
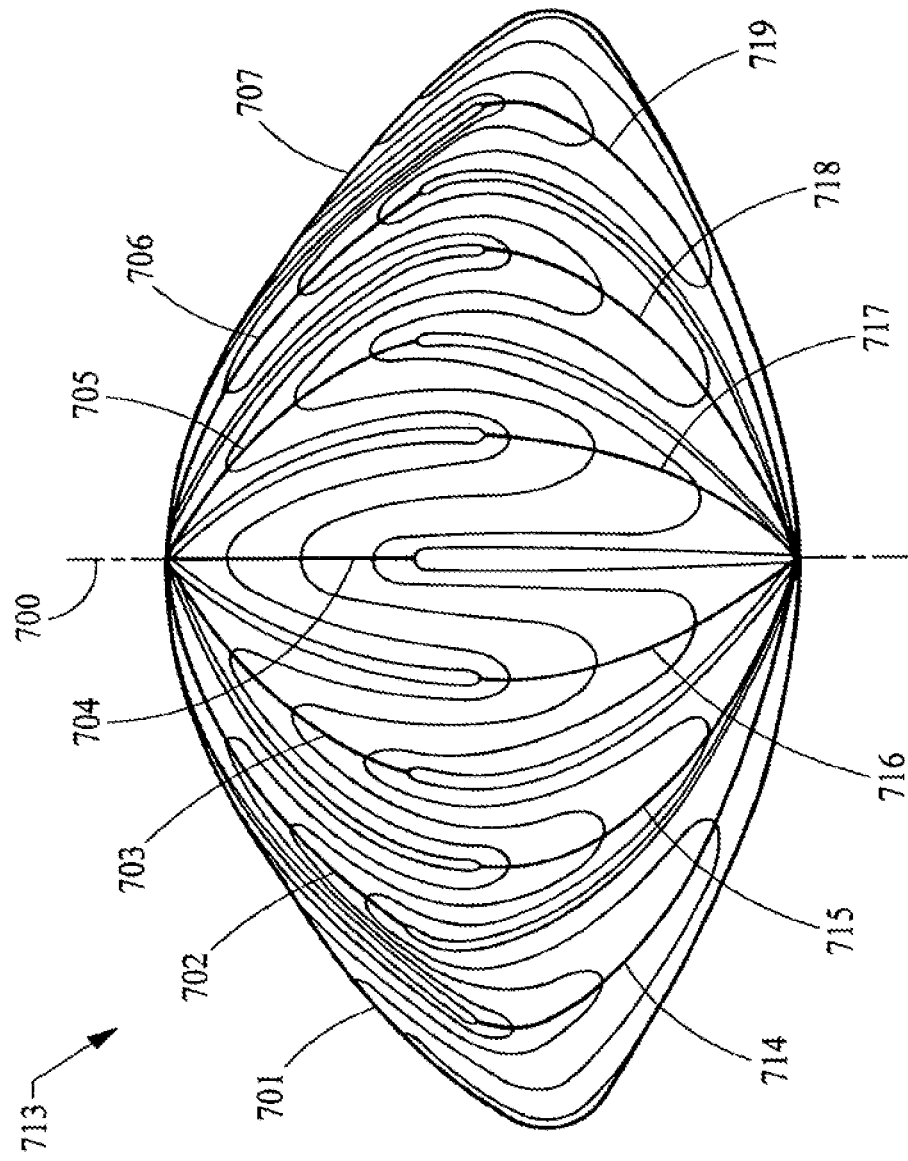
Figure 7C:
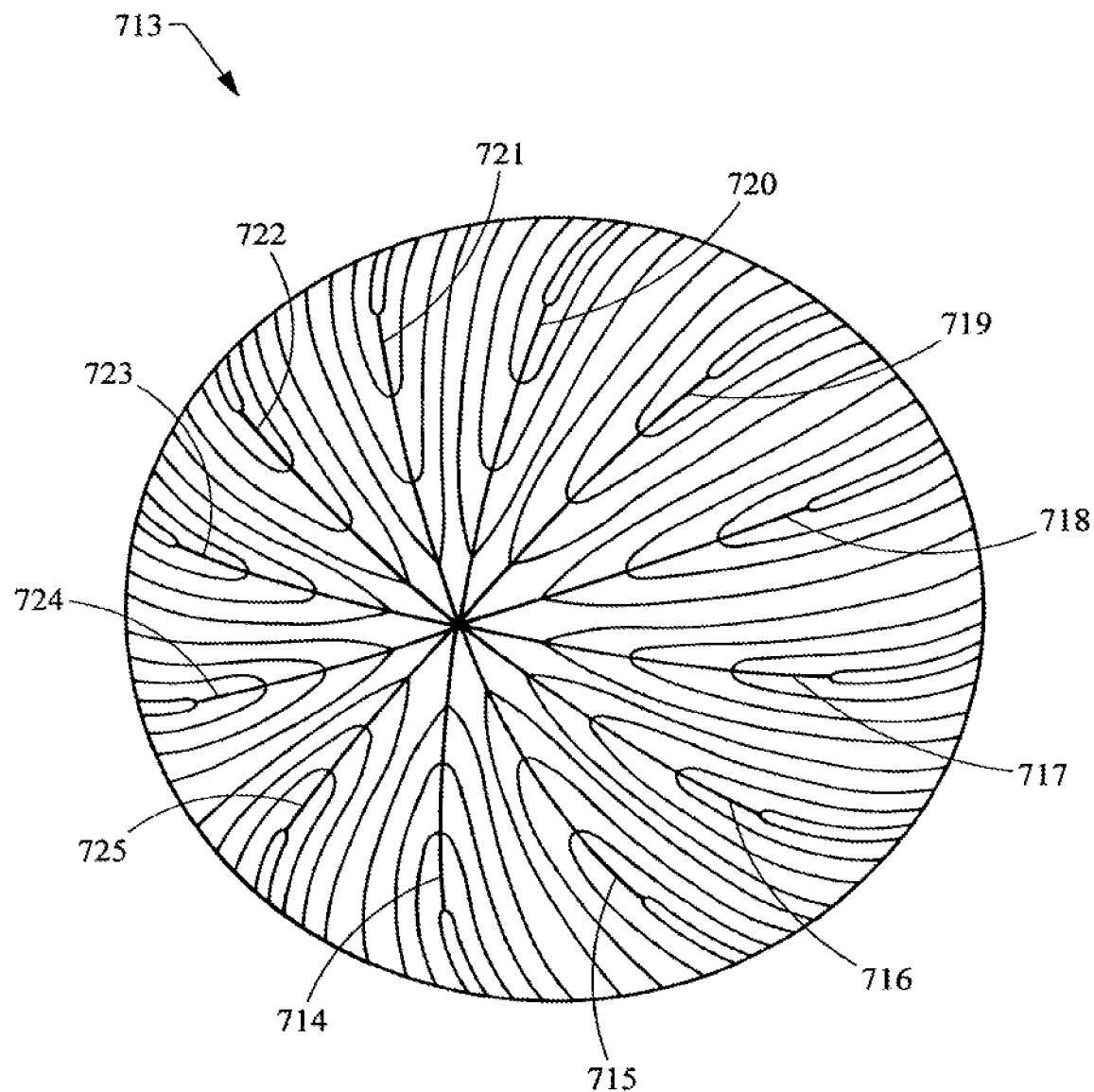

FIGS. 7A-C illustrates the twelve branched or star suture geometry in the context of the structure found in the adult layer of the nucleus 713 of the lens. Thus, these figures provide a more detailed view of the adult layer 128 depicted in FIG. 1A. In FIGS. 7A-C the view of the layer of the lens is rotated from the posterior side FIG. 7A to a side view FIG. 7B to the anterior side FIG. 7C. Thus, the adult layer of the nucleus has twelve posterior suture lines 701, 702, 703, 704, 705, 706, 707, 708, 709, 710, 711, and 712. This layer of the nucleus also has twelve anterior suture lines 714-725. The anterior suture lines are longer than the posterior suture lines and these lines are staggered when viewed along the AP axis 726. The lens fibers, which form the layers of the nucleus, are shown by lines 728; it being understood that these are only illustrative lines, and that in the actual natural layer of the lens there would be many times more fibers present.

The adult nucleus 713 is a biconvex shape that follows the outer surface of the lens. Thus, the anterior and posterior sides of this layer have different curvatures, with the anterior being flatter. These curvatures follow the curvature of the cortex and the outer layer and shape of the lens. These curvatures also generally follow the curvature of the adolescent nucleus 611, the infantile nucleus 515 and the fetal nucleus 415 and the embryonic nucleus, which are essentially concentric to and nested within the adult nucleus 611. Thus, the lens can be viewed as a stratified structure consisting of long crescent fiber cells arranged end to end to form essentially concentric or nested shells.

A subsequent adult layer having 15 sutures may also be present in some individuals after age 40. This subsequent adult layer would be similar to the later adult layer 713 in general structure, with the recognition that the subsequent adult layer would have a geometry having more sutures and would encompass the later adult layer 713; and as such, the subsequent adult layer would be the outermost layer of the nucleus and would thus be the layer further from the center of the nucleus and the layer that is youngest in age.

In general, the present invention provides for the delivery of the laser beam in patterns that utilize, or are based at least in part on, the lens suture geometry and/or the curvature of the lens and/or the various layers within the nucleus; and/or the curvatures of the various layers within the nucleus; and/or the suture geometry of the various layers within the nucleus. As part of the present invention the concept of matching the curvature of the anterior ablations to the specific curvature of the anterior capsule, while having a different curvature for posterior ablations, which in turn match the posterior curvature of the lens is provided. Anterior and posterior curvatures can be based on Kuszak aged lens models, Burd's numeric modeling, Burd et al. Vision Research 42 (2002) 2235-2251, or on specific lens measurements, such as those that can be obtained from the means for determining the position of the lens with respect to the laser. Thus, in general, these laser delivery patterns are based in whole and/or in part on the mathematical modeling and actual observation data regarding the shape of the lens, the shape of the layers of the lens, the suture pattern, and the position of the sutures and/or the geometry of the sutures.

Moreover, as set forth in greater detail, it is not necessary that the natural suture lines of the lens or the natural placement of the layers of the lens be exactly replicated in the lens by the laser shot pattern. In fact, exact replication of these natural structures by a laser shot pattern, while within the scope of the invention, is not required, and preferably is not necessary to achieve an increase in accommodative amplitude. Instead, the present invention, in part, seeks to generally emulate the natural lens geometry, structures and positioning and/or portions thereof, as well as build upon, modify and reposition such naturally occurring parameters through the use of the laser shot patterns described herein.

Figure 8:
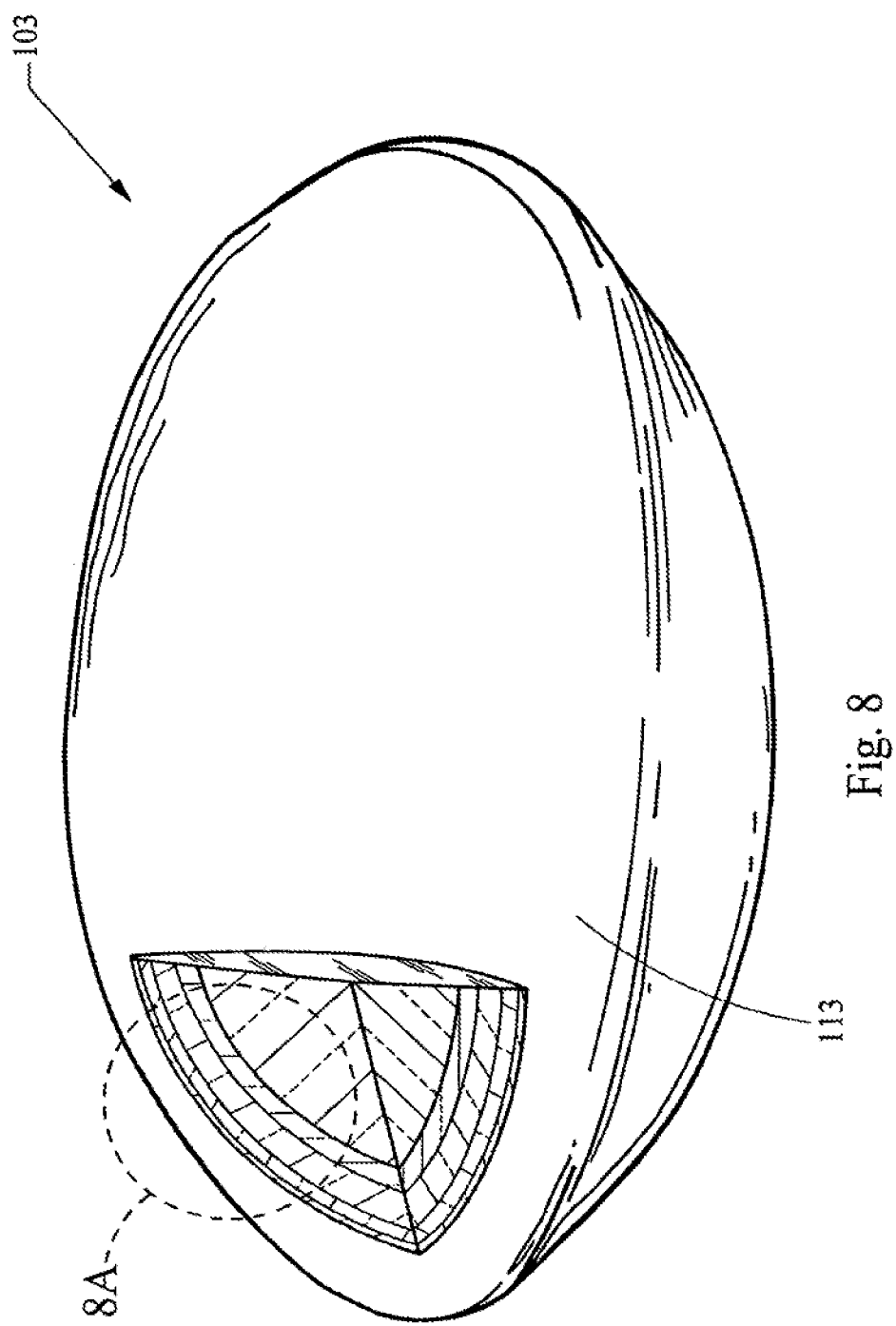
FIGS. 8 and 8A are perspective cutout views of an adult lens representing the placement of essentially concentric shells in accordance with the teachings of the present invention.
Figure 8A:
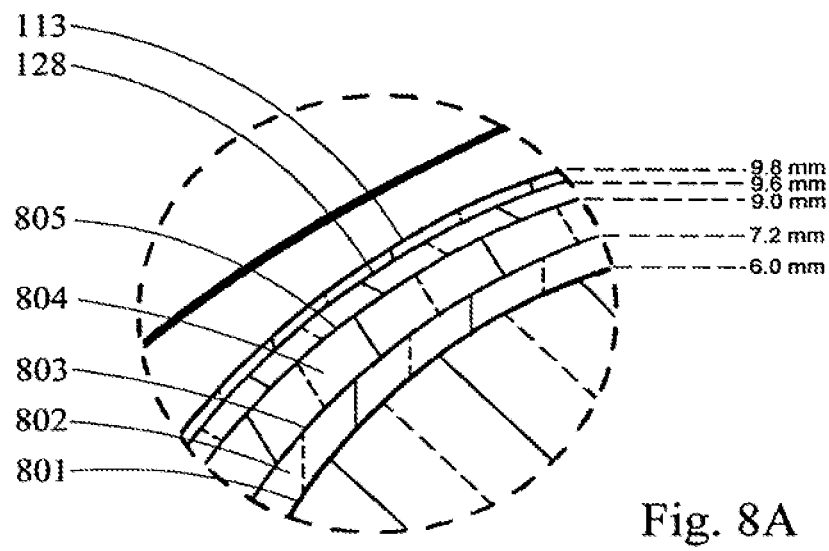

Accordingly, laser beam delivery patterns that cut a series of essentially concentric, i.e., nested, shells in the lens may be employed. Preferably, the shells would essentially follow the anterior and posterior curvature of the lens. Thus, creating in the lens a series of cuts which resemble the nucleus layers of FIGS. 4, 5, 6 and 7. These cuts may follow the same geometry, i.e., shape and distance from the center, of these layers or may follow only a part of that geometry. One example of these shells is illustrated in FIG. 8, which provides a lens 103, a first shell cut 801, a first shell 802, a second shell cut 803, a second shell 804 and a third shell cut 805. The adult nucleus 128 and cortex 113 are also provided. Thus, the term shell refers to the lens material and the term shell cut refers to the laser beam delivery pattern and consequently the placement of the laser beam shots in the lens in accordance with that pattern. More or less shell cuts, and thus shells may be utilized. Moreover, the cuts may be such that they in effect create a complete shell, i.e., the shell and shell cuts completely encompass a volume of lens material. The cuts may also be such that less than a complete shell is formed. Thus, the creation of partial shells, by the use of partial shell cuts, may be employed. Such partial cuts would for example be only a portion of a shell e.g., the anterior quartile, the anterior half, the posterior quartile, stacked annular rings, staggered annular rings, and/or combinations thereof. Such partial shells and shell cuts may be any portion of a three dimensional form, including ellipsoid, spheroids and combinations thereof as those terms are used in their broadest sense that in general follows the contours of the lens, capsule, cortex, nucleus, and/or the layers of the lens including the layers of the nucleus. Moreover, the use of complete and partial shells and shell cuts may be used in a single lens. Thus, by way of illustration of this latter point, the first and second cuts 801 and 803 are annular cuts, while the third cut is a complete cut.

A further use of partial shells is to have the shape of the shells follow the geometry and/or placement of the suture lines. Thus, partial pie shaped shells are created, by use of partial pie shaped shell cuts. These cuts may be placed in between the suture lines at the various layers of the lens. These partial shells may follow the contour of the lens, i.e., have a curved shape, or they may be flatter and have a more planar shape or be flat. A further use of these pie shape shells and shell cuts would be to create these cuts in a suture like manner, but not following the natural suture placement in the lens. Thus, a suture like pattern of cuts is made in the lens, following the general geometry of the natural lens suture lines, but not their exact position in the lens. In addition to pie shaped cuts other shaped cuts may be employed, such as by way of illustration a series of ellipses, rectangular planes or squares.

A further use of partial shells and/or planar partial shells is to create a series of overlapping staggered partial shells by using overlapping staggered partial shell cuts. In this way essentially complete and uninterrupted layers of lens material are disrupted creating planar like sections of the lens that can slide one atop the other to thus increase accommodative amplitude. These partial shells can be located directly atop each other, when viewed along the AP axis, or they could be slightly staggered, completely staggered, or any combination thereof.

In addition to the use of shells and partial shells, lines can also be cut into the lens. These lines can follow the geometry and/or geometry and position of the various natural suture lines. Thus, a laser shot pattern is provided that places shots in the geometry of one or more of the natural suture lines of one or more of the various natural layers of the lens as shown in FIGS. 4, 5, 6, and 7, as well as in the 15 suture line layer, or it may follow any of the other patterns in the continuum of layers in the lens. These shot patterns can follow the general geometry of the natural suture lines, i.e., a series of star shapes with the number of legs in each star increasing as their placement moves away from the center of the lens. These star shaped shot patterns may follow the precise geometry of the natural suture patterns of the layers of the lens; or it can follow the exact geometry and placement of the sutures, at the same distances as found in the natural lens or as determined by modeling of the natural lens. In all of these utilizations of star patterns one or more stars may be cut. The length of the lines of the legs of the star may be the longer, shorter or the same length as the natural suture lines. Moreover, if the length is shorter than the natural length of the suture lines, it may be placed toward the center of the star shape, i.e. the point where the lines join each other, or towards the end of the suture line, i.e., the point furthest on the suture line from the joining point. Further, if the cut is towards the end of the suture line it may extend beyond the suture line or may be co-terminus therewith. Moreover, partial star shaped cuts can be used, such as cuts having a "V" shape, or vertical or horizontal or at an angle in between. These linear cuts, discussed above, are in general referred to herein as laser created suture lines. Moreover, laser created suture lines may be grouped together to in effect form a shell or partial shell.

Figure 3:
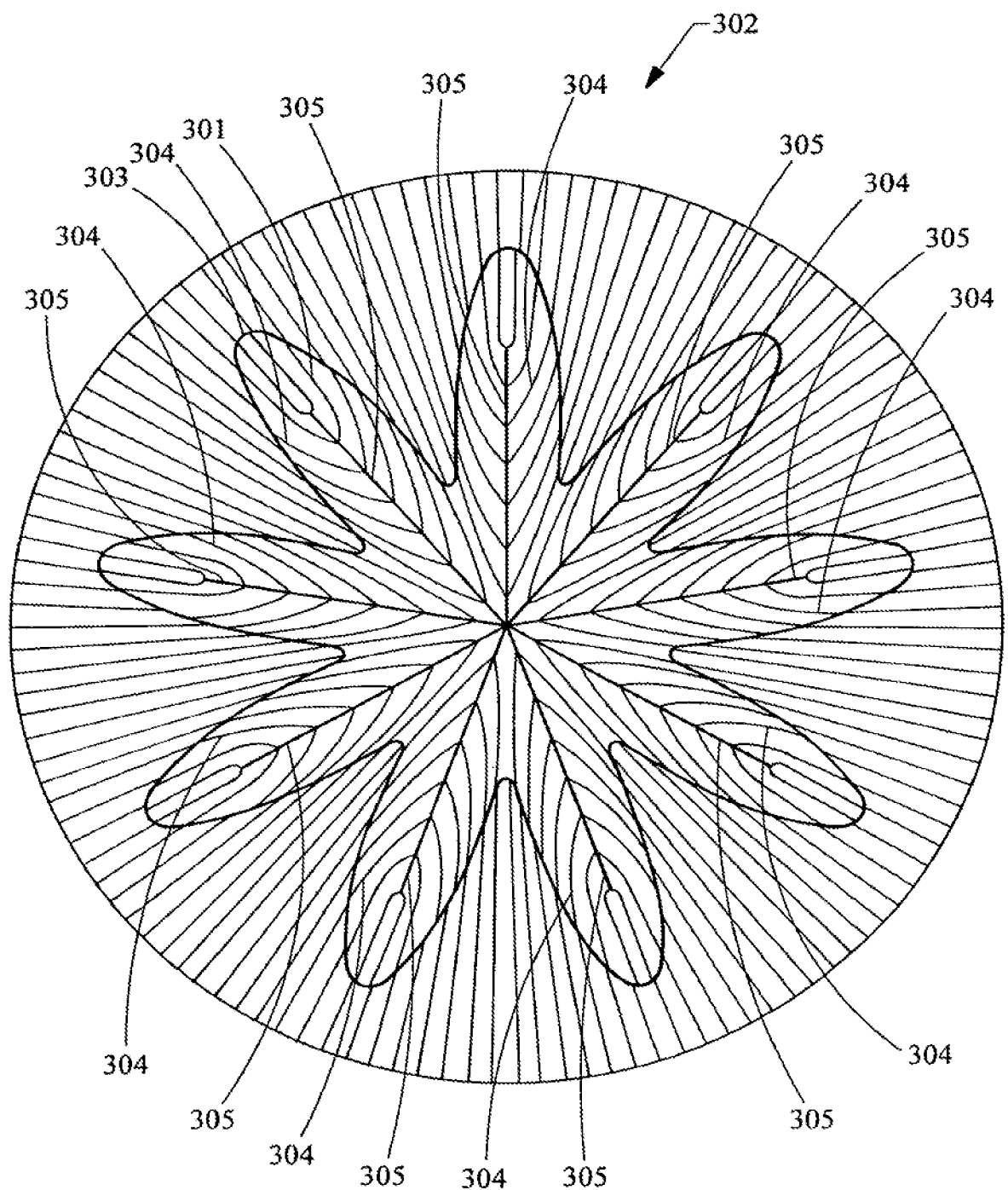
FIG. 3 is a diagram of the anterior surface of a lens normal to the AP axis illustrating a laser shot pattern having a flower like shape which has a contour generally following approximately the last 15% of the fiber length from the end of the fiber.
Figure 4A:
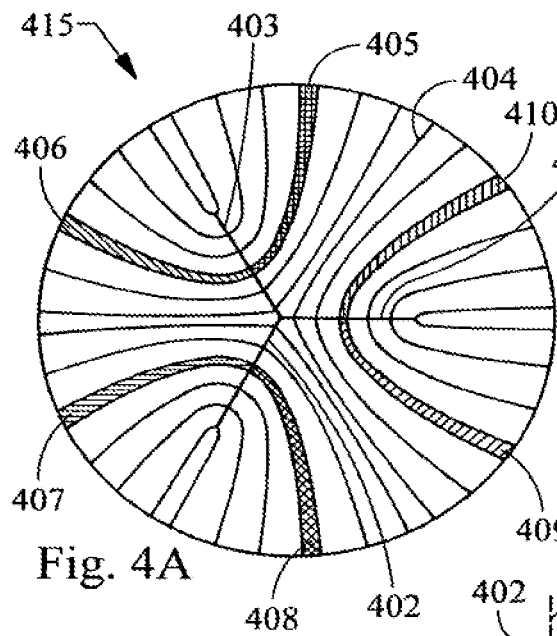
FIGS. 4A, 4B, 4C, 4D and 4E are diagrams representing elevation views of the geometry used for the development of laser shot patterns based upon the structure of the fetal nucleus (three suture branch nucleus) as it is rotated from the posterior view 4A through and to the anterior view 4E.
Figure 4B:
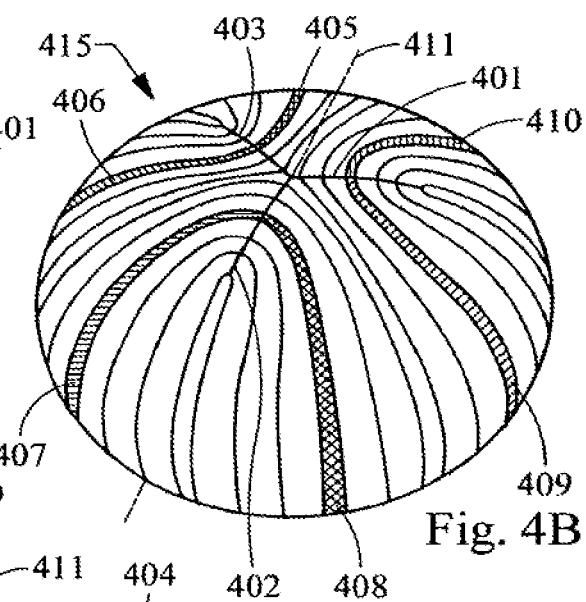
Figure 4C:
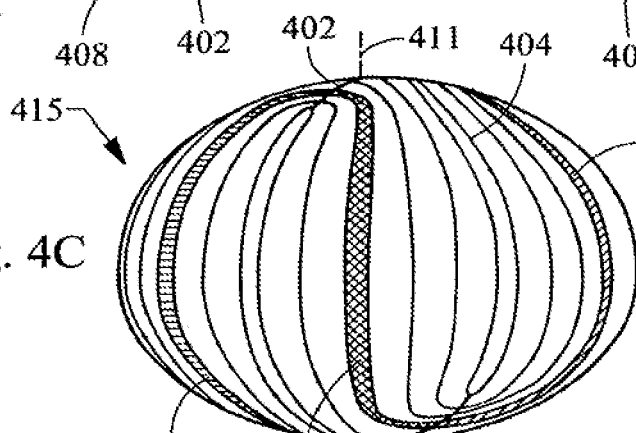
Figure 4D:
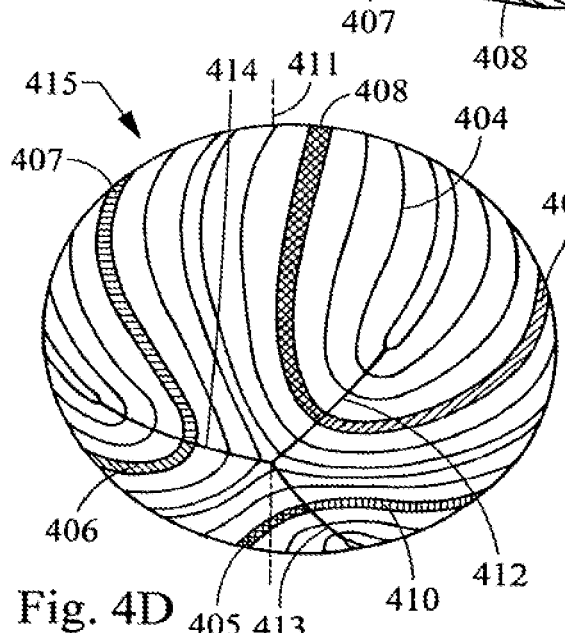
Figure 4E:
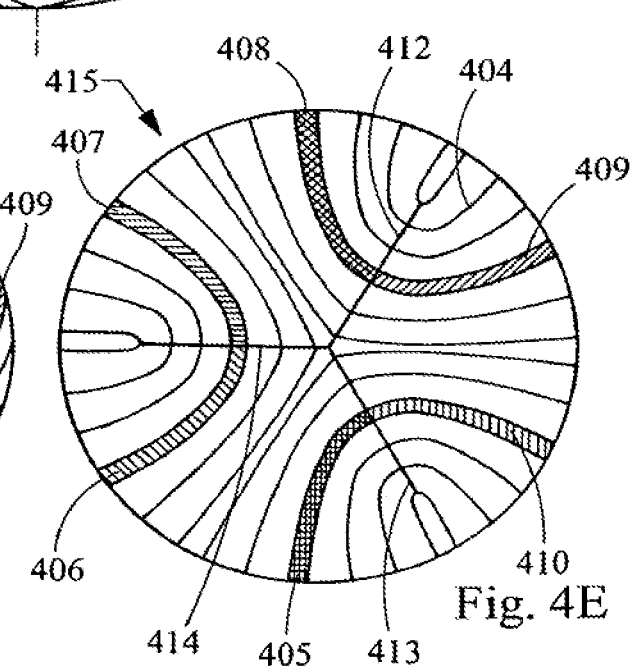

At present, it is theorized that the use of cuts near the end of the suture lines will have the greatest effect on increasing accommodative amplitude because it is believed that the ends of fibers near the anterior and posterior poles (the point where the AP axis intersects the lens) of the lens are more free to move then the portions of fibers near the equator where there is a greater number of gap junctions which bind fiber faces. At present, it is postulated that it is approximately the last 15% of the fiber length that is most free in the youthful lens with high accommodative amplitude. It is further theorized that fiber layers tend to become bound with age due to a combination of increase in surface roughness and compaction due to growth of fiber layers above. Thus, as illustrated in FIG. 3 a shot pattern 301 is provided to an anterior portion of a layer 302 of the lens. This shot pattern 301 has a contour 303 that follows the contour of approximately the last 15% of fiber length of fibers, represented by lines 304. Thus, the shell cut resembles the shape of a flower. Additionally, the number of petals in the flower shaped shell should correspond to the number of suture lines 305 at that growth layer. Thus, it is theorized that this partial shell cut and/or cuts will have the effect of unbinding the layers and returning the lens to a more youthful increased amplitude of accommodation. Similarly, using partial shells, annular partial shells or planar partial shells in this general area, i.e., the general area at or near the ends of the suture lines, may be employed for the same reasons. This theory is put forward for the purposes of providing further teaching and to advancing the art. This theory, however, is not needed to practice the invention; and the invention and the claims herein are not bound by or restricted by or to this theory.

The use of laser created suture lines, including star shaped patterns may also be used in conjunction with shells, partial shells and planar partial shells. With a particular laser shot pattern, or series of shot patterns, employing elements of each of these shapes. These patterns may be based upon the geometry shown in FIGS. 4-7 as well as the 15 suture line geometry discussed herein; they may follow that geometry exactly, in whole or in part; and/or they may follow that geometry, in whole or in part, as well as following the position of that geometry in the lens. Although a maximum of 15 suture lines is known in the natural lens, more than 15 laser created suture lines may be employed. Moreover, as provided herein, the lens has multiple layers with a continuum of suture lines ranging from 3 to 15 and thus, this invention is not limited to the suture patents of FIGS. 4-7, but instead covers any number of suture lines from 3 to 15, including fractions thereof.

The delivery of shot patterns for the removal of lens material is further provided. A shot pattern that cuts the lens into small cubes, which cubes can then be removed from the lens capsule is provided. The cubes can range in size from a side having a length of about 100 μm to about 4 mm, with about 500 μm to 2 mm being a preferred size. Additionally, this invention is not limited to the formation of cubes and other volumetric shapes of similar general size may be employed. In a further embodiment the laser is also used to create a small opening, capsulorhexis, in the lens anterior surface of the lens capsule for removal of the sectioned cubes. Thus, this procedure may be used to treat cataracts. This procedure may also be used to remove a lens having opacification that has not progressed to the point of being cataractous. This procedure may further be used to remove a natural lens that is clear, but which has lost its ability to accommodate. In all of the above scenarios, it being understood that upon removal of the lens material the lens capsule would subsequently house a suitable replacement, such as an IOL, accommodative IOL, or synthetic lens refilling materials. Moreover, the size and the shape of the capsulorhexis is variable and precisely controlled and preferably is in 2 mm or less diameter for lens refilling applications and about 5 mm for IOLs. A further implementation of the procedure to provide a capsulorhexis is to provide only a partially annular cut and thus leave a portion of the capsule attached to the lens creating a hinged flap like structure. Thus, this procedure may be used to treat cataracts.

It is further provided that volumetric removal of the lens can be performed to correct refractive errors in the eye, such as myopia, hyperopia and astigmatism. Thus, the laser shot pattern is such that a selected volume and/or shape of lens material is removed by photodisruption from the lens. This removal has the affect of alternating the lens shape and thus reducing and/or correcting the refractive error. Volumetric removal of lens tissue can be preformed in conjunction with the various shot patterns provided for increasing accommodative amplitude. In this manner both presbyopia and refractive error can be addressed by the same shot pattern and/or series of shot patterns. The volumetric removal of lens tissue finds further application in enhancing corrective errors for patients that have had prior corneal laser visions correction, such as LASIK, and/or who have corneas that are too thin or weak to have laser corneal surgery.

In all of the laser shot patterns provided herein it is preferred that the laser shot patterns generally follow the shape of the lens and placement of individual shots with respect to adjacent shots in the pattern are sufficiently close enough to each other, such that when the pattern is complete a sufficiently continuous layer and/or line and/or volume of lens material has been removed; resulting in a structural change affecting accommodative amplitude and/or refractive error and/or the removal of lens material from the capsule. Shot spacing of lesser or greater distances are contemplated herein and including overlap as necessary to obtain the desired results. Shot spacing considerations include gas bubble dissipation, volume removal efficiency, sequencing efficiency, scanner performance, and cleaving efficiency among others. For example, by way of illustration, for a 5 µm size spot with an energy sufficient to cause photodisruption, a spacing of 20 µm or greater results in individual gas bubbles, which are not coalesced and dissipate more quickly, than with close shot spaces with the same energy, which result in gas bubble coalescence. As the shot spacing gets closer together volume efficiency increases. As shot spacing gets closer together bubble coalescence also increases. Further, there comes a point where the shot spacing becomes so close that volume efficiency dramatically decreases. For example, by way of illustration, for a 450 femtosecond pulse width and 2 microjoules energy and about a 5 µm spot size with a 10 µm separation results in cleaving of transparent ocular tissue. As used herein, the term cleaving means to substantially separate the tissue. Moreover, the forgoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics referrers to the effects that take place surrounding photodisruption, such as plasma formation and expansion, shock waive propagation, and gas bubble expansion and contraction. Thus, the timing of sequential pulses such that they are timed faster than some of, elements of, or all of those effects, can increase volumetric removal and/or cleaving efficiency. Accordingly, we propose using pulse repetition frequencies from 50 MHz to 5 GHz., which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption.

The terms first, second, third, etc. as used herein are relative terms and must be viewed in the context in which they are used. They do not relate to timing, unless specifically referred to as such. Thus, a first cut may be made after a second cut. In general, it is preferred to fire laser shots in general from posterior points in the laser pattern to anterior points, to avoid and/or minimize the effect of the gas bubbles resulting from prior laser shots. However, because of the varied laser shot patterns that are provided herein, it is not a requirement that a strict posterior to anterior shot sequence be followed. Moreover, in the case of cataracts it may be advantageous to shoot from anterior to posterior, because of the inability of the laser to penetrate substantially beyond the cataract.

Without further elaboration, it is believed that one skilled in the art can, using the preceding description, utilize the present invention to its fullest extent. The following specific embodiments are, therefore, provided as examples of the invention and should be construed as being merely illustrating and not limiting the scope of the invention or the disclosure herein in any way whatsoever.

The following examples are based upon measured lens data and lens data that is obtained by using Burd modeling, which model is set forth in Burd et al., Numerical modeling of the accommodating lens, Visions Research 42 (2002) 2235-2251. The Burd model provides the following algorithm for anterior and/or posterior shape:

$$Z = aR^5 + bR^4 + cR^3 + dR^2 + f$$

The coefficients for this algorithm are set forth in Table II.

TABLE II

|  | a | b | c | d | f |
| --- | --- | --- | --- | --- | --- |
| Anterior (11-year) | −0.00048433393427 | 0.00528772036011 | −0.01383693844808 | −0.07352941176471 | 2.18 |
| Posterior (11-year) | 0.00300182571400 | −0.02576464843559 | 0.06916082660799 | 0.08928571428571 | −2.13 |
| Anterior (29-year) | −0.00153004454939 | 0.01191111565048 | −0.02032562095557 | −0.07692307692308 | 2.04 |
| Posterior (29-year) | 0.00375558685672 | −0.03036516318799 | 0.06955483582257 | 0.09433962264151 | −2.09 |
| Anterior (45-year) | −0.00026524088453 | 0.00449862869630 | −0.01657250977510 | −0.06578947368421 | 2.42 |
| Posterior (45-year) | 0.00266482873720 | −0.02666997217562 | 0.08467905191557 | 0.06172839506173 | −2.42 |

Figure 9:
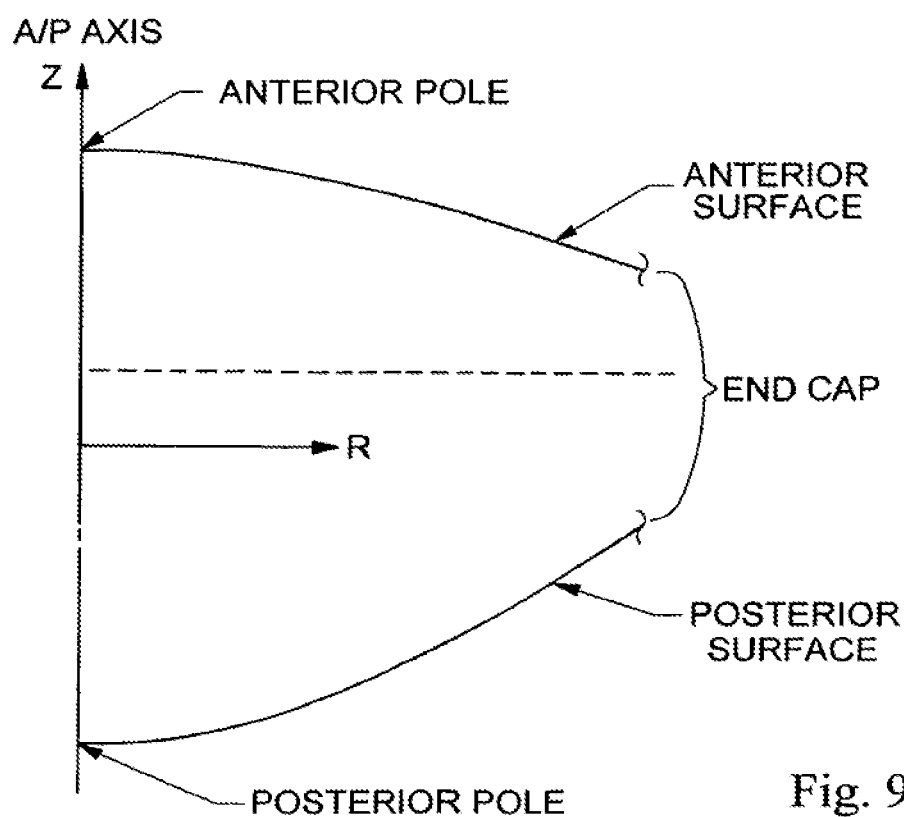
FIG. 9 is a cross-section drawing of the lens relating to the model developed by Burd.

Additionally, the variables Z and R are defined by the drawing FIG. 9.

Figure 10:
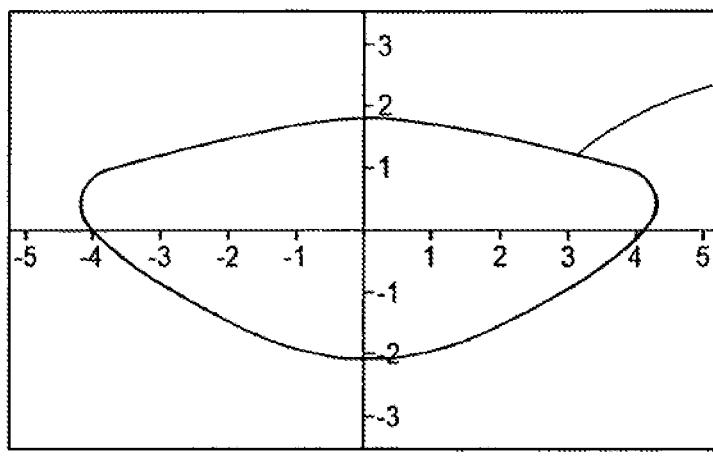
FIG. 10 is a cross-section drawing of a lens based upon the model developed by Burd.
Figure 11:
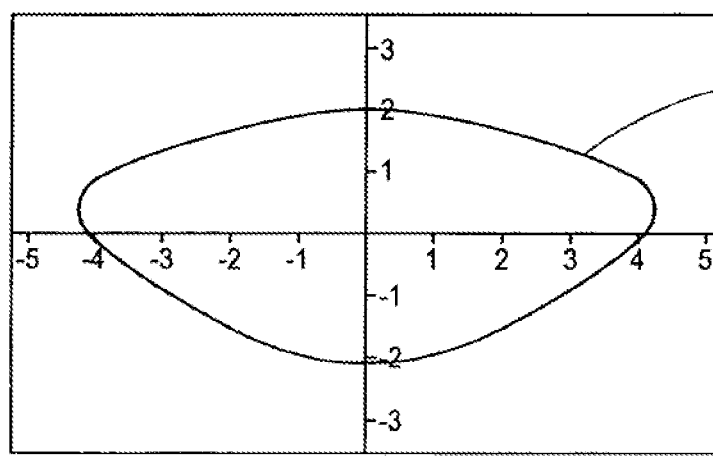
FIG. 11 is a cross-section drawing of a lens based upon the model developed by Burd.
Figure 12:
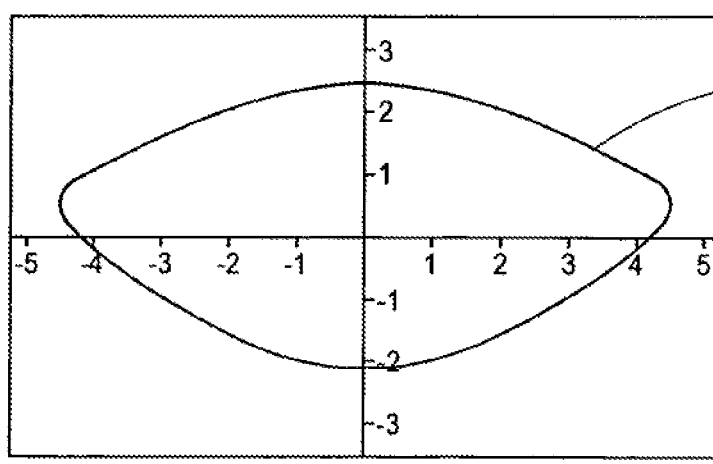
FIG. 12 is a cross-section drawing of a lens based upon the model developed by Burd.

Thus, FIGS. 10, 11 and 12 provide cross sectional views of the lens having an outer surface 1001, 1101, 1201 for three ages, 18, 29 and 45-year old respectively, based upon the Burd model and show growth in size along with shape changes with age. The units for the axes on these drawings, as well as for FIGS. 13 to 29 are in millimeters (mm).

Figure 13:
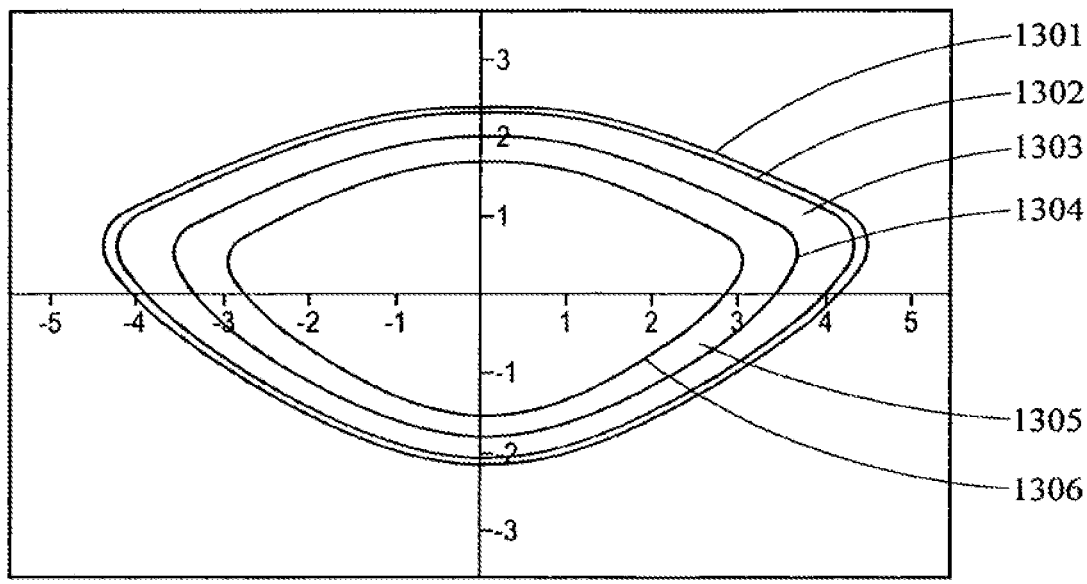
FIG. 13 is a cross-section drawing of a lens showing the placement of a shell laser shot pattern in accordance with the teachings of the present invention.

EXAMPLE 1, provides for making nested, lens shaped shell cuts. The laser shot patterns are illustrated in FIG. 13, which provides the outer surface 1301 of a 45-year old lens based upon the Burd model. There is further provided a series of nested or essentially concentric shells and shell cuts, which essentially follow the shape of the lens. Thus, there is provided a first shell cut 1302, a second shell cut 1304, and a third shell cut 1306. These shell cuts form a first shell 1303 and a second shell 1305. Shells or partial shells are designed to increase flexibility in the lens by decreasing the strength of nested fiber layers by separating the bound layers, which it is theorized would reduce the structural strength and increase deflection for a given load or force.

Thus, although not bound by this theory, it theorized that increasing the deflection of the lens for a given load or zonule force will increase the flexibility of the lens structure and, in turn, the amplitude of accommodation for that same zonule force. Thus, there are provided a nested set of three layers, which essentially follows both the anterior and posterior shapes. Moreover, it being readily understood that for this and the other examples that the shell cut is formed by and thus corresponds to a laser shot pattern.

Thus, the shell cuts in this example are positioned approximately such that the third shell cut 1306 is where 3 suture branches begin forming additional branches, or approximately 6 mm lens equatorial diameter, at the boundary of the fetal nucleus, or the lens at birth; the second shell cut 1304 is where the 6 suture branch layer begins forming additional branches at approximately 7.2 mm diameter, or the infantile nucleus or the lens at approximately age 3; and the first shell cut is where the 9 suture branch begins forming additional branches at approximately 9 mm diameter, or at the adolescent nucleus at approximately age 13.

Figure 14:
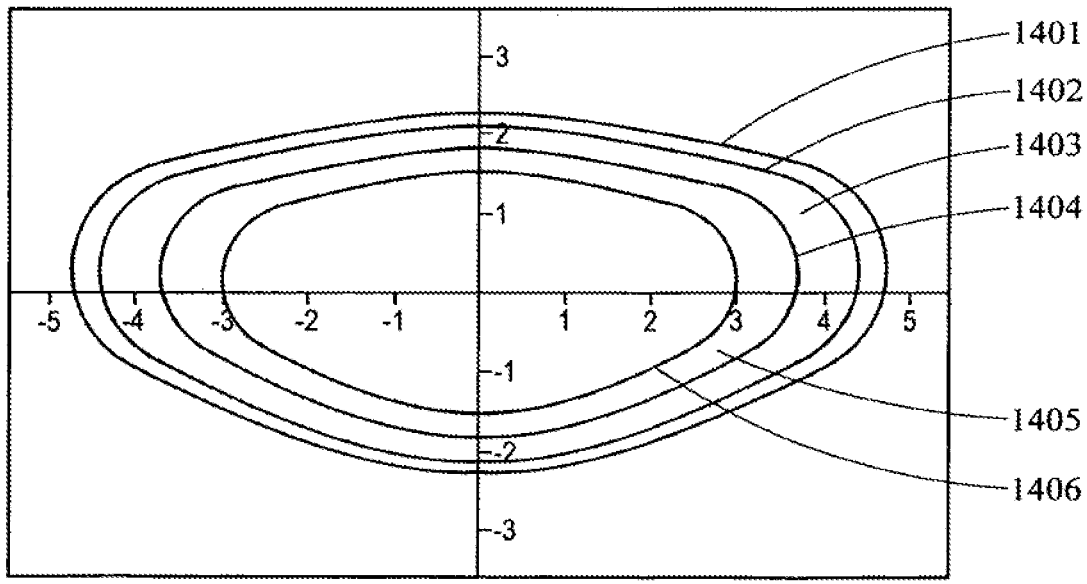
FIG. 14 is a cross-section drawing of a lens showing the placement of a shell laser shot pattern in accordance with the teachings of the present invention.

EXAMPLE 2, provides as an alternative to using a 45-year old lens shape from the Burd model, the actual patient lens structural or shape data may be utilized to customize surgery for each patient. As an example, a 45-year old human cadaver lens, whose shape was measured optically and mathematically fit via the same fifth order function used in the Burd model, yields coefficients unique to the measured lens. The outer cross-section shape of this lens and a shot pattern similar to that of Example 1, but which was tailored to the particular lens of this Example is illustrated in FIG. 14. Thus, there is provided in this Figure an outer surface 1401 of the 45-year old lens. There is further provided a series of nested or essentially concentric shells and shell cuts. Thus, there is provided a first shell cut 1402, a second shell cut 1404, and a third shell cut 1406. These shell cuts form a first shell 1403 and a second shell 1405. It is further noted that any of the exemplary cuts and shot patterns can be implemented via partial or full shells and/or can be implemented via modeled (the Burd model being just one example) or measured lens data.

Figure 15:
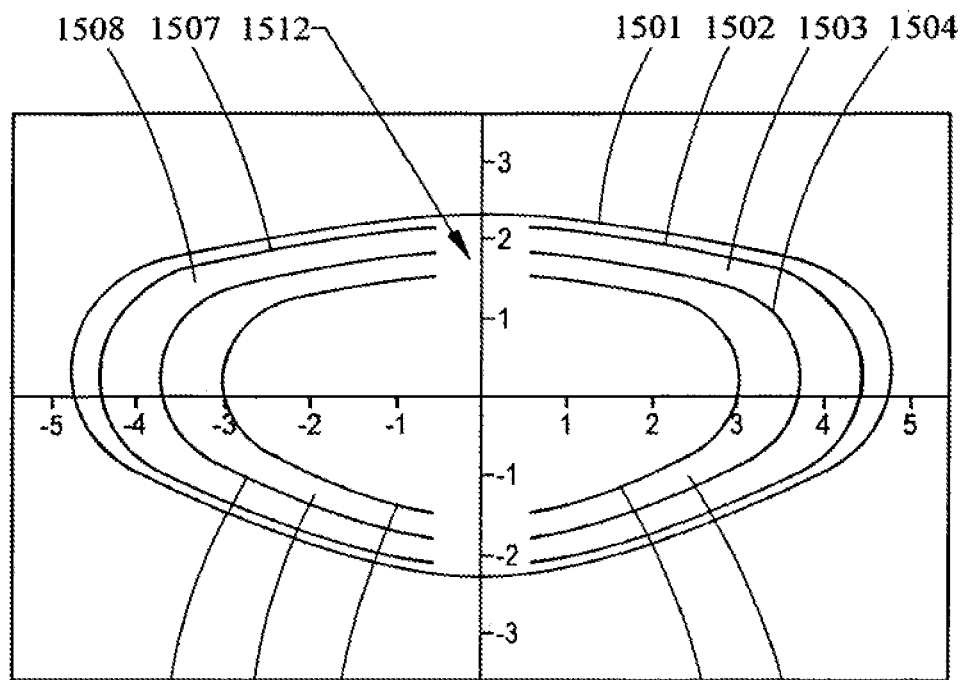
FIG. 15 is a cross-section drawing of a lens showing the placement of a partial shell laser shot pattern in accordance with the teachings of the present invention.

EXAMPLE 3 provides a shot pattern for cutting partial shells on the measured 45-year old lens, and having an excluded defined central zone. Thus, as illustrated in FIG. 15 there is provided an outer surface 1501 of a 45-year old lens, a central zone 1512, partial cuts 1502, 1504, 1506, 1507, 1509 and 1511. This also provided partial shells 1503, 1505, 1508 and 1510. These partial cuts as shown are part of the same generally annularly shaped. Thus, cuts 1502 and 1507, cuts 1504 and 1509, and cuts 1506 and 1511 are the opposite sides respectively of three generally annularly shaped partial.

Figure 16:
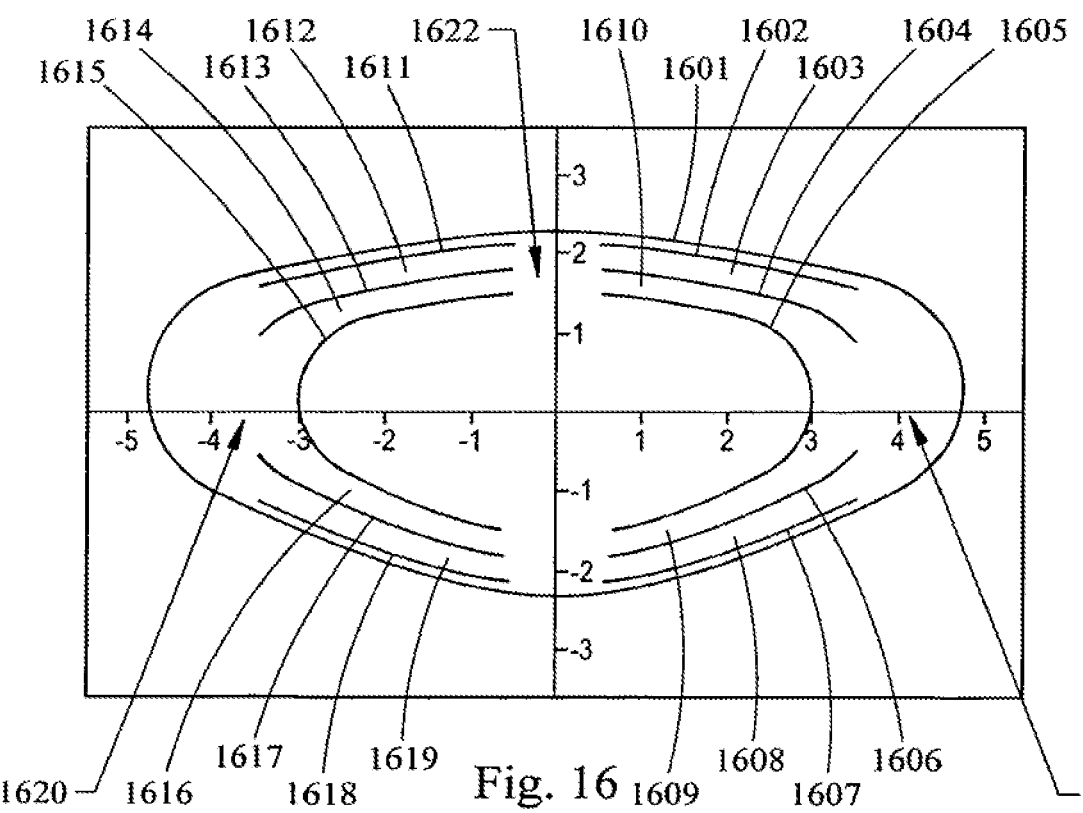
FIG. 16 is a cross-section drawing of a lens showing the placement of a partial shell laser shot pattern in accordance with the teachings of the present invention.

EXAMPLE 4 provides a shot pattern for cutting partial shells on the measured 45-year old lens, and having both an excluded defined peripheral zone and central zone. Thus, as illustrated in FIG. 16, there is provided an outer surface 1601 of a 45-year old lens, a central zone 1622 and two peripheral zones 1620 and 1621. There is further provided partial cuts 1602, 1604, 1605, 1606, 1607, 1611, 1613, 1615, 1617, and 1618 as well as, partial shells 1603, 1608, 1609, 1610, 1612, 1614, 1616 and 1619. As with example 3 and FIG. 15 these cuts are viewed in cross section and thus it is understood that they are opposite sides of generally annular ring shaped cuts, which essentially follow the shape of the lens and which encompasses the central zone 1622. There are thus 5 partial cuts depicted in FIG. 16.

Figure 17:
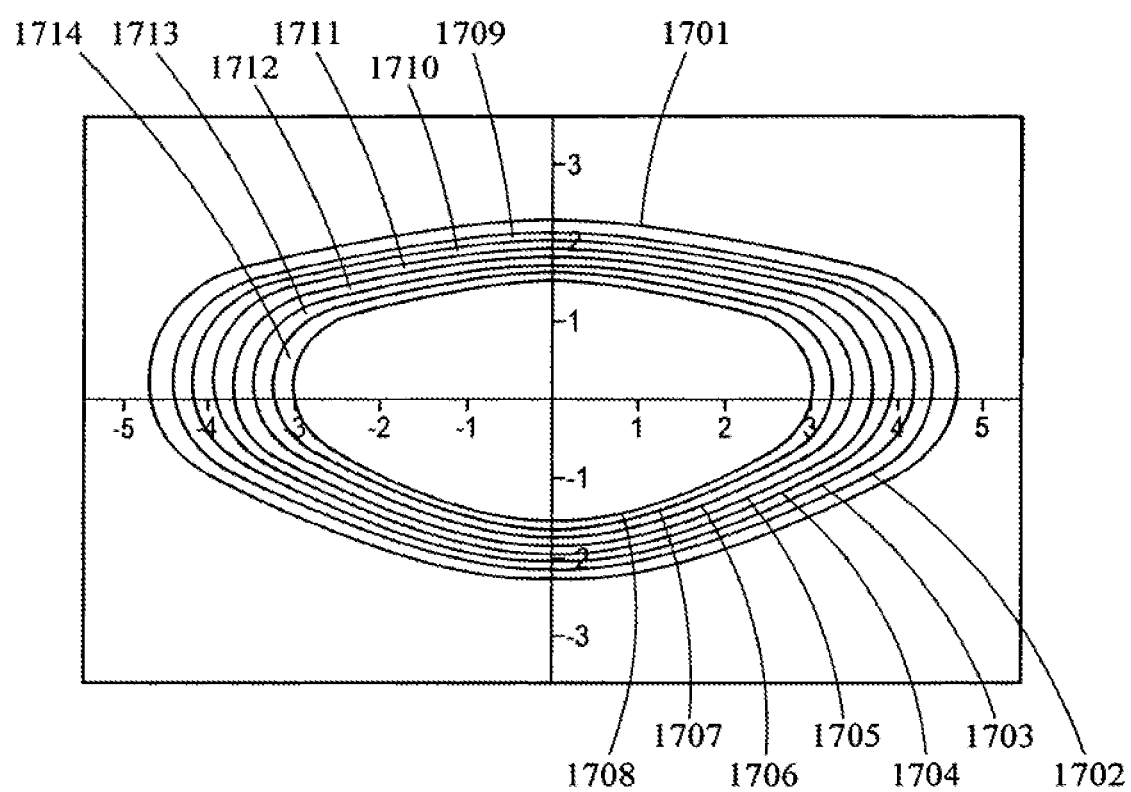
FIG. 17 is a cross-section drawing of a lens showing the placement of a shell laser shot pattern in accordance with the teachings of the present invention.

EXAMPLE 5 provides a laser shot patter for a finer detailed cutting of the lens to approximate the structural boundaries at 3, 4, 5, 6, 7, 8, 9 suture branches, or the use of six shells. Thus, there is shown in FIG. 17 seven essentially concentric shot patterns 1702-1708, which create seven corresponding shell cuts and which also create six corresponding shells 1709-1714. The outer surface 1701 of a 45-year old lens as measured is also provided in FIG. 17. While this example provides for the creation of six shells, it is understood that the lens contains thousands of fiber layers and that it may be desirable to utilize much greater than six shells and up to hundreds or even thousands, depending on the resolution of the laser deliver system and laser beam parameters.

Examples 6-12 relate to the volumetric removal of lens material in a predetermined shape, based upon a precise shot pattern. Thus, these examples illustrate how refractive change by shaped volumetric reduction may be accomplished. This approach recognizes a limitation of photodisruption laser beam delivery, i.e., that the gas bubbles created are considerably larger then the resultant material void found after all gas bubble dissipation occurs. This can have the effect of causing material voids to be spaced further apart than ideal for high efficiency volume removal. Thus, it is recognized that the closest spacing attainable, depending on detailed laser spot size, energy and pulse width, may provide a low, net volumetric removal efficiency, which is the ratio of achieved volume removal to the volume of material treated. A simple example considers a void size equal to the spacing between voids yielding a nominal 50% linear efficiency, which from symmetric geometry has a 25% area efficiency and a corresponding 12.5% volumetric efficiency of void creation. Thus, by way of example an approach is provided whereby the treatment shaped volume is proportionally larger than desired shaped volume removal to compensate for the low volume efficiency. In other words, if a large shape change with low volume removal efficiency is attempted then a small shape change should be achieved. Other effects such as void shape, asymmetries, void location, tissue compliance as a function of age, external forces and more, may effect the final volume efficiency and experimental validation of volumetric efficiency may be required.

Figure 18:
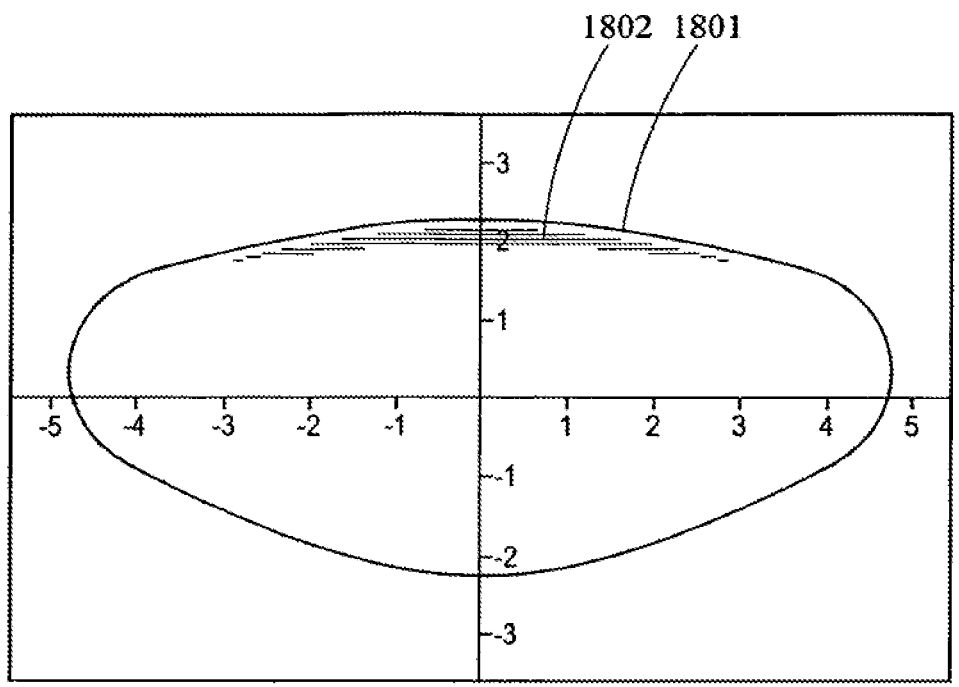
FIGS. 18-24 are cross-section drawings of a lens showing the placement of a volumetric removal laser shot patterns in accordance with the teachings of the present invention.

EXAMPLE 6 provides a shot pattern and volume removal to make a negative refractive change, or reduce the power in the crystalline lens by 3 Diopters, using the Gullstrand-LaGrand optical model, which would require the removal of approximately 180 um centrally tapering to 0 over a 3 mm radius. As illustrated in FIG. 18 there is provided an outer lens surface 1801 and a shot pattern 1802 for the desired volume removal. To achieve the full 3 Diopters refractive change directly, the shot pattern would have to remove essentially 100% of the shaded region volume which is extremely difficult due to low volume efficiency found in photodissruption laser beam delivery.

Figure 19:
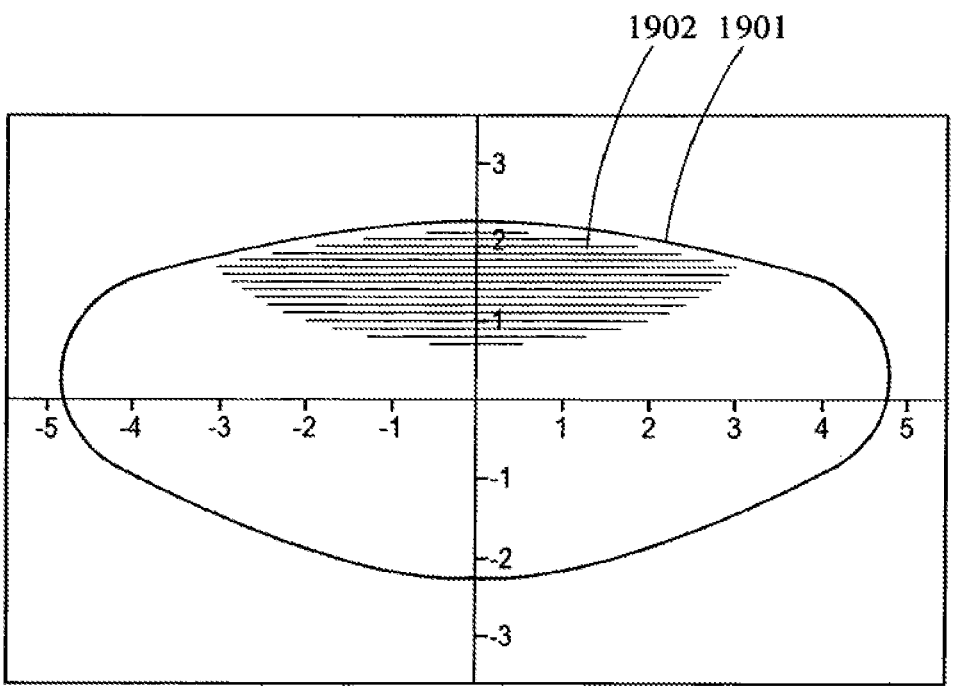

EXAMPLE 7, is based upon dealing with low volume removal efficiency and in this example the assumption that we have a volumetric efficiency of 12.5% or $\frac{1}{8}^{th}$ we would treat an 8 times larger volume or 1.44 mm thick to compensate for the low volume efficiency, tapering to 0 over the same 3 mm as shown in FIG. 19, which illustrates a lens outer surface 1901 and a shot pattern 1902. As with the prior examples the shape of the shot pattern is based upon and essentially follows the shape of the outer surface 1901 of the lens.

Figure 20:
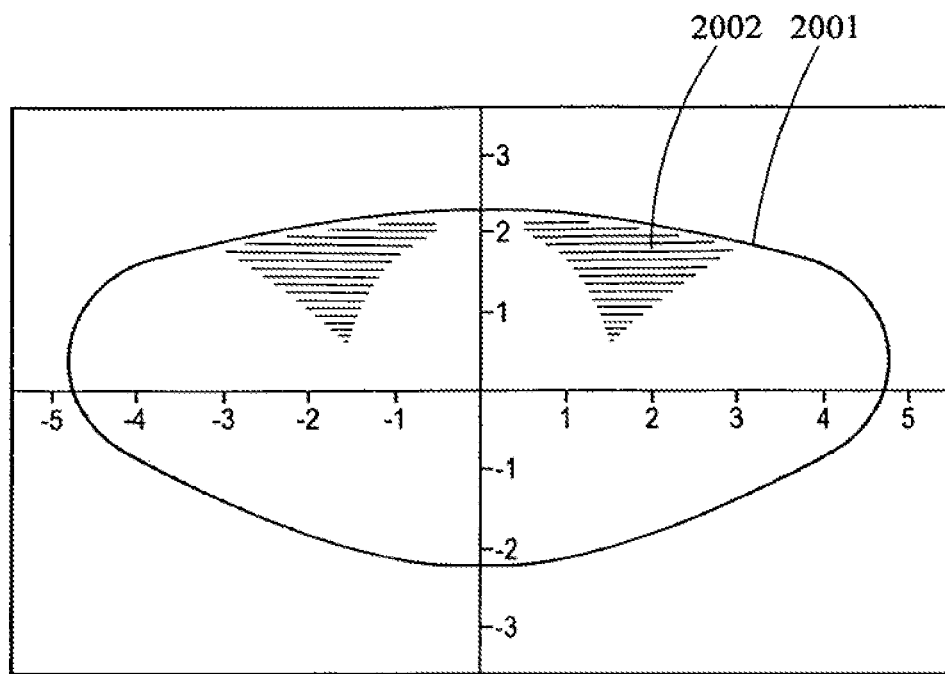

EXAMPLE 8 provides a shot pattern to cause a refractive change to increase lens power or reduce hyperopia in patients, where the shot pattern is primarily implemented in the anterior region of the lens. This pattern is illustrated in FIG. 20, which provides an outer surface 2001 and thus shape of the lens and a shot pattern 2002.

Figure 21:
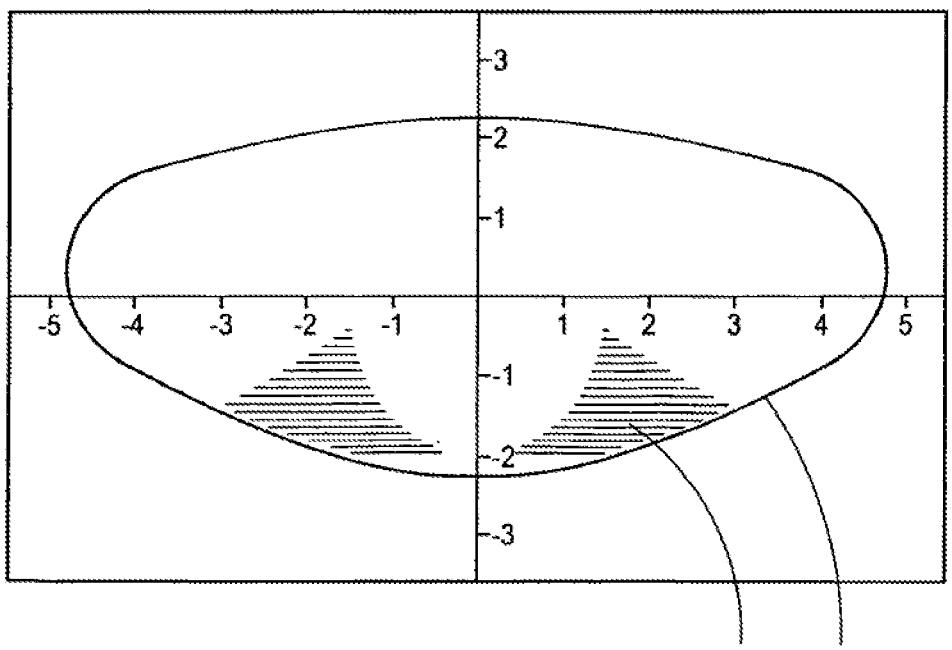

EXAMPLE 9 provides a shot pattern to cause a refractive change to increase lens power or reduce hyperopia in patients, where the algorithm is primarily implemented in the posterior region of the lens. This pattern is illustrated in FIG. 21, which provides an outer surface 2101 and thus shape of the lens and a shot pattern 2102. This example further illustrates a shot pattern having a shape is modified to primarily follow the posterior curve of the lens.

Figure 22:
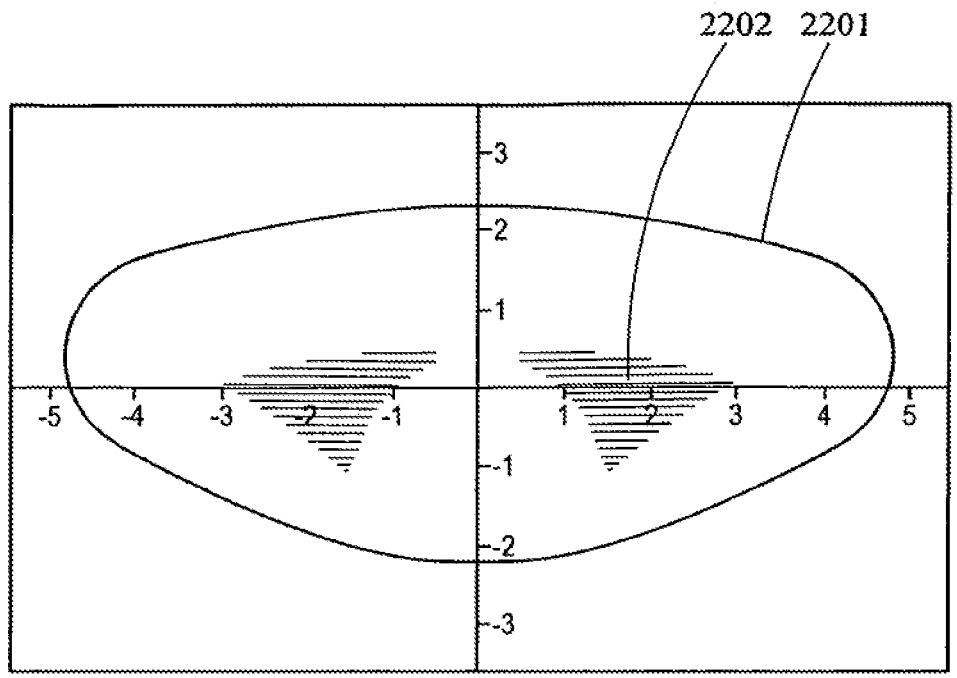

EXAMPLE 10 provides a shot pattern to cause a refractive change to increase lens power or reduce hyperopia in patients, where the shot pattern is primarily implemented in the central region of the lens. Thus, as illustrated in FIG. 22, there is provided an outer surface 2201 of the lens and a shot pattern 2202, which provides a volumetric shape. It further being noted that the anterior shape of the lens or posterior shape of the lens or both can be utilized to determine the shape of the shot pattern and/or volumetric shape.

Figure 23:
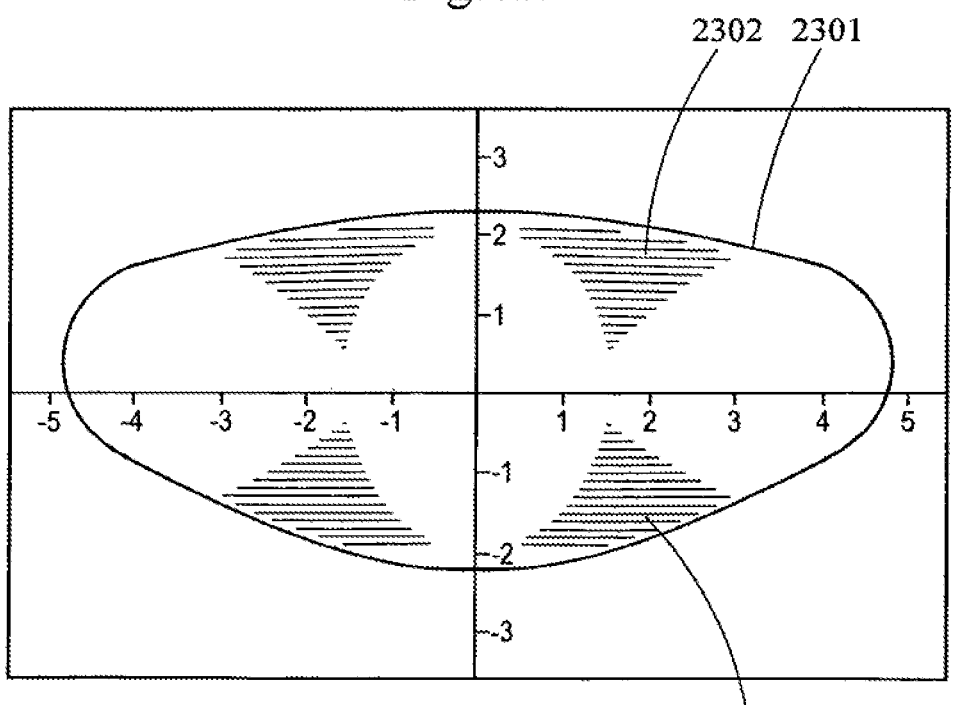

EXAMPLE 11 provides two volumetric shot patterns that follow the shape of the lens surface to which they are adjacent. Thus, as illustrated in FIG. 23, there is provided an outer surface 2301 and thus shape of the lens and a shot pattern having two volumetric shot patterns; a first shot pattern 2302 positioned in the anterior region of the lens and a second shot pattern 2303 positioned in the posterior region, which patterns provide a volumetric shape. Thus, the volumetric shapes to be removed from the lens are located in the anterior and posterior regions of the lens and have a surface that follows the anterior and posterior shape of the lens respectively.

Figure 24:
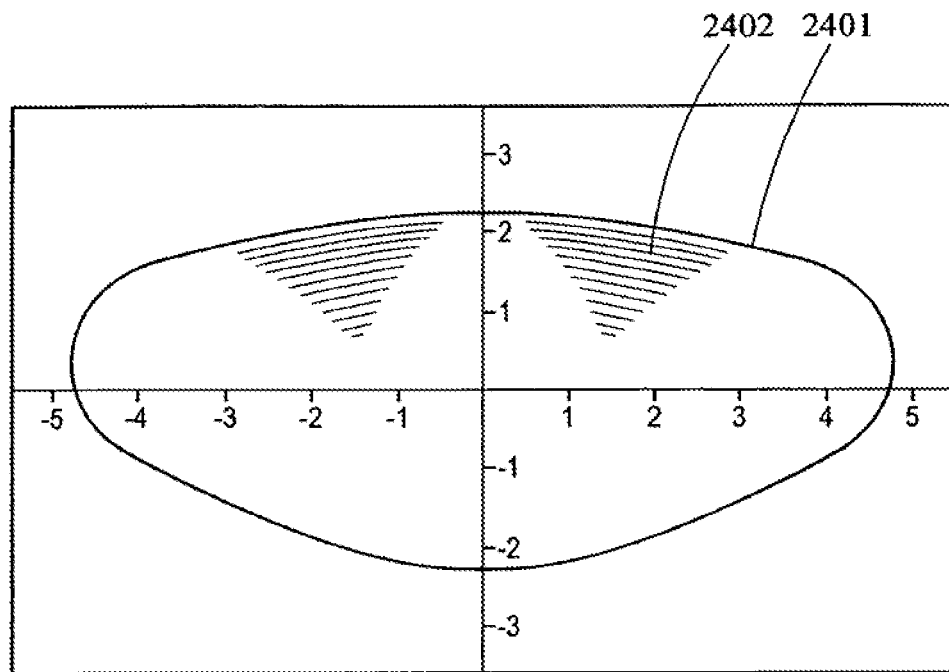

EXAMPLE 12 illustrates a manner in which different shot pattern features are combined to address both refractive errors and those to increase flexibility utilizing a plurality of stacked partial shells, which are partially overlapping. Thus, as illustrated in FIG. 24, there is provided an outer surface 2401 and thus shape of the lens and there are provided partial shell cuts 2402, whose extent is defined by a refractive shape, forming annular rings shaped partial shells 2403. The placement of the partial shell cuts are adjacent the anterior surface of the lens as shown it FIG. 24. The partial shell cuts may similarly be placed adjacent the posterior surface of the lens, in which case they should follow the shape of that surface. Thus, by precisely following the individual shape of the layers within the lens more effective cleaving is obtained.

The shot pattern in the figures associated with EXAMPLES 6, 7, 8, 9, 10 and 11 are shown to cut horizontal partial planes whose extent is defined by a refractive shape. It is to be understood that as an alternative to horizontal planes, vertical partial planes or other orientation cuts whose extent is defined by the refractive shape may be used.

Examples 13 and 14 are directed towards methods and shot patterns for treating and removal of cataracts and/or for clear lens extractions. Thus, there is provided a method for the structural modification of the lens material to make it easier to remove while potentially increasing the safety of the procedure by eliminating the high frequency ultrasonic energy used in Phaco emulsification today. In general, the use of photodissruption cutting in a specific shape patterns is utilized to carve up the lens material into tiny cube like structures small enough to be aspirated away with 1 to 2 mm sized aspiration needles.

EXAMPLE 13 provides a shot pattern to create 0.5 mm sized cubes out of the lens material following the structural shape of a 45-year old Burd Model lens. It is preferred that the patient's actual lens shape can be measured and used.

Figure 25:
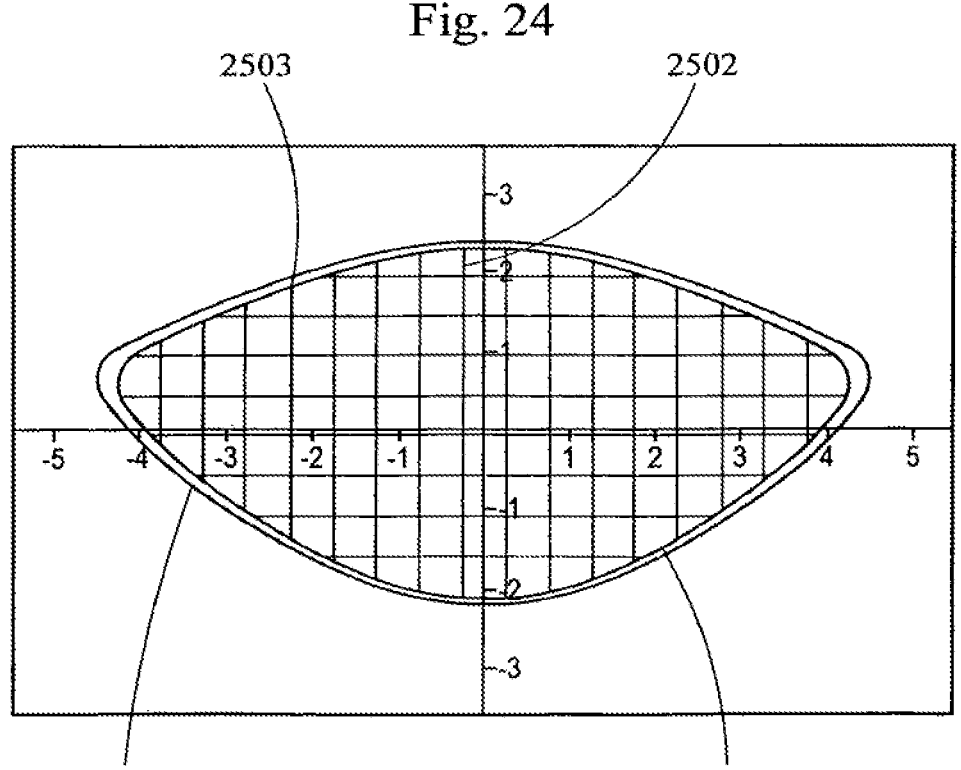
FIG. 25 is a cross-section drawing of a lens showing the placement of a cube laser shot pattern in accordance with the teachings of the present invention.

Thus, as illustrated in FIG. 25, there is provided an outer surface 2501 and thus an outer shape of the lens. There is further provided a shot pattern 2502 that creates grid like cuts, the end of which cuts 2503 essentially follows the shape of the lens. There is further provided one shell cut 2504, which is integral with the grid like cuts. The sequence of laser shots in the pattern in FIG. 25 may be executed from posterior to anterior, as in most of the patterns disclosed herein, to obtain more predictable results by reducing the variation caused by shooting through gas bubbles. However, it may be desirable to shoot cataracts from the anterior to the posterior for the purpose of choosing the lesser of two undesirable effects. Thus, it may be advantageous to shoot through the gas bubbles, or let them dissipate, rather then shooting through cataractus tissue, which much more severely scatters the light and more quickly prevents photodissruption compared to gas bubble interference. Accordingly, it is proposed to photodissrupt the most anterior sections of the cataract first, then move posteriorally, shooting through gas bubble remnants of cataractous tissue, to the next layer of cataract tissue below. In addition to shooting the laser in anterior z planes then moving posterior, it is further provided to essentially drill down anterior to posterior, which we call the z axis throughout this document and then move in x/y and drill down again.

EXAMPLE 14 provides for a clear lens extraction. In this example the shot pattern of FIG. 25 is applied to a clear lens and that lens material is subsequently removed. In this example shooting from posterior to anterior is desirable.

EXAMPLE 15 provides for a precision capsulorhexis. The creation of precise capsulorhexis for the surgeon to access the lens to remove the lens material is provided. As illustrated in FIGS. 30A-D, there is provided an outer surface 3001 and thus an outer shape of the lens. There is further provided a ring shaped band shape cut 3002 and shot pattern. Thus, the figure shows the cross section view of this ring shaped annular band and accordingly provides for two sides 3002 of the ring. The ring shaped capsulorhexis cuts of 100 μm deep, approximately centered on the anterior lens capsule surface and precisely 5 mm in diameter. Since the lens capsule is approximately 5 to 15 μm thick, it is desirable for the depth of the cut to be typically between 5 and several hundred um, although there is not much penalty for cutting several millimeters. This diameter, however, can be varied between 0.1 mm to 9 mm diameter and the capsulorhexis can be elliptical with the x axis different then the y axis or other shapes. A particular IOL may benefit from and/or may require a particular capsulorhexis shape.

Figures 31A, 31B:
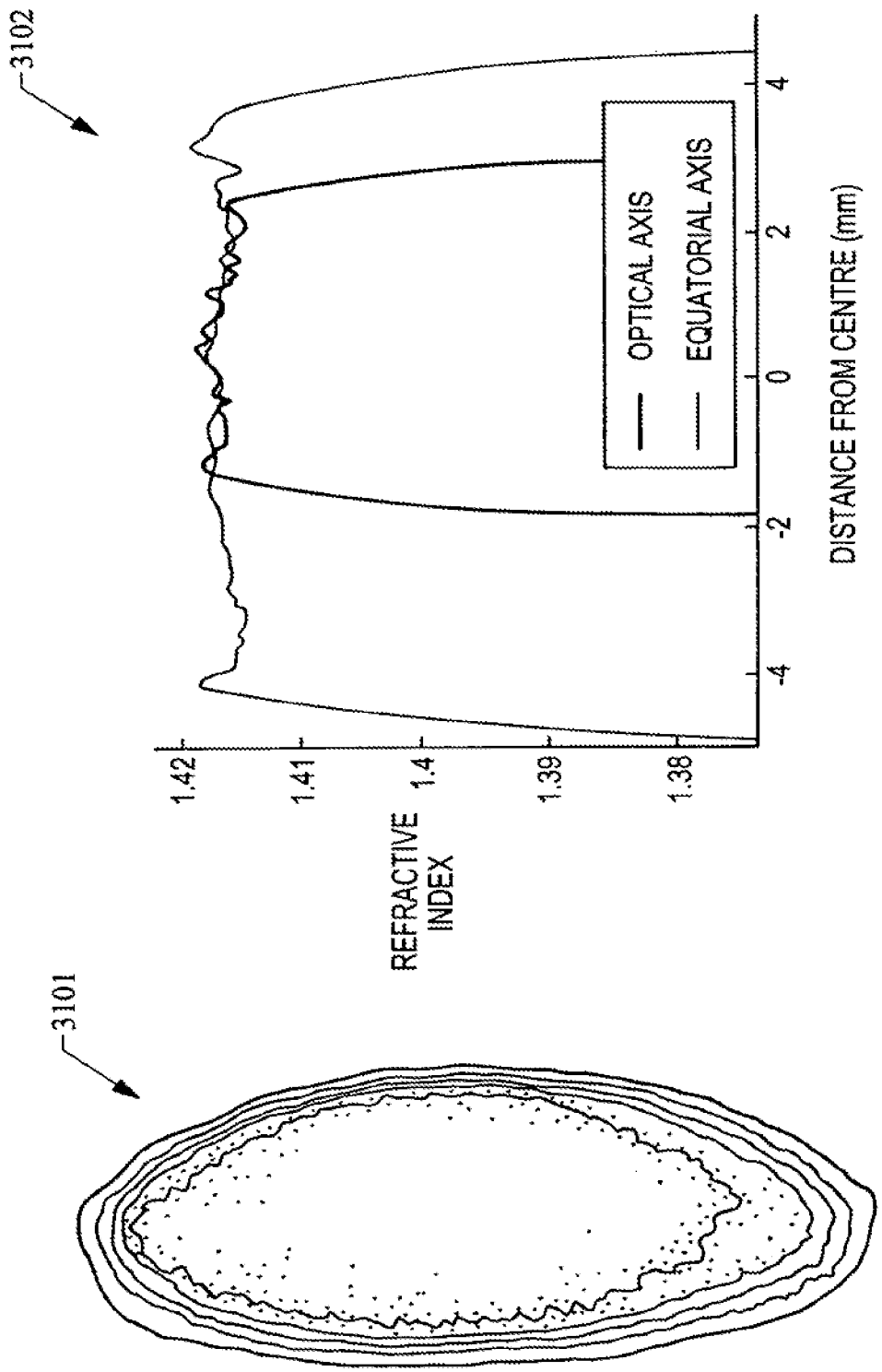
FIGS. 31A-D are diagrams illustrating youthful vs old age gradient index behavior.
Figures 31C, 31D:
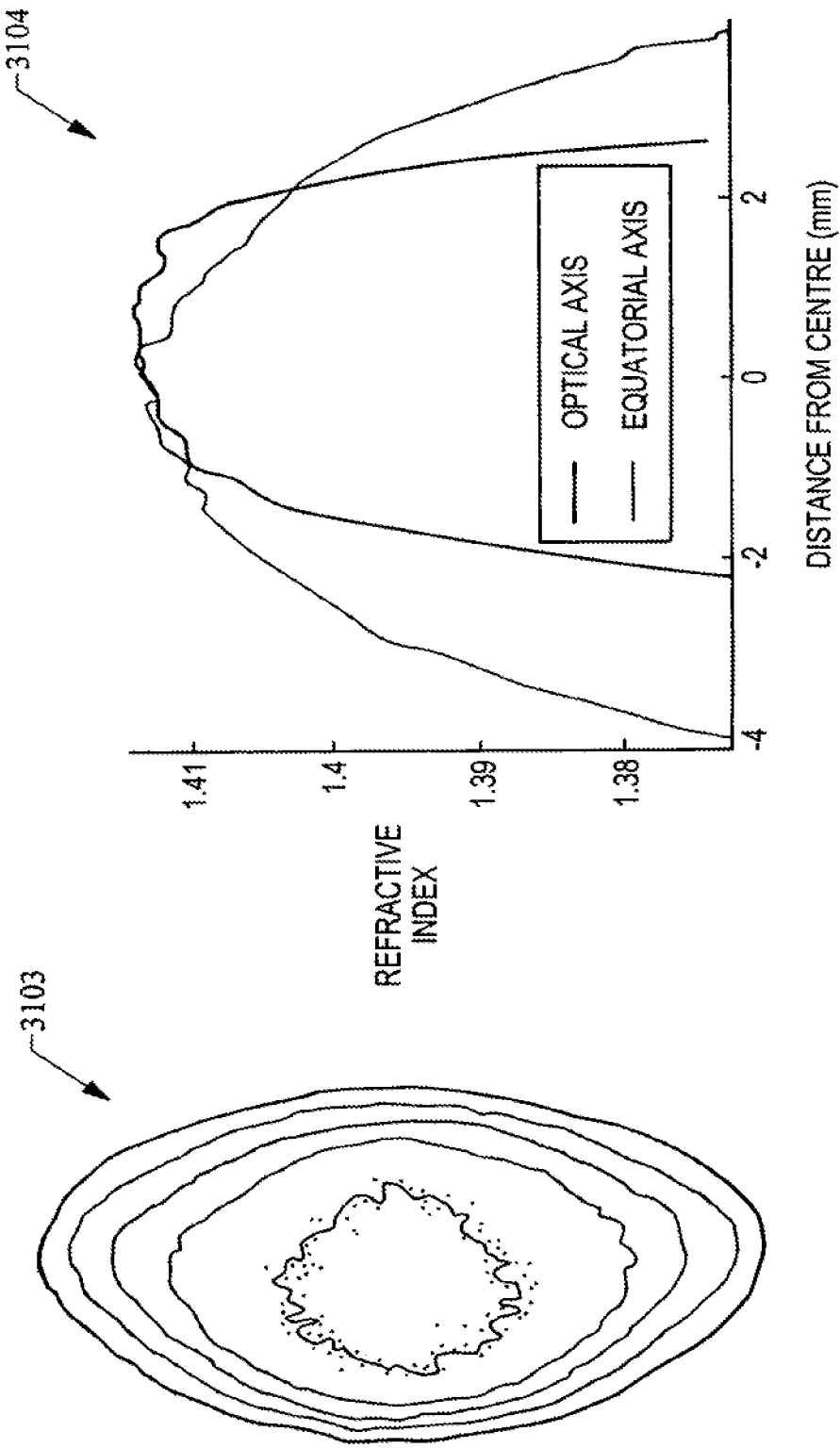

Examples 16 to 17 relate to gradient index modification of the lens. Moffat, Atchison and Pope, Vision Research 42 (2002) 1683-1693, showed that the natural crystalline lens contains a gradient index of refraction behavior that follows the lens shells structure and dramatically contributes to overall lens power. They also showed that this gradient substantially diminishes, or flattens as the lens ages reducing the optical power of the lens. The loss of gradient index with age most likely explains the so-called Lens Paradox, which presents the conundrum that the ageing lens is known to grow to a steeper curvature shape that should result in higher power, yet the aging lens has similar power to the youthful lens. Essentially it is postulated that the increase in power due to shape changes is offset by the power loss from gradient index loss. Examples of the youthful vs old age gradient index behavior is shown in FIG. 31, which provides data taken from the more recent work from the same group Jones, Atchison, Meder and Pope, Vision Research 45 (2005) 2352-236. We can see from this figure that the old lens 3101 has a flat index behavior radially 3102 and the young lens 3103 has continuously diminishing index radially 3104 from approximately 1.42 in the center to 1.38 nearer the outer shells of the lens. Thus, based upon this data it is provided to use the photodissruptive laser in the creation of small voids within the lens fiber material which will then fill-in with aqueous humor fluid which has a lower index of refraction and, via area weighting or volume weighting, decrease the net refractive index of a particular region. Accordingly, if different void densities are placed in nested shell volumes, then this would diminish the average index of refraction of essentially concentric regions in a similar manner to the youthful lens.

Figure 26:
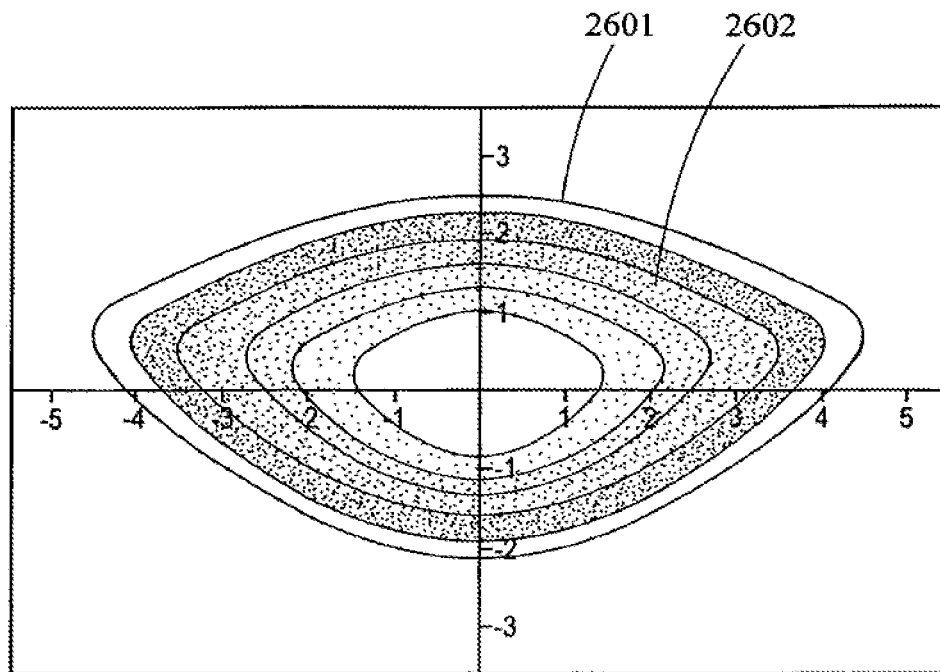
FIGS. 26-27 are cross-section drawings of a lens showing the placement of a gradient index modification laser shot patterns in accordance with the teachings of the present invention.

EXAMPLE 16 provides a gradient index modification, which has different void densities placed in nested volumes, as shown in FIG. 26. Thus, there is provided a series of nested shot patterns 2602 and a lens outer surface 2601, with each pattern creating an incrementally different void density in the lens material. For example, if a nominal 25% weighting efficiency was obtained in the most densely treated region, filling that volume with 1.38 index of aqueous humor, and the remaining region that was 75% lens material of index 1.42, then the average resultant index of refraction would be 0.25*1.38+0.75*1.42 or 1.41, which we see from FIG. 31, that would restore the gradient from the center to a 2 mm radius, which is most central optical region for visual function. Thus, FIG. 26 shows a distributed regional treatment of increasing density from the center of the lens to the periphery of the lens.

Figure 27:
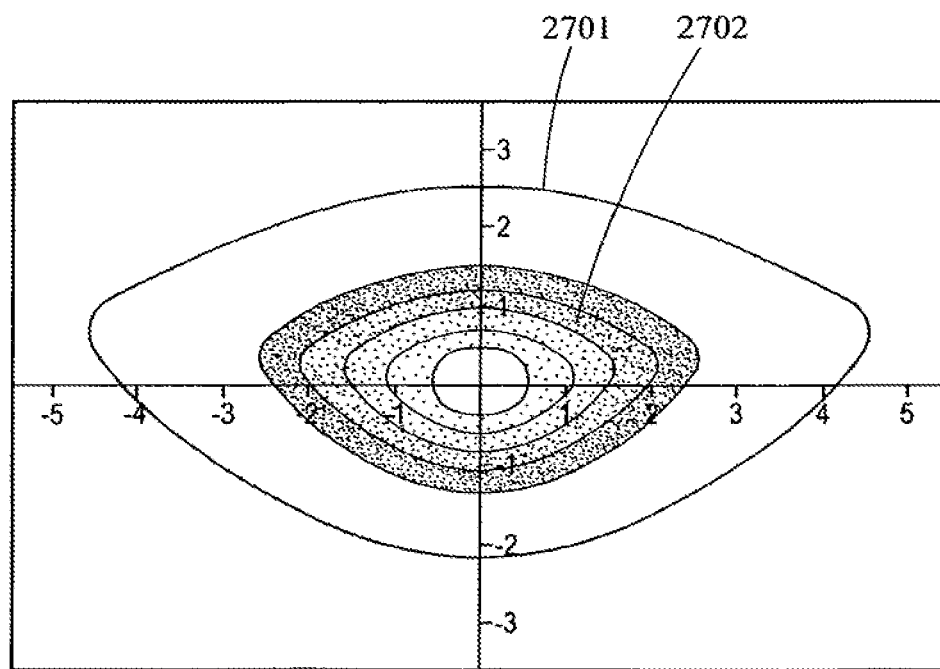

EXAMPLE 17 provides a gradient index modification that is similar to example 16, except that the area where void density is changed is located further from the outer surface of the lens. This example and pattern is illustrated in FIG. 27. Thus there is provided a series of nested shot patterns 2702 and lens outer surface 2701, with each pattern creating an incrementally different void density in the lens material. Moreover, this figure shows a distributed regional shell treatment that is primarily confined to the nucleus.

Figure 28A:
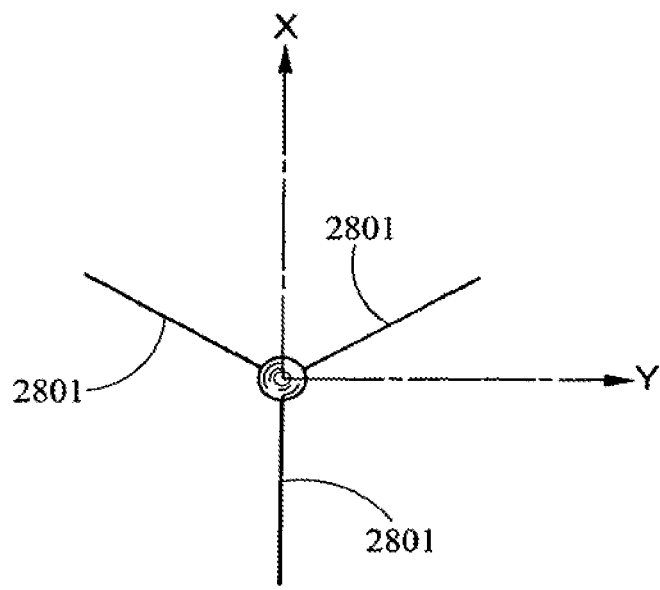
FIGS. 28A, C and E diagrams depicting laser suture cut shot patterns on the anterior portion of a lens of the present invention.
Figure 28B:
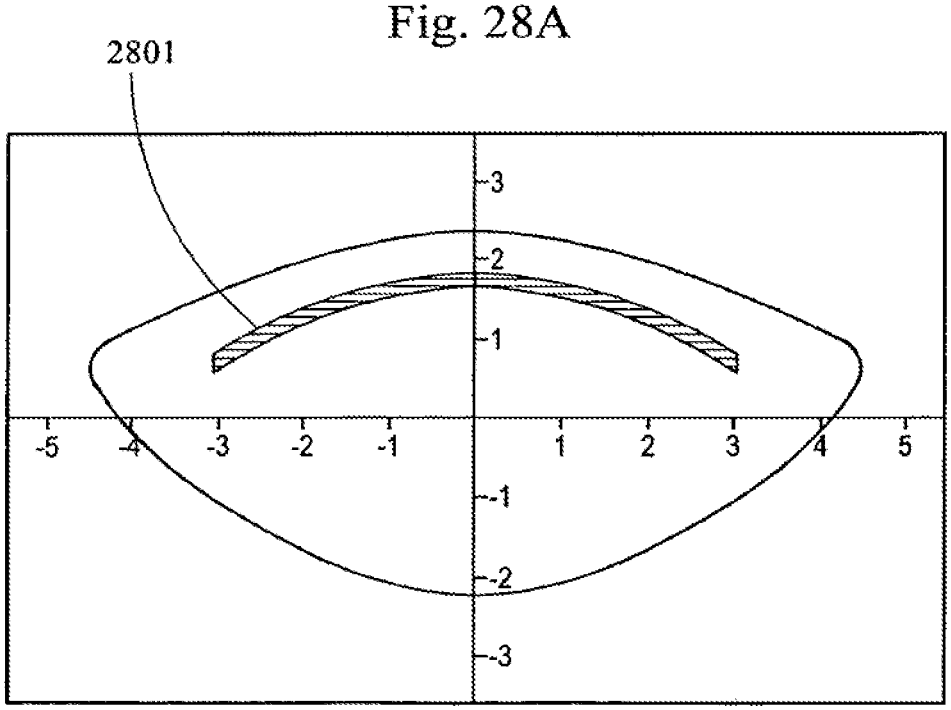
FIGS. 28B, D, and F are diagrams illustrating the placement of the shot patterns of FIGS. 28A, C, and E respectively.
Figure 28C:
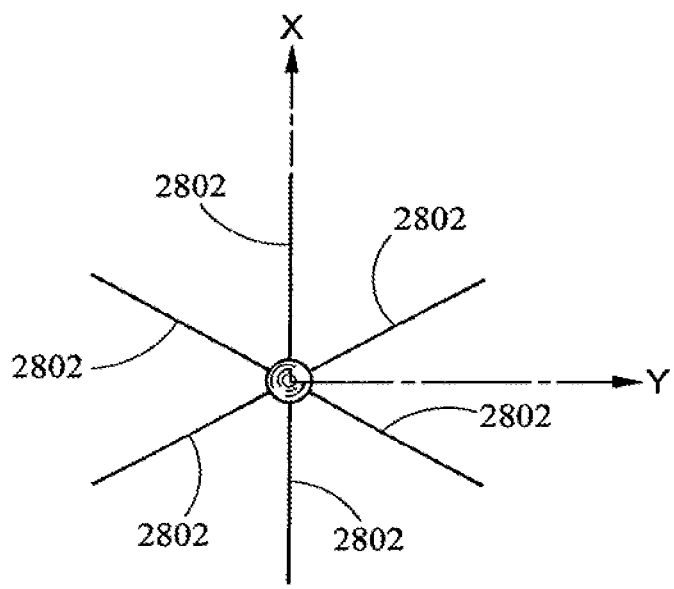
Figure 28D:
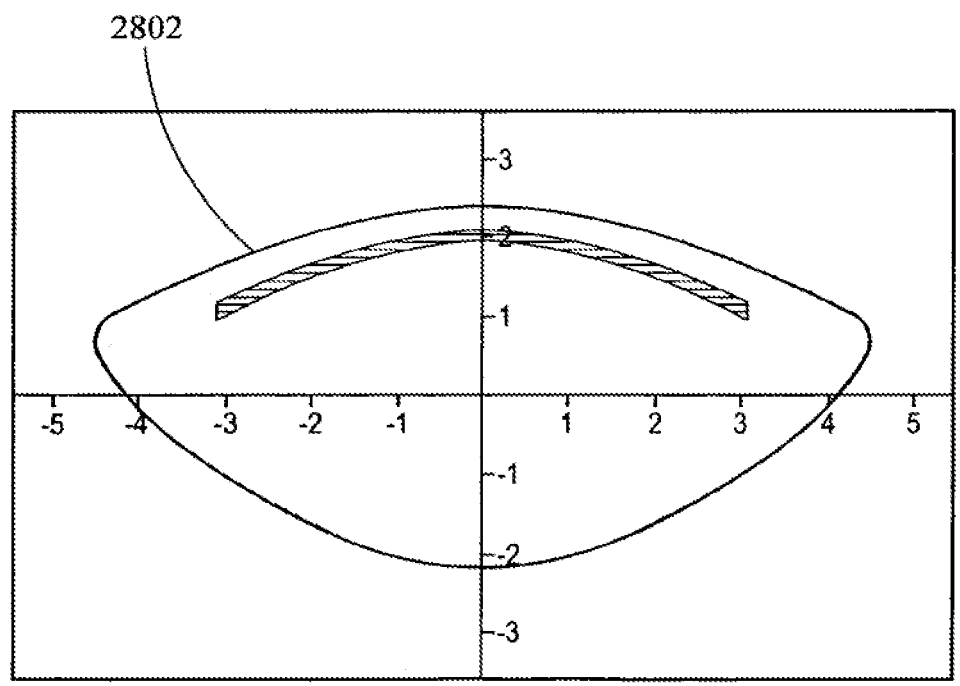
Figure 28E:
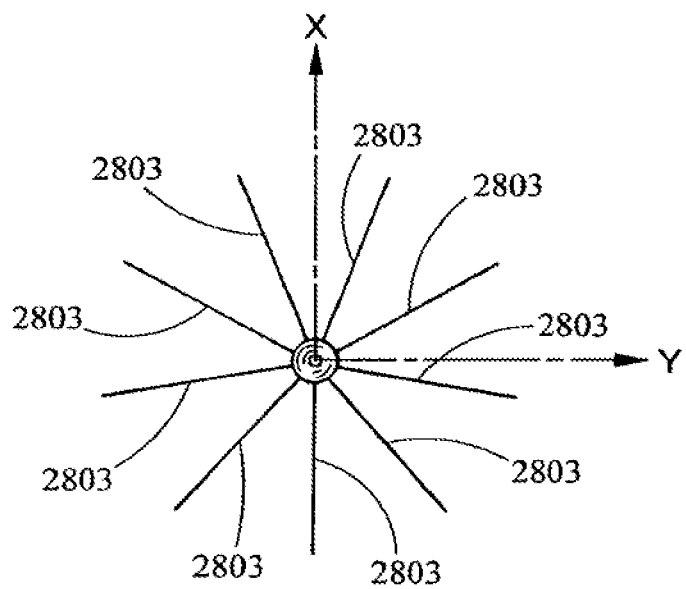
Figure 28F:
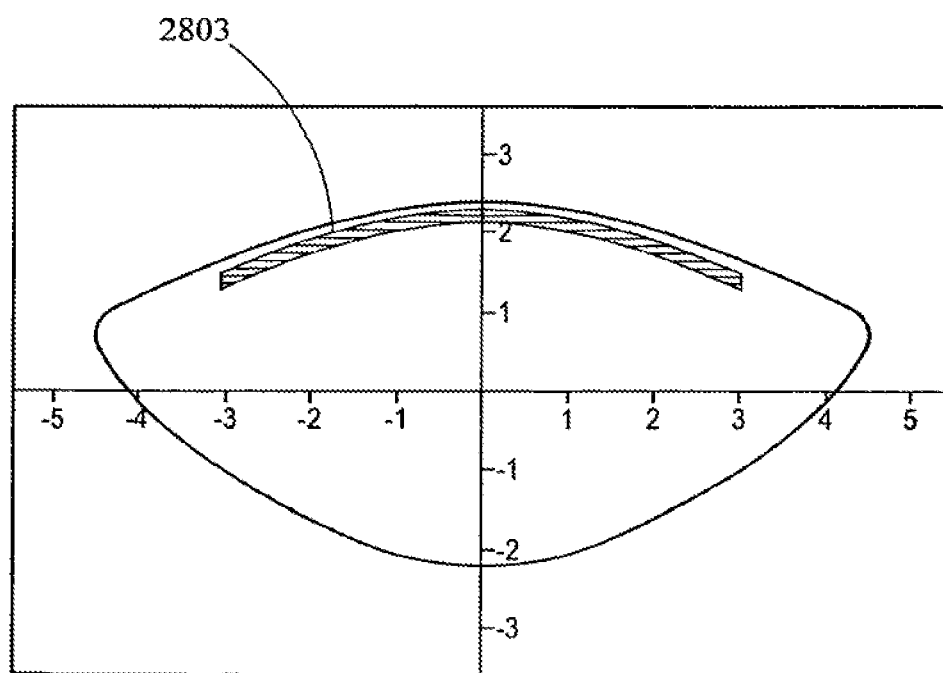
Figure 29:
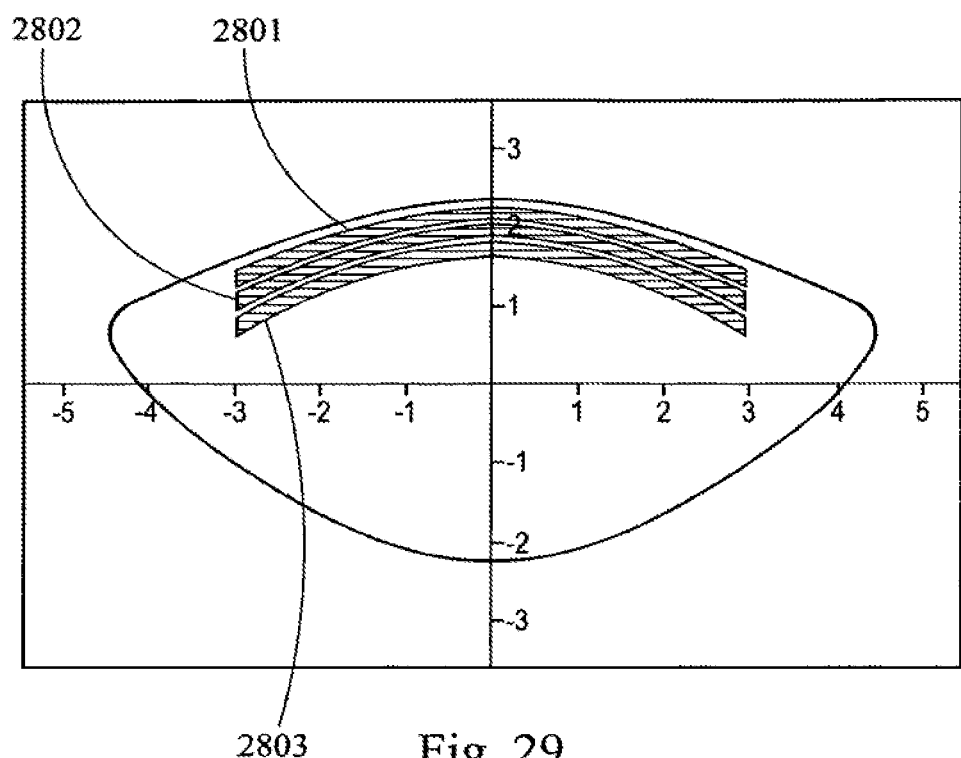
FIG. 29 is a diagram illustrating the relative placement of the shot patterns of FIGS. 28A, C, and E, if performed in the same lens.
Figure 30A:
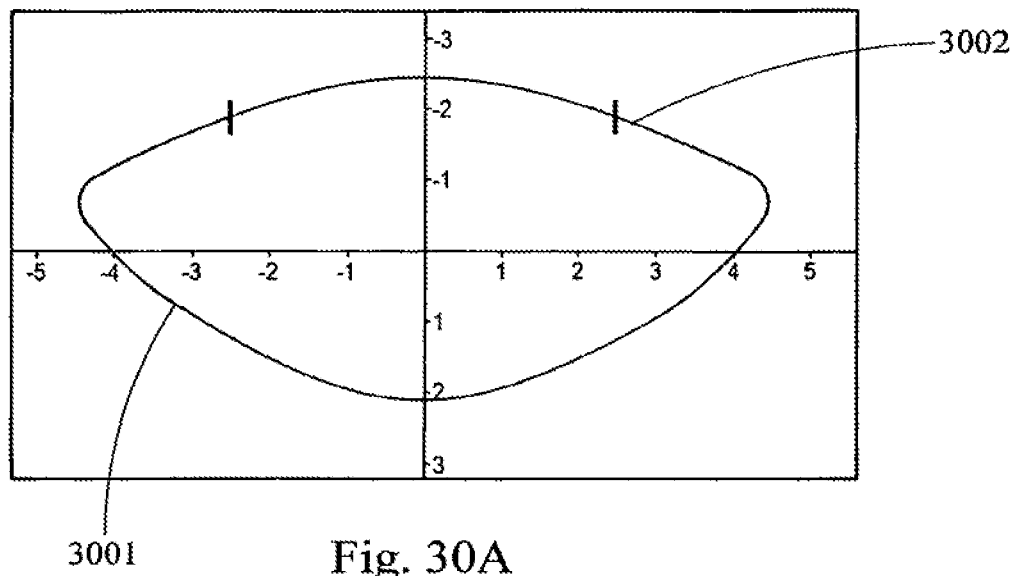
FIGS. 30A-D are diagrams of the cross-section of a lens illustrating a capsulorhexis shot pattern of the present invention.
Figure 30B:
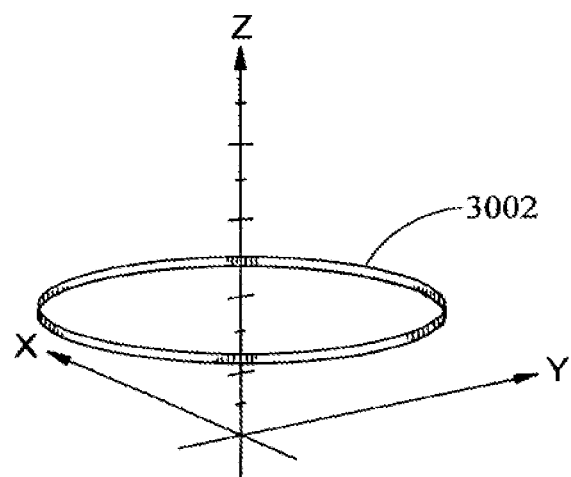
Figure 30C:
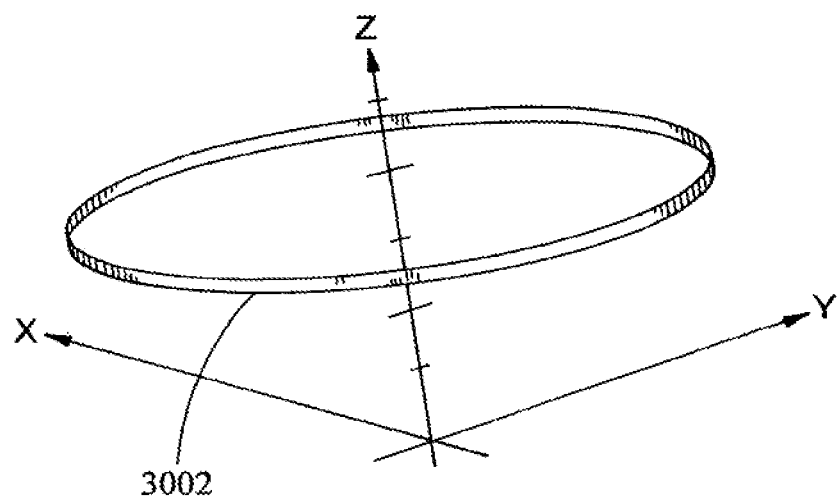
Figure 30D:
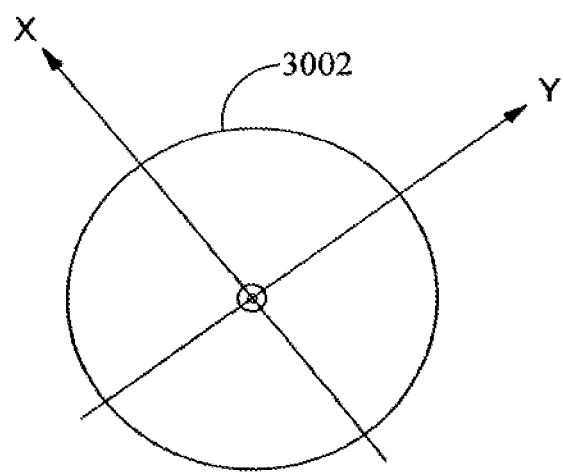

EXAMPLE 18 provides for the cutting in relation to suture lines. Thus, cuts along either modeled suture lines, according to Kuzak described suture locations as a function of shell geometry with age and shape, or measured suture lines may be used. The latter being provided by the measuring of patient lens sutures with a CCD camera and aligning suture cuts to the measured locations of suture lines. Thus, the brightest suture lines and or those with the widest spatial distribution likely belong to the deepest layers, and perhaps the initial Y suture branches found in the fetal nucleus. Further, there it is provided to cut Y suture shapes at the lowest layers in the lens and then increasing the number of cuts as the layers move out peripherally. Thus, according to these teachings, FIGS. 28 & 29 shows three different cutting patterns 2801, 2802, 2803 in the anterior portion of the lens that can be done separately or in combination. Thus, FIGS. 28A, C & E shows x-y cuts 2801, 2802, 2803 looking down at the anterior side of the lens. FIGS. 28B, D, and F are schematic representation to illustrate that the star shaped patterns follow the shape of the layer of the lens and do not show the actual cut. FIG. 29 is the combination of the illustrations in FIGS. 28B, D, and F to show their relative positions. It is understood that similar suture cuts can be made in the posterior following the posterior shell curves there, based again on either modeled geometry or measured lens data. There is yet further provided cutting 3, 4, 5, 6, 7, 8, 9, 10, 11, 12, 13, 14 and 15 branch sutures per Kuszak., cut separately or in any combination.

The components and their association to one another for systems that can perform, in whole or in part, these examples are set forth above in detail. Additionally, it is noted that the functions of the methods and systems disclosed herein may be performed by a single device or by several devices in association with each other. Accordingly, based upon these teachings a system for performing these examples, or parts of these examples, may include by way of illustration and without limitation a laser, an optical system for delivering the laser beam, a scanner, a camera, an illumination source, and an applanator. These components are positioned so that when the eye is illuminated by the illumination source, light will travel from the eye through the applanator to the scanner. In this system the illumination source is movable with respect to the eye to provide varying angles by which the eye can be illuminated.

Similarly, such system may also include by way of example and without limitation a laser, a system for determining the position and shape of components of an eye, a camera, a controller (which term refers to and includes without limitation processors, microprocessors and/or other such types of computing devices that are known to those of skill in the art to have the capabilities necessary to operate such a system), an illumination source, and an eye interface device. In this system the scanner is optically associated with the eye interface device, such that when the eye is illuminated by the illumination source, light will travel from the eye through the eye interface device to the scanner. The scanner is further optically associated with the camera, such that the scanner has the capability to provide stereo pairs of images of the eye to the camera. The camera is associated with the controller and is capable of providing digital images of the eye to the controller; and, the controller further has the capability to determine, based in part upon the digital images provided from the camera, the shape, position and orientation of components of the eye.

Moreover, such systems may also include by way of example and without limitation a system for delivering a laser to an eye. This system would have a laser, a scanner, a camera, an illumination source, an eye interface device, a means for determining the shape and position of components within an eye and a means for directing the delivery of a laser beam from the laser to a precise three dimensional coordinate with respect to the components of the eye, the means for directing the delivery of the laser beam having the capability to direct the beam based at least in part on the determination of the shape and position of components within the eye by the determining means.

From the foregoing description, one skilled in the art can readily ascertain the essential characteristics of this invention, and without departing from the spirit and scope thereof, can make various changes and/or modifications of the invention to adapt it to various usages and conditions.

What is claimed:

1. A laser system for treating a cataractous natural crystalline lens of an eye, the laser system comprising:
   a. a laser that generates a therapeutic laser beam;
   b. an optical assembly that receives, directs and focuses the therapeutic laser beam to a predetermined location associated with the laser system;
   c. the optical assembly comprising a z-focus device and an x, y scanner;
   d. the optical assembly and laser defining a therapeutic laser beam delivery path;
   e. a patient interface device for associating the cornea of an eye of a patient with the laser system, the patient interface device having a curved transparent element for mating with the cornea;

f. the curved transparent element positioned in the therapeutic laser beam delivery path;

g. a lens position determination assembly comprising:
   i. a coherent light source to provide an illumination beam;
   ii. an x, y scanner;
   iii. a z-focus device;
   iv. an image capture device for providing observed data;
   v. a processor associated with the image capture device and for determining a position of the cataractous natural crystalline lens with respect to the laser, whereby the processor receives actual observed data from the image capture device; and,
   vi. wherein the light source, the x, y scanner of the lens position determination assembly, the z-focus device of the lens position determination assembly, and the image capture device define an illumination beam path;
   vii. whereby the illumination beam path pass through the curved transparent element; and, h. the processor capable of modeling a shape for the cataractous natural crystalline lens with respect to the laser.

2. The laser system of claim 1, wherein the predetermined location is coincident with a modeled shape for the cataractous natural crystalline lens of the eye.

3. The laser system of claim 1, wherein the predetermined location is based upon a modeled shape for the cataractous natural crystalline lens of the eye.

4. A laser system for treating a cataractous natural crystalline lens of an eye, the laser system comprising:
   a. a laser that generates a therapeutic laser beam;
   b. an optical assembly that receives, directs and focuses the therapeutic laser beam to a predetermined location associated with the laser system;
   c. the optical assembly comprising a z-focus device and an x, y scanner;
   d. the optical assembly and laser defining a therapeutic laser beam delivery path;
   e. a patient interface device for associating the cornea of an eye of a patient with the laser system, the patient interface device having a curved transparent element for mating with the cornea;
   f. the curved transparent element positioned in the therapeutic laser beam delivery path;
   g. a lens position determination assembly comprising:
      i. a coherent light source to provide an illumination beam;
      ii. an x, y scanner;
      iii. a z-focus device;
      iv. an image capture device for providing observed data;
      v. a processor associated with the image capture device and for providing a determined position of the cataractous natural crystalline lens with respect to the laser, whereby the processor receives actual observed data from the image capture device; and,
      vi. wherein the light source, the x, y scanner of the lens position determination assembly, the z-focus device of the lens position determination assembly, and the image capture device define an illumination beam path;
      vii. whereby the illumination beam path pass through the curved transparent element; and,
   h. the processor capable of providing a modeled position for the cataractous natural crystalline lens with respect to the laser.

5. The laser system of claim 4, wherein the modeled position is coincident with the determined position for the cataractous natural crystalline lens of the eye.

6. The laser system of claim 4, wherein the modeled position is based upon the determined position for the cataractous natural crystalline lens of the eye.

* * * * *